US012595303B2

(12) United States Patent
Maus et al.

(10) Patent No.: US 12,595,303 B2
(45) Date of Patent: Apr. 7, 2026

(54) ANTIBODIES AND CHIMERIC ANTIGEN RECEPTORS THAT TARGET TACI

(71) Applicant: The General Hospital Corporation, Boston, MA (US)

(72) Inventors: Marcela V. Maus, Lexington, MA (US); Rebecca Larson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1059 days.

(21) Appl. No.: 17/616,274

(22) PCT Filed: Jun. 4, 2020

(86) PCT No.: PCT/US2020/036108
§ 371 (c)(1),
(2) Date: Dec. 3, 2021

(87) PCT Pub. No.: WO2020/247618
PCT Pub. Date: Dec. 10, 2020

(65) Prior Publication Data
US 2022/0324964 A1 Oct. 13, 2022

Related U.S. Application Data

(60) Provisional application No. 63/012,735, filed on Apr. 20, 2020, provisional application No. 62/907,930, filed on Sep. 30, 2019, provisional application No. 62/856,998, filed on Jun. 4, 2019.

(51) Int. Cl.
| | |
|---|---|
| *C07K 16/28* | (2006.01) |
| *A61K 39/00* | (2006.01) |
| *A61K 40/11* | (2025.01) |
| *A61K 40/31* | (2025.01) |
| *A61K 40/42* | (2025.01) |
| *A61P 35/00* | (2006.01) |

(52) U.S. Cl.
CPC .............. *C07K 16/28* (2013.01); *A61K 40/11* (2025.01); *A61K 40/31* (2025.01); *A61K 40/4202* (2025.01); *A61K 40/4215* (2025.01); *A61P 35/00* (2018.01); *A61K 2039/505* (2013.01); *A61K 2239/31* (2023.05); *A61K 2239/38* (2023.05); *A61K 2239/46* (2023.05); *A61K 2239/48* (2023.05); *C07K 2317/24* (2013.01); *C07K 2317/31* (2013.01); *C07K 2317/565* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 2005/0032175 A1 | 2/2005 | Stahl et al. | |
| 2005/0043516 A1* | 2/2005 | Chuntharapai | ......... A61P 19/02 530/387.9 |
| 2010/0041074 A1 | 2/2010 | Kimura | |

FOREIGN PATENT DOCUMENTS

| | | |
|---|---|---|
| AU | 2015221933 A1 | 9/2016 |
| CN | 108490174 A | 9/2018 |
| CN | 109153731 A | 1/2019 |
| JP | 2005-533863 A | 11/2005 |
| WO | WO 02/066516 A2 | 8/2002 |
| WO | WO 2004/011611 A2 | 2/2004 |
| WO | WO 2004/074511 A1 | 9/2004 |
| WO | WO 2017/040324 A1 | 3/2017 |
| WO | WO 2018/087557 A1 | 5/2018 |
| WO | WO 2020/247618 A1 | 12/2020 |

OTHER PUBLICATIONS

Rudikoff, et al., PNAS, 1982, 79, p. 1979-1983 (Year: 1982).*
Janeway, et al., Immunobiology: The Immune System in Health and Disease, 5th edition, 2001 (Year: 2001).*
Seshasayee et al., Loss of TACI causes fatal lymphoproliferation and autoimmunity, establishing TACI as an inhibitory BLyS receptor. Immunity. Feb. 2003;18(2):279-88. doi: 10.1016/s1074-7613(03)00025-6.
Atkin et al., What is the significance of monoclonal gammopathy of undetermined significance? Clin Med (Lond). Oct. 2018;18(5):391-396. doi: 10.7861/clinmedicine.18-5-391.
Chatterjee et al., Clinical Relevance of Multicolour Flow Cytometry in Plasma Cell Disorders. Indian J Hematol Blood Transfus. Sep. 2017;33(3):303-315. doi: 10.1007/s12288-017-0822-z. Epub Apr. 26, 2017.

(Continued)

*Primary Examiner* — Michael Szperka
*Assistant Examiner* — Samantha Lake Hopkins
(74) *Attorney, Agent, or Firm* — Wolf, Greenfield & Sacks, P.C.

(57) ABSTRACT

The invention provides antibodies, antibody-drug conjugates, bispecific T cell engagers (BiTEs), and chimeric antigen receptors (CARs) that target transmembrane activator and calcium modulator and cyclophilin ligand interactor (TACI). Such antibodies, antibody-drug conjugates, BiTEs, and CARs can be used, e.g., in methods for treating a cancer (e.g., multiple myeloma), an autoimmune disorder (e.g., characterized by a high titer of antibodies contributing to the disorder), or a plasma cell disease disorder (e.g., plasma cell dyscrasias) in a subject in need thereof.

10 Claims, 51 Drawing Sheets

Specification includes a Sequence Listing.

(56) References Cited

OTHER PUBLICATIONS

Corcos et al., B-cell receptors and heavy chain diseases: guilty by association? Blood. Jun. 30, 2011;117(26):6991-8. doi: 10.1182/blood-2011-02-336164. Epub Apr. 20, 2011.

Tsuji et al., TACI deficiency impairs sustained Blimp-1 expression in B cells decreasing long-lived plasma cells in the bone marrow. Blood. Nov. 24, 2011;118(22):5832-9. doi: 10.1182/blood-2011-05-353961. Epub Oct. 7, 2011.

* cited by examiner

K562-BCMA

K562-TACI

FIG. 19

RPMI8226

U266

Donor 3

| Anti-TACI – anti-BCMA Bispecific | Anti-BCMA – anti-TACI Bispecific | Untransduced t cells |
|---|---|---|

Day -1

Day 4

Day 7

Day 11

Representative images from Donor 1

D-14: 5e6
RPMI SubQ

2e6
CAR IV

D0    D4    D7    D10    D14

Caliper
measurements

▼  Anti-TACI - anti-BCMA bispecific
○  Anti-BCMA - anti-TACI bispecific
●  Untransduced
▵  Tumor Only CAR expansion in the blood Day 14

CAR expansion in the blood Day 21

D0          D7          D14          D21          D28

1e6 CAR
stim

Flow for exhaustion and
memory phenotype, count
and restim with
overexpressing K562

-△- Anti-BCMA
-▽- Anti-TACI - anti-BCMA bispecific
-◇- Anti-BCMA - anti-TACI bispecific
-■- Untransduced
-○- Unstimulated

ANTIBODIES AND CHIMERIC ANTIGEN RECEPTORS THAT TARGET TACI

RELATED APPLICATIONS

This application is a national stage filing under 35 U.S.C. § 371 of International PCT Application PCT/US2020/036108, filed Jun. 4, 2020, entitled "ANTIBODIES AND CHIMERIC ANTIGEN RECEPTORS THAT TARGET TACI," which claims the benefit under 35 U.S.C. § 119(e) to U.S. Provisional Application No. 62/856,998, filed Jun. 4, 2019, entitled "ANTIBODIES AND CHIMERIC ANTIGEN RECEPTORS THAT TARGET TACI," to U.S. Provisional Application No. 62/907,930, filed Sep. 30, 2019, entitled "ANTIBODIES AND CHIMERIC ANTIGEN RECEPTORS THAT TARGET TACI," and to U.S. Provisional Application No. 63/012,735, filed Apr. 20, 2020, entitled "ANTIBODIES AND CHIMERIC ANTIGEN RECEPTORS THAT TARGET TACI," the entire contents of each of which are incorporated herein by reference.

BACKGROUND

Chimeric antigen receptors (CARs) direct cytotoxic T cell responses to target cells expressing a selected target antigen, most often a tumor antigen or tumor-associated antigen. CARs are an adaptation of the T cell receptor, where the antigen binding domain is replaced with the antigen binding domain of an antibody that specifically binds the derived target antigen. Engagement of the target antigen on the surface of a target cell by a CAR expressed on, e.g., a T cell ("CAR T cell" or "CAR-T"), promotes killing of the target cell.

SUMMARY

Described herein are antibodies, antibody-drug conjugates, bispecific T cell engagers (BiTEs), and chimeric antigen receptors (CARs) that target transmembrane activator and calcium modulator and cyclophilin ligand interactor (TACI), which can be useful for treating a subject having a disease or disorder, e.g., a cancer, a plasma cell disease or disorder, or an autoimmune disease or disorder.

Some aspects of the present disclosure provide antibodies that specifically binds to transmembrane activator and calcium modulator and cyclophilin ligand interactor (TACI), wherein the antibody comprises:

(i) a heavy chain complementarity-determining region 1 (CDR-H1), a heavy chain complementarity-determining region 2 (CDR-H2), and a heavy chain complementarity-determining region 3 (CDR-H3) of a heavy chain variable region (VH) comprising the amino acid sequence of SEQ ID NO: 1; and/or (ii) a light chain complementarity-determining region 1 (CDR-L1), a light chain complementarity-determining region 2 (CDR-L2), and a light chain complementarity-determining region 3 (CDR-L3) of a light chain variable region (VL) comprising the amino acid sequence of SEQ ID NO: 2.

In some embodiments, the antibody comprises:

(i) a CDR-H1 as set forth in SEQ ID NO: 26, a CDR-H2 as set forth in SEQ ID NO: 27, and a CDR-H3 as set forth in SEQ ID NO: 28; a CDR-L1 as set forth in SEQ ID NO: 29, a CDR-L2 as set forth in SEQ ID NO: 30, and a CDR-L3 as set forth in SEQ ID NO: 31;

(ii) a CDR-H1 as set forth in SEQ ID NO: 32, a CDR-H2 as set forth in SEQ ID NO: 33, and a CDR-H3 as set forth in SEQ ID NO: 34; a CDR-L1 as set forth in SEQ ID NO: 35, a CDR-L2 as set forth in SEQ ID NO: 36, and a CDR-L3 as set forth in SEQ ID NO: 31; or (iii) a CDR-H1 as set forth in SEQ ID NO: 37, a CDR-H2 as set forth in SEQ ID NO: 38, and a CDR-H3 as set forth in SEQ ID NO: 39; a CDR-L1 as set forth in SEQ ID NO: 40, a CDR-L2 as set forth in SEQ ID NO: 30, and a CDR-L3 as set forth in SEQ ID NO: 41.

In some embodiments, the antibody binds to TACI with a $K_D$ of about 2 nM or lower, optionally wherein the antibody binds to TACI with a $K_D$ between about 500 pM and about 1 nM, further optionally wherein the antibody binds to TACI with a $K_D$ between about 700 pM and about 900 pM. In some embodiments, the antibody binds to TACI with a $K_D$ with a $K_D$ of about 861 pM.

In some embodiments, the antibody comprises a heavy chain variable domain (VH) comprising an amino acid sequence having at least 80% sequence identity to the amino acid sequence of SEQ ID NO: 1 and/or a light chain variable domain (VL) comprising an amino acid sequence having at least 80% sequence identity to the amino acid sequence of SEQ ID NO: 2. In some embodiments, the VH comprises an amino acid sequence having at least 85% sequence identity to the amino acid sequence of SEQ ID NO: 1 and the VL comprises an amino acid sequence having at least 85% sequence identity the amino acid sequence of SEQ ID NO: 2. In some embodiments, the antibody comprises a VH comprising the amino acid sequence of SEQ ID NO: 1 and a VL comprising the amino acid sequence of SEQ ID NO: 2.

In some embodiments, the antibody is a monoclonal, human, humanized, or chimeric antibody. In some embodiments, the antibody is a monoclonal antibody. In some embodiments, the antibody is a full-length antibody. In some embodiments, the antibody is an antibody fragment that specifically binds TACI. In some embodiments, the antibody fragment is selected from the group consisting of Fab, Fab', Fab'-SH, Fv, scFv, and (Fab')₂ fragments. In some embodiments, the antibody is an IgG antibody, optionally an IgG1 antibody. In some embodiments, the antibody is a scFv. In some embodiments, the scFv comprises an amino acid sequence that is at least 85% identical to SEQ ID NO: 4 or SEQ ID NO: 5. In some embodiments, the scFv comprises the amino acid sequence of SEQ ID NO: 4 or SEQ ID NO: 5. In some embodiments, the scFv is fused to a Fc.

Another aspect of the invention described herein relates to a composition comprising any one of the antibodies described herein.

Another aspect of the invention described herein relates to a polynucleotide encoding any one of the antibodies described herein.

Another aspect of the invention described herein relates to a vector comprising any one of the polynucleotides described herein.

Another aspect of the invention described herein relates to a host cell comprising any one of the vectors described herein.

In one embodiment, the host cell is a mammalian cell. In one embodiment, the mammalian cell is a Chinese hamster ovary (CHO) cell.

In another embodiment, the host cell is a prokaryotic cell. In one embodiment, the prokaryotic cell is E. coli.

Another aspect of the invention described herein relates to a method of producing an antibody that specifically binds TACI, the method comprising culturing any one of the host cells described herein in a culture medium. In one embodiment, the method further comprises recovering the antibody from the host cell or the culture medium.

Another aspect of the invention described herein relates to an antibody-drug conjugate comprising any one of the antibodies described herein.

Another aspect of the invention described herein relates to a chimeric antigen receptor (CAR) polypeptide comprising an extracellular target binding domain, wherein the extracellular target binding domain comprises a TACI-binding domain.

In one embodiment, the CAR polypeptide comprises a transmembrane domain and an intracellular signaling domain.

In one embodiment, the CAR polypeptide further comprises one or more co-stimulatory domains.

In one embodiment, the TACI-binding domain does not comprise APRIL, BAFF, CAMLG, or a portion thereof.

In one embodiment, the TACI-binding domain binds to TACI with a $K_D$ of about 2 nM or lower. In one embodiment, the TACI-binding domain binds to TACI with a $K_D$ between about 500 pM and about 1 nM. In one embodiment, the TACI-binding domain binds to TACI with a $K_D$ between about 700 pM and about 900 pM. In one embodiment, the TACI-binding domain binds to TACI with a $K_D$ of about 861 pM.

In one embodiment, the TACI-binding domain comprises an antibody or an antigen binding fragment thereof.

Another aspect of the invention described herein relates to a CAR polypeptide comprising an extracellular target binding domain comprising any one of the antibodies described herein or an antigen binding fragment thereof.

In one embodiment of any aspect, the TACI-binding domain comprises an anti-TACI single chain variable fragment (scFv).

In one embodiment of any aspect, the anti-TACI scFv comprises a heavy chain variable domain (VH) comprising an amino acid sequence having at least 90% sequence identity to the amino acid sequence of SEQ ID NO: 1.

In one embodiment of any aspect, the VH comprises the amino acid sequence of SEQ ID NO: 1.

In one embodiment of any aspect, the anti-TACI scFv comprises a light chain variable domain (VL) comprising an amino acid sequence having at least 90% sequence identity to the amino acid sequence of SEQ ID NO: 2.

In one embodiment of any aspect, the VL comprises the amino acid sequence of SEQ ID NO: 2.

In one embodiment of any aspect, the anti-TACI scFv comprises a VH comprising the amino acid sequence of SEQ ID NO: 1 and a VL comprising the amino acid sequence of SEQ ID NO: 2.

In one embodiment of any aspect, the VH is positioned N-terminal to the VL.

In another embodiment of any aspect, the VL is positioned N-terminal to the VH.

In one embodiment of any aspect, the VH and the VL are connected via a linker sequence.

In one embodiment of any aspect, the linker sequence comprises the amino acid sequence of SEQ ID NO: 3, 14, 15, 16, or 17.

In one embodiment of any aspect, the linker sequence comprises the amino acid sequence of SEQ ID NO: 3.

In one embodiment of any aspect, the TACI-binding domain comprises an amino acid sequence having at least 90% sequence identity to the amino acid sequence of SEQ ID NO: 4 or 5.

In one embodiment of any aspect, the TACI-binding domain comprises the amino acid sequence of SEQ ID NO: 4 or 5.

In one embodiment of any aspect, the transmembrane domain comprises a hinge/transmembrane domain.

In one embodiment of any aspect, the hinge/transmembrane domain comprises the hinge/transmembrane domain of an immunoglobulin-like protein, CD28, CD8, or 4-1BB.

In one embodiment of any aspect, the hinge/transmembrane domain is the hinge/transmembrane domain of CD8, optionally wherein the hinge/transmembrane domain of CD8 comprises the amino acid sequence of SEQ ID NO: 7.

In one embodiment of any aspect, the intracellular signaling domain comprises the intracellular signaling domain of CD3ζ, CD3ε, or CD3θ.

In one embodiment of any aspect, the intracellular signaling domain comprises the intracellular signaling domain of CD3ζ, optionally wherein the intracellular signaling domain of CD3ζ comprises the amino acid sequence of SEQ ID NO: 9.

In one embodiment of any aspect, the co-stimulatory domain comprises the co-stimulatory domain of 4-1BB, CD28, CD27, ICOS, or OX40.

In one embodiment of any aspect, the co-stimulatory domain comprises the co-stimulatory domain of 4-1BB, optionally wherein the co-stimulatory domain of 4-1BB comprises the amino acid sequence of SEQ ID NO: 8.

In one embodiment of any aspect, the CAR polypeptide comprises an amino acid sequence having at least 90% sequence identity to the amino acid sequence of SEQ ID NO: 10, 11, 12, or 13.

In one embodiment of any aspect, the extracellular target binding domain further comprises a target-binding domain that binds to a second target that is not TACI.

In one embodiment of any aspect, the second target is B cell maturation antigen (BCMA).

In one embodiment of any aspect, the target-binding domain comprises a ligand of the second target.

In one embodiment of any aspect, the target-binding domain comprises an antibody or antigen-binding fragment thereof.

In one embodiment of any aspect, the antibody or antigen-binding fragment thereof comprises an scFv.

In one embodiment of any aspect, the scFv is an anti-BCMA scFv.

In one embodiment of any aspect, the anti-BCMA scFv is positioned N-terminal to the anti-TACI scFv.

In one embodiment of any aspect, the anti-TACI scFv is positioned N-terminal to the anti-BCMA scFv.

In one embodiment of any aspect, the CAR polypeptide comprises an amino acid sequence having at least 90% sequence identity to the amino acid sequence of any one of SEQ ID NOs: 18-25.

Another aspect of the invention described herein relates to a CAR polypeptide comprising the amino acid sequence of SEQ ID NO: 10.

Another aspect of the invention described herein relates to a CAR polypeptide comprising the amino acid sequence of SEQ ID NO: 11.

Another aspect of the invention described herein relates to a CAR polypeptide comprising the amino acid sequence of SEQ ID NO: 12.

Another aspect of the invention described herein relates to a CAR polypeptide comprising the amino acid sequence of SEQ ID NO: 13.

Another aspect of the invention described herein relates CAR polypeptide comprising the amino acid sequence of any one of SEQ ID NOs: 18-25.

Another aspect of the invention described herein relates to a polynucleotide encoding any one of the CAR polypeptides described herein.

In one embodiment, the polynucleotide further comprises a suicide gene.

In one embodiment, the polynucleotide further comprises a sequence encoding a signal sequence.

Another aspect of the invention described herein relates to a mammalian cell comprising any one of the CAR polypeptides described herein and/or any one of the polynucleotides described herein. In one embodiment, the mammalian cell is an induced pluripotent stem cell (iPSC). In one embodiment, the mammalian cell is an immune cell. In one embodiment, the immune cell is a T cell or a natural killer (NK) cell. In one embodiment, the mammalian cell is a human cell.

Another aspect of the invention described herein relates to a bispecific antibody that binds TACI and CD3, wherein the bispecific antibody comprises a TACI-binding domain and a CD3-binding domain.

In one embodiment of any aspect, the TACI-binding domain binds to TACI with a $K_D$ of about 2 nM or lower. In one embodiment, the TACI-binding domain binds to TACI with a $K_D$ between about 500 pM and about 1 nM. In one embodiment, the TACI-binding domain binds to TACI with a $K_D$ between about 700 pM and about 900 pM. In one embodiment, the TACI-binding domain binds to TACI with a $K_D$ of about 861 pM.

In one embodiment of any aspect, the TACI-binding domain comprises a VH comprising an amino acid sequence having at least 95% sequence identity to the amino acid sequence of SEQ ID NO: 1 and/or a VL comprising an amino acid sequence having at least 95% sequence identity to the amino acid sequence of SEQ ID NO: 2.

Another aspect of the invention described herein relates to a bispecific antibody that specifically binds to TACI and CD3, wherein the bispecific antibody comprises a TACI-binding domain and a CD3-binding domain, wherein the TACI-binding domain comprises a VH comprising the amino acid sequence of SEQ ID NO: 1 and a VL comprising the amino acid sequence of SEQ ID NO: 2.

In one embodiment of any aspect, the TACI-binding domain is positioned N-terminal to the CD3-binding domain.

In one embodiment of any aspect, the CD3-binding domain is positioned N-terminal to the TACI-binding domain.

In one embodiment of any aspect, the TACI-binding domain and the CD3-binding domain are connected by a linker sequence.

In one embodiment of any aspect, the linker sequence comprises the amino acid sequence of SEQ ID NO: 3, 14, 15, 16, or 17.

In one embodiment of any aspect, the bispecific antibody is a monoclonal, human, humanized, or chimeric antibody.

In one embodiment of any aspect, the bispecific antibody is a monoclonal antibody.

In one embodiment of any aspect, the bispecific antibody is a full-length antibody.

In another embodiment of any aspect, the bispecific antibody is an antibody fragment that specifically binds TACI and CD3. In one embodiment, the antibody fragment is selected from the group consisting of Fab, Fab', Fab'-SH, Fv, scFv, and (Fab')$_2$ fragments.

In one embodiment of any aspect, the bispecific antibody is an IgG antibody. In one embodiment, the bispecific antibody is an IgG1 antibody.

Another aspect of the invention described herein relates to a composition comprising any one of the bispecific antibodies described herein.

Another aspect of the invention described herein relates to a polynucleotide encoding any one of the bispecific antibodies described herein.

Another aspect of the invention described herein relates to a vector comprising any one of the polynucleotides encoding bispecific antibodies described herein.

Another aspect of the invention described herein relates to a host cell comprising any one of the vectors (e.g., vectors comprising any one of the polynucleotides encoding bispecific antibodies described herein). In one embodiment, the host cell is a mammalian cell. In one embodiment, the mammalian cell is a Chinese hamster ovary (CHO) cell. In another embodiment, the host cell is a prokaryotic cell. In one embodiment, the prokaryotic cell is *E. coli*.

Another aspect of the invention described herein relates to a method of producing a bispecific antibody that specifically binds TACI and CD3, the method comprising culturing any one of the host cells described herein (e.g., a host cell comprising any one of the vectors (e.g., vectors comprising any one of the polynucleotides encoding bispecific antibodies described herein)) in a culture medium.

In one embodiment, the method further comprises recovering the bispecific antibody from the host cell or the culture medium.

Another aspect of the invention described herein relates to a method of treating a disease or disorder in a subject in need thereof, wherein the method comprises administering to the subject one or more of the following: (i) any one of the CAR polypeptides described herein, any one of the polynucleotides described herein, and/or any one of the mammalian cells described herein; (ii) any one of the antibodies described herein; (iii) any one of the antibody-drug conjugates described herein; and (iv) any one of the bispecific antibodies described herein.

In one embodiment, the disease or disorder is a cancer, an autoimmune disorder, or a plasma cell disease or disorder.

In one embodiment, the disease or disorder is cancer.

In one embodiment, the cancer comprises cells expressing TACI.

In one embodiment, the cancer is multiple myeloma.

In one embodiment, the subject is resistant to anti-BCMA therapy.

In one embodiment, the disease or disorder is an autoimmune disease or disorder.

In one embodiment, the autoimmune disease or disorder is characterized by a high titer of antibodies contributing to the autoimmune disorder.

In one embodiment, the autoimmune disease or disorder is transplant rejection, graft versus host disease, or hemophilia with Factor inhibitors.

In one embodiment, the disease or disorder is a plasma cell disease or disorder.

In one embodiment, the plasma cell disease or disorder is plasma cell dyscrasias, plasmacytoma, plasma cell leukemia, multiple myeloma, Waldenstrom's macroglobulinemia, solitary plasmacytoma, extramedullary plasmacytoma, osteosclerotic myeloma, heavy chain diseases, monoclonal gammopathy of undetermined significance, and smoldering multiple myeloma.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19$^{th}$ Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of each of which are all incorporated by reference herein in their entireties.

In some embodiments, "activation" can refer to the state of a T cell that has been sufficiently stimulated to induce detectable cellular proliferation. In some embodiments, activation can refer to induced cytokine production. In other embodiments, activation can refer to detectable effector functions. At a minimum, an "activated T cell" as used herein is a proliferative T cell.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (K$_D$). Affinity can be measured by common methods known in the art, including those described herein. Specific illustrative and exemplary embodiments for measuring binding affinity are described below.

As used herein, "administering" is meant a method of giving a dosage of a compound (e.g., an anti-TACI antibody, antibody-drug conjugate, a BiTE, and/or an anti-TACI CAR) or a composition (e.g., a pharmaceutical composition, e.g., a pharmaceutical composition including an anti-TACI antibody, antibody-drug conjugate, a BiTE, and/or an anti-TACI CAR) to a subject. The compositions utilized in the methods described herein can be administered or formulated for administration, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated). Preferably, the compound (e.g., an anti-TACI antibody, antibody-drug conjugate, BiTE, and/or anti-TACI CAR of the invention) or composition (e.g., pharmaceutical composition comprising the an anti-TACI antibody, antibody-drug conjugate, BiTE, and/or anti-TACI CAR) is administered orally or formulated for oral administration.

The terms "anti-TACI antibody," "an antibody that binds to TACI," and "an antibody that specifically binds to TACI" refer to an antibody that is capable of binding TACI with sufficient affinity such that the antibody is useful as a preventative, diagnostic, and/or therapeutic agent in targeting TACI. In one embodiment, the extent of binding of an anti-TACI antibody to an unrelated, non-TACI protein is less than about 10% of the binding of the antibody to TACI as measured, e.g., by a radioimmunoassay (RIA). In certain embodiments, an antibody that binds to TACI has a dissociation constant (K$_D$) of ≤1 μM, ≤100 nM, ≤10 nM, ≤1 nM, ≤0.1 nM, ≤0.01 nM, or ≤0.001 nM (e.g. 10$^{-8}$M or less, e.g. from 10$^{-8}$M to 10$^{-13}$ M, e.g., from 10$^{-9}$M to 10$^{-13}$ M).

The term "antibody" as used herein in the broadest sense encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody" can refer, for example, to a glycoprotein comprising at least two heavy chains (HCs) and two light chains (LCs) inter-connected by disulfide bonds, or an antigen binding portion thereof. Each heavy chain is comprised of a heavy chain variable region (VH) and a heavy chain constant region (CH). The heavy chain constant region may be comprised of three domains, CH1, CH2, and/or CH3. Each light chain is comprised of a light chain variable region (VL) and a light chain constant region (CL). The VH and VL regions can be further subdivided into regions of hypervariability, termed "complementarity determining regions" (CDRs), interspersed with regions that are more conserved, termed "framework regions" (FRs). Each VH and VL may be composed, for example, of three CDRs and four FRs, arranged from amino-terminus to carboxyl-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An "antibody fragment" refers to a molecule other than an intact antibody that comprises a portion of an intact antibody that specifically binds to the antigen (e.g., TACI) to which the intact antibody binds. Examples of antibody fragments include, but are not limited to, Fv, Fab, Fab', Fab'-SH, $F(ab')_2$; diabodies; linear antibodies; single-chain antibody molecules (e.g., scFv); and multispecific antibodies formed from antibody fragments. These antibody fragments are obtained using conventional techniques, and the fragments are screened for utility in the same manner as are intact antibodies. Antibody fragments can be produced by recombinant DNA techniques, or by enzymatic or chemical cleavage of intact immunoglobulins.

By "bispecific T cell engagers," "BiTE antibody constructs," or "BiTEs" is meant polypeptides that each include tandemly linked single-chain variable fragments (scFvs). Optionally, the scFvs are linked by a linker (e.g., a glycine-rich linker). One scFv of the BiTE binds to the T cell receptor (TCR) (e.g., to the CD3ε subunit) and the other binds to a target antigen (e.g., a tumor-associated antigen).

As used herein, the term "chimeric" refers to the product of the fusion of portions of at least two or more different polynucleotide molecules. In one embodiment, the term "chimeric" refers to a gene expression element produced through the manipulation of known elements or other polynucleotide molecules.

The terms "chimeric antigen receptor" or "CAR" or "CARs" as used herein refer to engineered T cell receptors, which graft a ligand or antigen specificity onto T cells (for example, naïve T cells, central memory T cells, effector memory T cells or combinations thereof). CARs are also known as artificial T-cell receptors, chimeric T-cell receptors or chimeric immunoreceptors. As used herein, a "CAR T cell" or "CAR-T" refers to a T cell that expresses a CAR. When expressed in a T cell, CARs have the ability to redirect T-cell specificity and reactivity toward a selected target in a non-MHC-restricted manner, for example, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape.

A "co-stimulatory ligand," as the term is used herein, includes a molecule on an antigen presenting cell (APC) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, 4-1BBL, OX40L, CD7, B7-1 (CD80), B7-2 (CD86), PD-L1, PD-L2, inducible COStimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll-like receptor and a ligand that specifically binds with B7-H3. A co-stimulatory ligand also can include, but is not limited to, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83. Other co-stimulatory ligands known in the art may be employed according to standard methods as well.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA, a Toll-like receptor, CD27, CD28, 4-1BB, OX40, CD30, CD40, PD-1, ICOS, lymphocyte function-associated antigen-1 (LFA-1), CD2, CD7, LIGHT, NKG2C, B7-H3, and CD83.

The terms "decrease," "reduced," "reduction," or "inhibit" refer to a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. Typically, such a decrease is statistically significant. As used herein, "reduction" or "inhibition" does not encompass a complete inhibition or reduction as compared to a reference level. "Complete inhibition" is a 100% inhibition as compared to a reference level. Where applicable, a decrease can be preferably down to a level accepted as within the range of normal for an individual without a given disorder.

A "disease" is a state of health of an animal, for example, a human, wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "EC50," as used herein, refers to the concentration of an antibody or an antigen-binding portion thereof, which induces a response, either in an in vivo or an in vitro assay, which is 50% of the maximal response (i.e., halfway between the maximal response and the baseline).

The terms "effective amount," "effective dose," and "effective dosage" as used herein are defined as an amount sufficient to achieve, or at least partially achieve, the desired effect. The term "therapeutically effective dose" or "therapeutically effective amount" is defined as an amount sufficient to prevent, cure, or at least partially arrest, the disease (e.g., diarrhea) and its complications in a patient already suffering from the disease or at risk of developing the disease. Amounts effective for this use will depend upon the severity of the disorder being treated and the general state of the patient's own immune system.

The term "engineered" and its grammatical equivalents as used herein, in some embodiments, can refer to one or more human-designed alterations of a nucleic acid, e.g., the nucleic acid within an organism's genome. In another embodiment, engineered can refer to alterations, additions, and/or deletion of genes. An "engineered cell" can refer to a cell with an added, deleted and/or altered gene. The term "cell" or "engineered cell" and their grammatical equivalents as used herein can refer to a cell of human or non-human animal origin.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, X-ray crystallography and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., TACI), which affect the binding of the antibody (e.g., monoclonal antibody).

The terms "full-length antibody," "intact antibody," and "whole antibody" are used herein interchangeably to refer to an antibody having a structure substantially similar to a native antibody structure or having heavy chains that contain an Fc region as defined herein.

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "human antibody" includes antibodies having variable and constant regions (if present) of human germline immunoglobulin sequences. Human antibodies can include amino acid residues not encoded by human germline immunoglobulin sequences (e.g., mutations introduced by random or site-specific mutagenesis in vitro or by somatic mutation in vivo) (see, Lonberg, N. et al. (1994) Nature 368(6474): 856-859); Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). However, the term "human antibody" does not include antibodies in which CDR sequences derived from the germline of another mammalian species, such as a mouse, have been grafted onto human framework sequences (i.e., humanized antibodies).

An "isolated antibody" is one which has been identified and separated and/or recovered from a component of its natural environment and/or is substantially free of other antibodies having different antigenic specificities (e.g., an isolated antibody that specifically binds to TACI is substantially free of antibodies that specifically bind antigens other than TACI). Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie™ blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step.

The term "$K_D$," as used herein, is intended to refer to the dissociation equilibrium constant of a particular antibody-antigen interaction. Typically, the antibodies bind to TACI with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology in a BIA-CORE 3000 instrument using recombinant TACI as the analyte and the antibody as the ligand.

The term "monoclonal antibody," as used herein, refers to an antibody which displays a single binding specificity and affinity for a particular epitope. Accordingly, the term "human monoclonal antibody," or "HuMab," refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

In some embodiments, a polypeptide described herein (or a nucleic acid encoding such a polypeptide) can be a functional fragment of one of the amino acid sequences described herein. As used herein, a "functional fragment" is a fragment or segment of a peptide that retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions, or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan. For instance, a variant amino acid or DNA sequence can be at least 80%, at least 85%, at least 90%, at least 91%, at least 92%, at least 93%, at least 94%, at least 95%, at least 96%, at least 97%, at least 98%, at least 99%, or more, identical to a native or reference sequence.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the term "DNA" is defined as deoxyribonucleic acid. The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g., a CAR polypeptide) is included in a vector, for example, in an expression vector. In some of the aspects described herein, a nucleic acid sequence encoding a given polypeptide as described herein is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression, for example, of an RNA or polypeptide from sequences linked to transcriptional regulatory sequences on the vector. The sequences expressed will often, but not necessarily, be heterologous to the cell. An expression vector may include additional elements, for example, the expression vector may have two replication systems, thus allowing it to be maintained in two organisms, for example, in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra-chromosomal DNA thereby eliminating potential effects of chromosomal integration.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the terms "specific binding" and "specifically binds" refer to a physical interaction between two molecules, compounds, cells and/or particles wherein the first entity binds to the second, target, entity with greater specificity and affinity than it binds to a third entity which is a non-target. In some embodiments, specific binding can refer to an affinity of the first entity for the second target, entity, which is at least 10 times, at least 50 times, at least 100 times, at least 500 times, at least 1000 times or more greater than the affinity for the third non-target entity under the same conditions. A reagent specific for a given target is one that exhibits specific binding for that target under the conditions of the assay being utilized. A non-limiting example includes an antibody, or a ligand, which recognizes and binds with a cognate binding partner (for example, a stimulatory and/or costimulatory molecule present on a T cell) protein. For example, a specifically antibody may bind to its target with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument, which can be performed, for example, using recombinant TACI as the analyte and the antibody as the ligand. In some embodiments, binding by the antibody to the predetermined antigen is with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, a "signal peptide" or "signal sequence" refers to a peptide at the N-terminus of a newly synthesized protein that serves to direct a nascent protein into the endoplasmic reticulum. In some embodiments, the signal peptide is a CD8 signal peptide.

A "stimulatory ligand," as used herein, refers to a ligand that when present on an antigen presenting cell (APC) (e.g., a macrophage, a dendritic cell, a B-cell, an artificial APC, and the like) can specifically bind with a cognate binding partner (referred to herein as a "stimulatory molecule" or "co-stimulatory molecule") on a T cell, thereby mediating a primary response by the T cell, including, but not limited to, proliferation, activation, initiation of an immune response, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell.

A "subject" or an "individual" is a mammal. Mammals include, but are not limited to, domesticated animals (e.g., cows, sheep, cats, dogs, and horses), primates (e.g., humans and non-human primates such as monkeys), rabbits, deer, and rodents (e.g., mice and rats). In certain embodiments, the subject or individual is a human.

A subject can be one who has been previously diagnosed with or identified as suffering from or having a condition in need of treatment (e.g., the diseases and disorders described herein) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

The term "transmembrane activator and calcium modulator and cyclophilin ligand interactor," or "TACI" is also known as tumor necrosis factor receptor (TNFR) superfamily member 13B (TNFRSF13B) and is a lymphocyte-specific member of the TNFR superfamily. TACI interacts with two other members of the tumor necrosis factor (TNF) family, B cell activating factor (BAFF) and a proliferation-inducing ligand (APRIL), and controls T cell-independent B cell antibody responses, isotype switching, and B cell homeostasis.

As used herein, the terms "treat," "treatment," "treating," or "amelioration" refer to therapeutic treatments, wherein the object is to reverse, alleviate, ameliorate, inhibit, slow down, or stop the progression or severity of a condition associated with a disease or disorder, e.g., glioblastoma, glioma, acute lymphoblastic leukemia or other cancer, disease, or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side effects of the disease (including palliative treatment).

As used herein, the terms "tumor antigen" and "cancer antigen" are used interchangeably to refer to antigens that are differentially expressed by cancer cells and can thereby be exploited in order to target cancer cells. Cancer antigens are antigens that can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses.

Other terms are defined within the description of the various aspects and embodiments of the technology, as set forth below.

The constructs and methods described herein provide several advantages. For example, one advantage provided by the anti-TACI antibodies, antibody-drug conjugates, BiTEs, and anti-TACI CARs described herein is that targeting TACI allows for mitigation of the problem of BCMA antigen escape. While anti-BCMA therapies have produced promising results thus far for multiple myeloma, targeting BCMA has also been shown to lead to relapse and/or BCMA antigen loss following BCMA CAR T cell treatment. While the frequency of this occurrence has not yet been defined, it was recently observed in a study that the overall objective response rate was 85%, yet the median progression free survival was 11.8 months (Raje et al., *N Engl J Med.* 2019; 380(18):1726-1737), indicating that monospecific targeting of BCMA with CAR T cells may not be curative therapy for most patients. Reports of disease resistance due to BCMA antigen loss under the selective pressure of anti-BCMA CAR T cell treatment are also emerging. Thus, targeting TACI provides a distinctive advantage when treating diseases affected by BCMA antigen escape.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 19 is a graph showing survival proportions of mice after treatment with UTD, anti-BCMA, anti-TACI (H/L), and anti-TACI (L/H) CAR T cells.

FIG. 20A shows construct design of anti-TACI and control anti-BCMA CARs. FIG. 20B shows BCMA and TACI staining. FIG. 20C shows luciferase-based killing assays of anti-TACI CARs and anti-BCMA CAR (control) against the multiple myeloma cell lines MM1S, RPM1-8266, and U266. FIG. 20D shows in vivo luciferase imaging post-CAR treatment of MM1S. FIG. 20E shows binding of soluble TACI to BCMA and TACI CARs.

FIG. 21A shows dual-targeting CAR T cell construct design. FIG. 21B shows transduction efficiency of constructs. FIG. 21C shows luciferase based killing assays of dual-targeting CARs against multiple myeloma cell lines MM1S, RPM1-8226, and U266. FIG. 21D shows expression of BCMA and TACI on MM1S cells that express non-specific CRISPR/Cas9, CRISPR/Cas9 targeting BCMA, and CRISPR/Cas9 targeting TACI. FIG. 21E shows Luciferase based killing assays against the MM1S knockout cell lines from FIG. 21D in flat bottom plates.

FIG. 26A shows a timeline of the experiment. FIGS. 26B-26F show individual growth curves of RPMI8226 tumors in mice treated with anti-TACI H-L CAR (FIG. 26B), anti-TACI L-H CAR (FIG. 26C), anti-BCMA CAR (FIG. 26D), or untransduced T cells (FIG. 26E, negative control), or untreated (FIG. 26F, negative control). FIG. 26G shows survival of mice over time. FIG. 26H shows number of CAR T cells per microliter in the blood of mice 21 days after intravenous administration of $2 \times 10^6$ CAR T cells.

FIG. 27A shows flow cytometry analysis of MM1S Cas9 cancer cells, with or without TACI disrupted by Cas9, and stained for TACI and BCMA. FIG. 27B shows cytotoxicity of MM1S Cas9 and MM1S Cas9 TACI knockout resulting from co-incubation with anti-TACI H-L CAR, anti-TACI L-H CAR, anti-BCMA CAR, or untransduced T cells at various ratios of T cells to cancer cells.

FIG. 30A shows a timeline of the experiment, in which $1 \times 10^6$ MM1S cells were injected intravenously into mice at day −14, then $2 \times 10^6$ CAR T cells were injected intravenously at day 0, and bioluminescence imaging measurements were conducted at days 0, 4, 7, 11, and 14. FIGS. 30B, 30C, and 30D show bioluminescent flux from MM1S cells measured in mice untreated or treated with T cells (transduced with anti-TACI/anti-BCMA bispecific CAR or anti-BCMA/anti-TACI bispecific CAR, or untransduced) from three different donors. FIG. 30E show representative bioluminescent images from mice treated with cells from donor 1.

FIG. 31A shows a timeline of the experiment, in which $5 \times 10^6$ RPMI8226 cells were implanted subcutaneously into mice at day −14, then $2 \times 10^6$ CART cells were injected intravenously at day 0, and caliper measurements of the tumors were conducted at days 0, 4, 7, 10, and 14. FIG. 31B shows number of CAR T cells per microliter in the blood of mice on days 14 (left) and 21 (right). FIGS. 31C, 31D, 31E, and 31F show tumor volume curves measured in mice treated with anti-TACI/anti-BCMA bispecific CAR (FIG. 31C), anti-BCMA/anti-TACI bispecific CAR (FIG. 31D), or untransduced (FIG. 31E) T cells, or untreated (FIG. 31F).

FIG. 32A shows a timeline of the experiment, in which $1 \times 10^6$ T cells (untransduced or transduced with anti-BCMA CAR, anti-TACI/anti-BCMA bispecific CAR, or anti-BCMA/anti-TACI bispecific CAR) were stimulated with irradiated K562 cells overexpressing BCMA at day 0, and flow cytometric analysis was conducted on days 0, 7, 14, 21, and 28 to monitor exhaustion and memory phenotypes. T cells were counted at each time point, re-normalized to $1 \times 10^6$ cells, and restimulated. FIG. 32B shows results of flow cytometry measurements of Tim-3 and Lag3 on T cells over time.

FIG. 33A shows a timeline of the experiment, in which $1 \times 10^6$ CAR T cells were stimulated with irradiated K562 cells overexpressing BCMA at day 0, and counted and analyzed by flow cytometry on days 0, 7, 14, and 21. CAR T cells were restimulated on days 7 and 14. FIG. 33B shows percentages of each type of CAR T cell (anti-BCMA, anti-TACI/anti-BCMA bispecific, or anti-BCMA/anti-TACI bispecific) categorized by flow cytometry into each effector phenotype, according to the definitions shown on the left (central memory (CM): CCR7$^+$ CD45RA$^-$; effector memory (EM): CCR7$^-$ CD45RA$^-$; naïve: CCR7$^+$ CD45RA$^+$; terminally differentiated effector (TDE): CCR7$^-$ CD45RA$^+$). FIG. 33C shows growth of the CAR T cells over time, as number of cells/$10^6$.

DETAILED DESCRIPTION OF CERTAIN EMBODIMENTS

Figure 1:
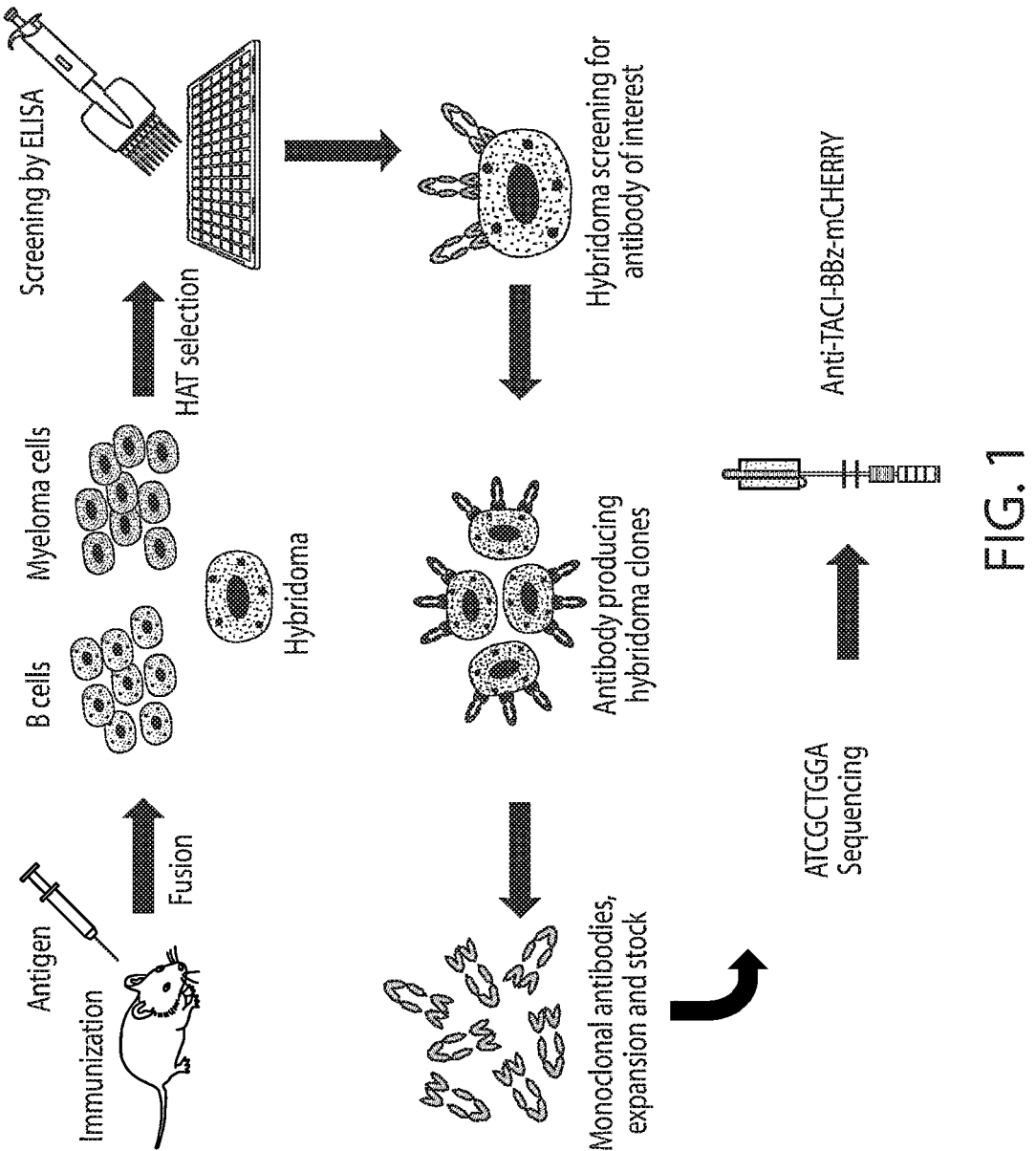
FIG. 1 is a diagram showing the general methods used for generating the anti-transmembrane activator and calcium modulator and cyclophilin ligand interactor (TACI) antibodies and its use in the anti-TACI chimeric antigen receptor (CAR) T cells described herein.

Provided herein are anti-transmembrane activator and calcium modulator and cyclophilin ligand interactor (TACI) antibodies, antibody-drug conjugates thereof, bispecific T cell engagers (BiTEs) that target TACI, and anti-TACI chimeric antigen receptors (CARs). Such antibodies, antibody-drug conjugates, BiTEs, and CARs can be used, e.g., in methods for treating a cancer, an autoimmune disorder, or a plasma cell disease or disorder in a subject in need thereof.

Anti-TACI Antibodies

The invention provides isolated antibodies that specifically bind to TACI.

The present disclosure, in some aspects, provide heavy chain and light chain variable domain sequences, and the heavy chain and light chain CDR sequences of the anti-TACI antibodies described herein. The CDRs of an antibody may have different amino acid sequences when different definition systems are used (e.g., the IMGT definition, the Kabat definition, or the Chothia definition). A definition system annotates each amino acid in a given antibody sequence (e.g., VH or VL sequence) with a number, and numbers corresponding to the heavy chain and light chain CDRs are provided in Table 3. CDR sequences of examples of anti-TACI antibodies according to the different definition systems are provided in Table 4.

In some embodiments, the anti-TACI antibodies of the present disclosure comprises one or more of the CDR-H (e.g., CDR-H1, CDR-H2, and CDR-H3) amino acid sequences from any one of the anti-TACI antibodies selected from Table 4. In some embodiments, the anti-TACI antibodies of the present disclosure comprise the CDR-H1, CDR-H2, and CDR-H3 as provided for each numbering system provided in Table 4. In some embodiments, the anti-TACI antibodies of the present disclosure comprises one or more of the CDR-L (e.g., CDR-L1, CDR-L2, and CDR-L3) amino acid sequences from any one of the anti-TACI antibodies selected from Table 4. In some embodiments, the anti-TACI antibodies of the present disclosure comprise the CDR-L1, CDR-L2, and CDR-L3 as provided for teach numbering system provided in Table 4.

In some embodiments, the anti-TACI antibodies of the present disclosure comprise the CDR-H1, CDR-H2, CDR-H3, CDR-L1, CDR-L2, and CDR-L3 as provided for each numbering system in Table 4. In some embodiments, antibody heavy and light chain CDR3 domains may play a particularly important role in the binding specificity/affinity of an antibody for an antigen. Accordingly, the anti-TACI antibodies of the disclosure may include at least the heavy and/or light chain CDR3s of any one of the anti-TACI antibody provided in Table 4.

In some embodiments, the anti-TACI antibody of the present disclosure comprises a CDR-H1, a CDR-H2, and a CDR-H3 of a heavy chain variable domain having the amino acid sequence of SEQ ID NO: 1. Alternatively or in addition, the anti-TACI antibody of the present disclosure comprises a CDR-L1, a CDR-L2, and a CDR-L3 of a light chain variable domain having the amino acid sequence of SEQ ID NO: 2.

In some embodiments, the anti-TACI antibody of the present disclosure comprises a CDR-H1 having the amino acid sequence of SEQ ID NO: 26 (according to the IMGT definition system), a CDR-H2 having the amino acid sequence of SEQ ID NO: 27 (according to the IMGT definition system), a CDR-H3 having the amino acid sequence of SEQ ID NO: 28 (according to the IMGT definition system), a CDR-L1 having the amino acid sequence of SEQ ID NO: 29 (according to the IMGT definition system), a CDR-L2 having the amino acid sequence of SEQ ID NO: 30 (according to the IMGT definition system), and a CDR-L3 having the amino acid sequence of SEQ ID NO: 31 (according to the IMGT definition system).

In some embodiments, anti-TACI antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1 having the amino acid sequence of SEQ ID NO: 26, CDR-H2 having the amino acid sequence of SEQ ID NO: 27, and CDR-H3 having the amino acid sequence of SEQ ID NO: 28. "Collectively" means that the total number of amino acid variations in all of the three heavy chain CDRs is within the defined range. Alternatively or in addition, the anti-TACI antibody of the present disclosure comprises a CDR-L1, a CDR-L2, and a CDR-L3, which collectively contains no more than 5 amino acid variations (e.g., no more than 5, 4, 3, 2 or 1 amino acid variation) as compared with the CDR-L1 having the amino acid sequence of SEQ ID NO: 29, CDR-L2 having the amino acid sequence of SEQ ID NO: 30, and CDR-L3 having the amino acid sequence of SEQ ID NO: 31.

In some embodiments, the anti-TACI antibody of the present disclosure comprises a CDR-H1, a CDR-H2, and a CDR-H3 that collectively are at least 80% (e.g., 80%, 85%, 90%, 95%, 98%, or 99%) identical to the CDR-H1 having the amino acid sequence of SEQ ID NO: 26, CDR-H2 having the amino acid sequence of SEQ ID NO: 27, and CDR-H3 having the amino acid sequence of SEQ ID NO: 28. Alternatively or in addition, the anti-TACI antibody of the present disclosure comprises a CDR-L1, a CDR-L2, and a CDR-L3 that collectively are at least 80% (e.g., 80%, 85%, 90%, 95%, 98%, or 99%) identical to the to the CDR-L1 having the amino acid sequence of SEQ ID NO: 29, CDR-L2 having the amino acid sequence of SEQ ID NO: 30, and CDR-L3 having the amino acid sequence of SEQ ID NO: 31.

In some embodiments, the anti-TACI antibody of the present disclosure comprises: a CDR-H1 having no more than 3 amino acid variations (e.g., no more than 3, 2, or 1 amino acid variation) as compared with the CDR-H1 having the amino acid sequence of SEQ ID NO: 26; a CDR-H2 having no more than 3 amino acid variations (e.g., no more than 3, 2, or 1 amino acid variation) as compared with the CDR-H2 having the amino acid sequence of SEQ ID NO: 27; and/or a CDR-H3 having no more than 3 amino acid variations (e.g., no more than 3, 2, or 1 amino acid variation) as compared with the CDR-H3 having the amino acid sequence of SEQ ID NO: 28. Alternatively or in addition, the anti-TACI antibody of the present disclosure comprises: a CDR-L1 having no more than 3 amino acid variations (e.g., no more than 3, 2, or 1 amino acid variation) as compared with the CDR-L1 having the amino acid sequence of SEQ ID NO: 29; a CDR-L2 having no more than 3 amino acid variations (e.g., no more than 3, 2, or 1 amino acid variation) as compared with the CDR-L2 having the amino acid sequence of SEQ ID NO: 30; and/or a CDR-L3 having no more than 3 amino acid variations (e.g., no more than 3, 2, or 1 amino acid variation) as compared with the CDR-L3 having the amino acid sequence of SEQ ID NO: 31.

In some embodiments, the anti-TACI antibody of the present disclosure comprises a CDR-H1 having the amino acid sequence of SEQ ID NO: 32 (according to the Kabat definition system), a CDR-H2 having the amino acid sequence of SEQ ID NO: 33 (according to the Kabat definition system), a CDR-H3 having the amino acid sequence of SEQ ID NO: 34 (according to the Kabat definition system), a CDR-L1 having the amino acid sequence of SEQ ID NO: 35 (according to the Kabat definition system), a CDR-L2 having the amino acid sequence of SEQ ID NO: 36 (according to the Kabat definition system), and a CDR-L3 having the amino acid sequence of SEQ ID NO: 31 (according to the Kabat definition system).

In some embodiments, anti-TACI antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1 having the amino acid sequence of SEQ ID NO: 32, CDR-H2 having the amino acid sequence of SEQ ID NO: 33, and CDR-H3 having the amino acid sequence of SEQ ID NO: 34. "Collectively" means that the total number of amino acid variations in all of the three heavy chain CDRs is within the defined range. Alternatively or in addition, the anti-TACI antibody of the present disclosure comprises a CDR-L1, a CDR-L2, and a CDR-L3, which collectively contains no more than 5 amino acid variations (e.g., no more than 5, 4, 3, 2 or 1 amino acid variation) as compared with the CDR-L1 having the amino acid sequence of SEQ ID NO: 35, CDR-L2 having the amino acid sequence of SEQ ID NO: 36, and CDR-L3 having the amino acid sequence of SEQ ID NO: 31.

In some embodiments, the anti-TACI antibody of the present disclosure comprises a CDR-H1, a CDR-H2, and a CDR-H3 that collectively are at least 80% (e.g., 80%, 85%, 90%, 95%, 98%, or 99%) identical to the CDR-H1 having the amino acid sequence of SEQ ID NO:32, CDR-H2 having the amino acid sequence of SEQ ID NO: 33, and CDR-H3 having the amino acid sequence of SEQ ID NO: 34. Alternatively or in addition, the anti-TACI antibody of the present disclosure comprises a CDR-L1, a CDR-L2, and a CDR-L3 that collectively are at least 80% (e.g., 80%, 85%, 90%, 95%, 98%, or 99%) identical to the to the CDR-L1 having the amino acid sequence of SEQ ID NO: 35, CDR-L2 having the amino acid sequence of SEQ ID NO: 36, and CDR-L3 having the amino acid sequence of SEQ ID NO: 31.

In some embodiments, the anti-TACI antibody of the present disclosure comprises: a CDR-H1 having no more than 3 amino acid variations (e.g., no more than 3, 2, or 1 amino acid variation) as compared with the CDR-H1 having the amino acid sequence of SEQ ID NO: 32; a CDR-H2 having no more than 3 amino acid variations (e.g., no more than 3, 2, or 1 amino acid variation) as compared with the CDR-H2 having the amino acid sequence of SEQ ID NO: 33; and/or a CDR-H3 having no more than 3 amino acid variations (e.g., no more than 3, 2, or 1 amino acid variation) as compared with the CDR-H3 having the amino acid sequence of SEQ ID NO: 34. Alternatively or in addition, the anti-TACI antibody of the present disclosure comprises: a CDR-L1 having no more than 3 amino acid variations (e.g., no more than 3, 2, or 1 amino acid variation) as compared with the CDR-L1 having the amino acid sequence of SEQ ID NO: 35; a CDR-L2 having no more than 3 amino acid variations (e.g., no more than 3, 2, or 1 amino acid variation) as compared with the CDR-L2 having the amino acid sequence of SEQ ID NO: 36; and/or a CDR-L3 having no more than 3 amino acid variations (e.g., no more than 3, 2, or 1 amino acid variation) as compared with the CDR-L3 having the amino acid sequence of SEQ ID NO: 31.

In some embodiments, the anti-TACI antibody of the present disclosure comprises a CDR-H1 having the amino acid sequence of SEQ ID NO: 37 (according to the Chothia definition system), a CDR-H2 having the amino acid sequence of SEQ ID NO: 38 (according to the Chothia definition system), a CDR-H3 having the amino acid sequence of SEQ ID NO: 39 (according to the Chothia definition system), a CDR-L1 having the amino acid sequence of SEQ ID NO: 40 (according to the Chothia definition system), a CDR-L2 having the amino acid sequence of SEQ ID NO: 30 (according to the Chothia definition system), and a CDR-L3 having the amino acid sequence of SEQ ID NO: 41 (according to the Chothia definition system).

In some embodiments, anti-TACI antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1 having the amino acid sequence of SEQ ID NO: 37, CDR-H2 having the amino acid sequence of SEQ ID NO: 38, and CDR-H3 having the amino acid sequence of SEQ ID NO: 39. "Collectively" means that the total number of amino acid variations in all of the three heavy chain CDRs is within the defined range. Alternatively or in addition, the anti-TACI antibody of the present disclosure comprises a CDR-L1, a CDR-L2, and a CDR-L3, which collectively contains no more than 5 amino acid variations (e.g., no more than 5, 4, 3, 2 or 1 amino acid variation) as compared with the CDR-L1 having the amino acid sequence of SEQ ID NO: 40, CDR-L2 having the amino acid sequence of SEQ ID NO: 30, and CDR-L3 having the amino acid sequence of SEQ ID NO: 41.

In some embodiments, the anti-TACI antibody of the present disclosure comprises a CDR-H1, a CDR-H2, and a CDR-H3 that collectively are at least 80% (e.g., 80%, 85%, 90%, 95%, 98%, or 99%) identical to the CDR-H1 having the amino acid sequence of SEQ ID NO: 37, CDR-H2 having the amino acid sequence of SEQ ID NO: 38, and CDR-H3 having the amino acid sequence of SEQ ID NO: 39. Alternatively or in addition, the anti-TACI antibody of the present disclosure comprises a CDR-L1, a CDR-L2, and a CDR-L3 that collectively are at least 80% (e.g., 80%, 85%, 90%, 95%, 98%, or 99%) identical to the to the CDR-L1 having the amino acid sequence of SEQ ID NO: 40, CDR-L2 having the amino acid sequence of SEQ ID NO: 30, and CDR-L3 having the amino acid sequence of SEQ ID NO: 41.

In some embodiments, the anti-TACI antibody of the present disclosure comprises: a CDR-H1 having no more than 3 amino acid variations (e.g., no more than 3, 2, or 1 amino acid variation) as compared with the CDR-H1 having the amino acid sequence of SEQ ID NO: 37; a CDR-H2 having no more than 3 amino acid variations (e.g., no more than 3, 2, or 1 amino acid variation) as compared with the CDR-H2 having the amino acid sequence of SEQ ID NO: 38; and/or a CDR-H3 having no more than 3 amino acid variations (e.g., no more than 3, 2, or 1 amino acid variation) as compared with the CDR-H3 having the amino acid sequence of SEQ ID NO: 39. Alternatively or in addition, the anti-TACI antibody of the present disclosure comprises: a CDR-L1 having no more than 3 amino acid variations (e.g., no more than 3, 2, or 1 amino acid variation) as compared with the CDR-L1 having the amino acid sequence of SEQ ID NO: 40; a CDR-L2 having no more than 3 amino acid variations (e.g., no more than 3, 2, or 1 amino acid variation) as compared with the CDR-L2 having the amino acid sequence of SEQ ID NO: 30; and/or a CDR-L3 having no more than 3 amino acid variations (e.g., no more than 3, 2, or 1 amino acid variation) as compared with the CDR-L3 having the amino acid sequence of SEQ ID NO: 41.

In some embodiments, the anti-TACI antibody of the present disclosure comprises a VH comprising the amino acid sequence of SEQ ID NO: 1. Alternatively or in addition, the anti-TACI antibody of the present disclosure comprises a VL comprising the amino acid sequence of SEQ ID NO: 2.

In some embodiments, the anti-TACI antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 1. Alternatively or in addition, the anti-TACI antibody of the present disclosure comprises a VL containing no more than 20 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 2.

In some embodiments, the anti-TACI antibody of the present disclosure comprises a VH comprising an amino acid sequence that is at least 80% (e.g., 80%, 85%, 90%, 95%, 98%, or 99%) identical to the VH as set forth in SEQ ID NO: 1. Alternatively or in addition, the anti-TACI antibody of the present disclosure comprises a VL comprising an amino acid sequence that is at least 80% (e.g., 80%, 85%, 90%, 95%, 98%, or 99%) identical to the VL as set forth in SEQ ID NO: 2.

In some embodiments, the anti-TACI antibody of the present disclosure is a humanized antibody. In some embodiments, the humanized anti-TACI antibody comprises a humanized VH comprising a CDR-H1 having the amino acid sequence of SEQ ID NO: 26 (according to the IMGT definition system), a CDR-H2 having the amino acid sequence of SEQ ID NO: 27 (according to the IMGT definition system), a CDR-H3 having the amino acid sequence of SEQ ID NO: 28 (according to the IMGT definition system); and a humanized VL comprising a CDR-L1 having the amino acid sequence of SEQ ID NO: 29 (according to the IMGT definition system), a CDR-L2 having the amino acid sequence of SEQ ID NO: 30 (according to the IMGT definition system), and a CDR-L3 having the amino acid sequence of SEQ ID NO: 31 (according to the IMGT definition system).

In some embodiments, the humanized anti-TACI antibody comprises a humanized VH comprising a CDR-H1 having the amino acid sequence of SEQ ID NO: 32 (according to the Kabat definition system), a CDR-H2 having the amino acid sequence of SEQ ID NO: 33 (according to the Kabat definition system), a CDR-H3 having the amino acid sequence of SEQ ID NO: 34 (according to the Kabat definition system), a CDR-L1 having the amino acid sequence of SEQ ID NO: 35 (according to the Kabat definition system), a CDR-L2 having the amino acid sequence of SEQ ID NO: 36 (according to the Kabat definition system), and a CDR-L3 having the amino acid sequence of SEQ ID NO: 31 (according to the Kabat definition system).

In some embodiments, the humanized anti-TACI antibody comprises a humanized VH comprising a CDR-H1 having the amino acid sequence of SEQ ID NO: 37 (according to the Chothia definition system), a CDR-H2 having the amino acid sequence of SEQ ID NO: 38 (according to the Chothia definition system), a CDR-H3 having the amino acid sequence of SEQ ID NO: 39 (according to the Chothia definition system), a CDR-L1 having the amino acid sequence of SEQ ID NO: 40 (according to the Chothia definition system), a CDR-L2 having the amino acid sequence of SEQ ID NO: 30 (according to the Chothia definition system), and a CDR-L3 having the amino acid sequence of SEQ ID NO: 41 (according to the Chothia definition system).

In some embodiments, the anti-TACI antibody is an IgG, a Fab fragment, a F(ab') fragment, a F(ab')$_2$ fragment, a scFv, or an scFv fused to a constant region (e.g., N- or C-terminal fusion). Non-limiting examples of anti-TACI antibodies in different formats are provided herein.

In some embodiments, the anti-TACI antibody is a single-chain fragment variable (scFv) comprising the VH and VL in a single polypeptide chain. In some embodiments, the scFv comprises any one of the heavy chain CDRs, light chain CDRs, VHs, and/or VLs described herein on a single polypeptide chain. In some embodiments, the scFv comprises the VH linked at the N-terminus of the VL. In some embodiments, the scFv comprises the VL linked at the N-terminus of the VH. In some embodiments, the VH and VL are linked via a linker (e.g., a polypeptide linker). Any polypeptide linker can be used for linking the VH and VL in the scFv. Selection of a linker sequence is within the abilities of those skilled in the art.

In some embodiments, the scFv comprises a VH comprising a CDR-H1 having the amino acid sequence of SEQ ID NO: 26 (according to the IMGT definition system), a CDR-H2 having the amino acid sequence of SEQ ID NO: 27 (according to the IMGT definition system), a CDR-H3 having the amino acid sequence of SEQ ID NO: 28 (according to the IMGT definition system); and a VL comprising a CDR-L1 having the amino acid sequence of SEQ ID NO: 29 (according to the IMGT definition system), a CDR-L2 having the amino acid sequence of SEQ ID NO: 30 (according to the IMGT definition system), and a CDR-L3 having the amino acid sequence of SEQ ID NO: 31 (according to the IMGT definition system), wherein the VH and VL are on a single polypeptide chain (e.g., linked via an amide bond or linked via a linker such as a peptide linker), and wherein the VH is linked to the N-terminus or the C-terminus of the VL. In some embodiments, the VH and VL are linked via a linker comprising the amino acid sequence of GGGGSGGGGSGGGGSGGGGS (SEQ ID NO: 3). In some embodiments, the scFv comprises the amino acid sequence of SEQ ID NO: 4 or SEQ ID NO: 5.

In some embodiments, the scFv comprises a VH comprising a CDR-H1 having the amino acid sequence of SEQ ID NO: 32 (according to the Kabat definition system), a CDR-H2 having the amino acid sequence of SEQ ID NO: 33 (according to the Kabat definition system), a CDR-H3 having the amino acid sequence of SEQ ID NO: 34 (according to the Kabat definition system); and a VL comprising a CDR-L1 having the amino acid sequence of SEQ ID NO: 35 (according to the Kabat definition system), a CDR-L2 having the amino acid sequence of SEQ ID NO: 36 (according to the Kabat definition system), and a CDR-L3 having the amino acid sequence of SEQ ID NO: 31 (according to the Kabat definition system), wherein the VH and VL are on a single polypeptide chain (e.g., linked via an amide bond or linked via a linker such as a peptide linker), and wherein the VH is linked to the N-terminus or the C-terminus of the VL. In some embodiments, the VH and VL are linked via a linker comprising the amino acid sequence of GGGGSGGGGSGGGGSGGGGS (SEQ ID NO: 3). In some embodiments, the scFv comprises the amino acid sequence of SEQ ID NO: 4 or SEQ ID NO: 5.

In some embodiments, the scFv comprises a VH comprising a CDR-H1 having the amino acid sequence of SEQ ID NO: 37 (according to the Chothia definition system), a CDR-H2 having the amino acid sequence of SEQ ID NO: 38 (according to the Chothia definition system), a CDR-H3 having the amino acid sequence of SEQ ID NO: 39 (according to the Chothia definition system); and a VL comprising a CDR-L1 having the amino acid sequence of SEQ ID NO: 40 (according to the Chothia definition system), a CDR-L2 having the amino acid sequence of SEQ ID NO: 30 (according to the Chothia definition system), and a CDR-L3 having the amino acid sequence of SEQ ID NO: 41 (according to the Chothia definition system), wherein the VH and VL are on a single polypeptide chain (e.g., linked via an amide bond or linked via a linker such as a peptide linker), and wherein the VH is linked to the N-terminus or the C-terminus of the VL. In some embodiments, the VH and VL are linked via a linker comprising the amino acid sequence of GGGGSGGGGSGGGGSGGGGS (SEQ ID NO: 3). In some embodiments, the scFv comprises the amino acid sequence of SEQ ID NO: 4 or SEQ ID NO: 5.

In some embodiments, the scFV comprises a VH comprising an amino acid sequence that is at least 80% (e.g., 80%, 85%, 90%, 95%, 98%, or 99%) identical to the VH as set forth in SEQ ID NO: 1 and a VL (e.g., a humanized VL) comprising an amino acid sequence that is at least 80% (e.g., 80%, 85%, 90%, 95%, 98%, or 99%) identical to the VL as set forth in SEQ ID NO: 2, wherein the VH and VL are in a single polypeptide chain (e.g., linked via an amide bond or linked via a linker such as a peptide linker), and wherein the VH is linked to the N-terminus or the C-terminus of the VL. In some embodiments, the VH and VL are linked via a linker comprising the amino acid sequence of GGGGSGGGGSGGGGSGGGGS (SEQ ID NO: 3). In some embodiments, the scFv comprises an amino acid sequence that has at least 80% (e.g., 80%, 85%, 90%, 95%, 98%, or 99%) identity with the amino acid sequence of SEQ ID NO: 4 or SEQ ID NO: 5.

In some embodiments, the scFV comprises a VH that contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 1, and a VL that contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VL as set forth in SEQ ID NO: 2, wherein the VH and VL are in a single polypeptide chain (e.g., linked via an amide bond or linked via a linker such as a peptide linker), and wherein the VH is linked to the N-terminus or the C-terminus of the VL. In some embodiments, the VH and VL are linked via a linker comprising the amino acid sequence of GGGGSGGGGSGGGGSGGGGS (SEQ ID NO: 3). In some embodiments, the scFv comprises an amino acid sequence that contains no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the amino acid sequence of SEQ ID NO: 4 or SEQ ID NO: 5.

In some embodiments, the scFV comprises a VH comprising the amino acid sequence of SEQ ID NO: 1 and a VL comprising the amino acid sequence of SEQ ID NO: 2, wherein the VH and VL are in a single polypeptide chain (e.g., linked via an amide bond or linked via a linker such as a peptide linker), and wherein the VH is linked to the N-terminus or the C-terminus of the VL. In some embodiments, the VH and VL are linked via a linker comprising the amino acid sequence of GGGGSGGGGSGGGGSGGGGS (SEQ ID NO: 3).

In some embodiments, the scFv comprises a VH comprising the amino acid sequence of SEQ ID NO: 1 linked to the N-terminus of a VL comprising the amino acid sequence of SEQ ID NO: 2. In some embodiments, the VH and VL are linked via a linker comprising the amino acid sequence of GGGGSGGGGSGGGGSGGGGS (SEQ ID NO: 3).

In some embodiments, the scFv comprises a VH comprising the amino acid sequence of SEQ ID NO: 1 linked to the C-terminus of a VL comprising the amino acid sequence of SEQ ID NO: 2. In some embodiments, the VH and VL are linked via a linker comprising the amino acid sequence of GGGGSGGGGSGGGGSGGGGS (SEQ ID NO: 3).

In some instances, the antibody binds to TACI with a $K_D$ of about 5 nM or lower (e.g., about 5 nM or lower, about 4 nM or lower, about 3 nM or lower, about 2 nM or lower, about 1 nM or lower, about 900 pM or lower, about 875 pM or lower, about 850 pM or lower, about 825 pM or lower, about 800 pM or lower, about 700 pM or lower, about 600 pM or lower, or about 500 pM or lower). In one embodiment, the antibody binds to TACI with a $K_D$ between about 500 pM and about 1 nM. In one embodiment, the antibody binds to TACI with a $K_D$ between about 700 pM and about 900 pM. In one embodiment, the antibody binds to TACI with a $K_D$ of about 861 pM.

In some instances, the antibody includes a heavy chain variable domain (VH) sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 1. In further instance, the antibody includes a light chain variable domain (VL) sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 2. In some instances, the antibody includes a VH sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 1 and a VL sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 2.

Such antibodies may, for example, be monoclonal, human, humanized, or chimeric. The antibodies can be full-length antibodies or antibody fragments thereof (e.g., an antibody fragment that binds TACI). The antibody fragment may be selected from the group consisting of Fab, Fab'-SH, Fv, scFv, and $(Fab')_2$ fragments. In some instances, the antibody is an IgG antibody (e.g., an IgG1 antibody). Such antibodies may have a half-life of ≥3 days (e.g., ≥1 week, e.g., ≥2 weeks, e.g., ≥1 month, e.g., ≥2 months, e.g., ≥3 months, e.g., ≥4 months, e.g., ≥5 months, e.g., ≥6 months).

In a further aspect, an anti-TACI antibody according to any of the above embodiments may incorporate any of the features, singly or in combination, as described in the sections below.

Antibody Affinity

In certain embodiments, an antibody provided herein may have a dissociation constant ($K_D$) of ≤10 μM, ≤1 μM, ≤100 nM, ≤10 nM, ≤1 nM, ≤0.1 nM, or ≤0.01 nM. In some instances, the antibody binds to TACI with a $K_D$ of about 5 nM or lower (e.g., about 5 nM or lower, about 4 nM or lower, about 3 nM or lower, about 2 nM or lower, about 1 nM or lower, about 900 pM or lower, about 875 pM or lower, about 850 pM or lower, about 825 pM or lower, about 800 pM or lower, about 700 pM or lower, about 600 pM or lower, or about 500 pM or lower). In one embodiment, the antibody binds to TACI with a $K_D$ between about 500 pM and about 1 nM. In one embodiment, the antibody binds to TACI with a $K_D$ between about 700 pM and about 900 pM. In one embodiment, the antibody binds to TACI with a $K_D$ of about 861 pM.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multiwell plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{on}/k_{off}$. See, for example, Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

According to another embodiment, $K_D$ is measured using a surface plasmon resonance assay as described herein in Example 1.

Antibody Fragments

In certain embodiments, an antibody provided herein is an antibody fragment. Antibody fragments include, but are not limited to, Fab, Fab', Fab'-SH, F(ab')$_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g., *E. coli* or phage), as described herein.

Chimeric and Humanized Antibodies

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human Antibodies

In certain embodiments, an antibody provided herein is a human antibody (e.g., a human monoclonal antibody (HuMab), e.g., an anti-TACI HuMab). Human antibodies can be produced using various techniques known in the art.

Human monoclonal antibodies can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

In some instances, human antibodies are obtained by cloning the heavy and light chain genes directly from human B cells obtained from a human subject. The B cells are separated from peripheral blood (e.g., by flow cytometry, e.g., FACS), stained for B cell marker(s), and assessed for antigen binding. The RNA encoding the heavy and light chain variable regions (or the entire heavy and light chains) is extracted and reverse transcribed into DNA, from which the antibody genes are amplified (e.g., by PCR) and sequenced. The known antibody sequences can then be used to express recombinant human antibodies against a known target antigen (e.g., TACI).

In some instances, human antibodies may be prepared by administering an immunogen (e.g., TACI) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, for example, by combining with a different human constant region.

In some instances, human antibodies can also be made by hybridoma-based methods. The preferred animal system for generating hybridomas which produce human monoclonal antibodies is the murine system. Hybridoma production in the mouse is well known in the art, including immunization protocols and techniques for isolating and fusing immunized splenocytes. Human myeloma and mouse-human heteromyeloma cell lines for the production of human monoclonal antibodies have been described.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Anti-TACI antibodies may be also produced using recombinant methods and compositions, for example, as described in U.S. Pat. No. 4,816,567. In one embodiment, isolated nucleic acid encoding an anti-TACI antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-TACI antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-TACI antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells, and myeloma cell lines such as Y0, NS0, and Sp2/0.

Antibody Variants

In certain embodiments, amino acid sequence variants of the anti-TACI antibodies are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

33

TABLE 1

Exemplary and Preferred Amino Add Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
   (1) hydrophobic: Norleucine, Met, Ala, Val, Leu, Ile;
   (2) neutral hydrophilic: Cys, Ser, Thr, Asn, Gln;
   (3) acidic: Asp, Glu;
   (4) basic: His, Lys, Arg;
   (5) residues that influence chain orientation: Gly, Pro;
   (6) aromatic: Trp, Tyr, Phe.
Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VH or VL being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two, or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, And Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region of an antibody. These alterations can be made alone, or in addition to, alterations to one or more of the antibody variable domains (i.e., VH or VL regions) or regions thereof (e.g., one or more CDRs or FRs). The alterations to the Fc region may result in enhanced antibody effector functions (e.g., complement-dependent cytotoxicity (CDC)), for example, by increasing C1q avidity to opsonized cells. Exemplary mutations that enhance CDC include, for example, Fc mutations E345R, E430G, and S440Y. Accordingly, anti-TACI antibodies may contain one or more CDC-enhancing Fc mutations, which promote IgG hexamer formation and the subsequent recruitment and activation of C1, the first component of complement.

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

Characterization of Monoclonal Antibodies to TACI

Sequence information for human monoclonal antibodies of the invention can be ascertained using sequencing techniques which are well known in the art.

Similarly, affinity of the antibodies for TACI can also be assessed using standard techniques. For example, Biacore 3000 can be used to determine the affinity of HuMabs to TACI. HuMabs are captured on the surface of a Biacore chip (GE healthcare), for example, via amine coupling (Sensor Chip CM5). The captured HuMabs can be exposed to various concentrations of TACI in solution, and the $K_{on}$ and $K_{off}$ for an affinity ($K_D$) can be calculated, for example, by BIAevaluation software.

Human monoclonal antibodies of the invention can also be characterized for binding to TACI using a variety of known techniques, such as ELISA, Western blot, etc. Generally, the antibodies are initially characterized by ELISA. In some instances, an ELISA assay can be used to screen for antibodies and, thus, hybridomas that produce antibodies that show positive reactivity with the TACI immunogen. Hybridomas that bind, preferably with high affinity, to TACI can then be subcloned and further characterized. One clone from each hybridoma, which retains the reactivity of the parent cell (by ELISA), can then be chosen for making a cell bank, and for antibody purification.

In some instances, competition assays may be used to identify an antibody that competes with an anti-TACI antibody of the invention for binding to TACI. In certain embodiments, such a competing antibody binds to the same epitope (e.g., a linear or a conformational epitope) that is bound by an anti-TACI antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, NJ).

Antibody-Drug Conjugates

In some embodiments, an anti-TACI antibody of the invention can be covalently attached by a biodegradable, stable linker (e.g., by a disulfide or non-cleavable thioether linker) to a drug moiety, i.e., as an antibody-drug conjugate. The drug to which the antibody is covalently attached may have cytotoxic or cytostatic effect when it is not conjugated to the antibody. The antibody-drug conjugate can be used to selectively delivery an effective dose of a cytotoxic agent to cells expressing TACI (e.g., to tumor tissue expressing TACI) in order to achieve greater selectivity and therefore a lower efficacious dose. By achieving higher selectivity, use of the antibody-drug conjugate may also reduce systemic exposure and increase tolerability of the drug. Additionally, the antibody-drug conjugate may improve the bioavailability of the drug and/or the antibody compared to when the drug and/or antibody is administered in its unconjugated form.

Bispecific T Cell Engagers (BiTEs)

Also provided herein are bispecific antibodies known as bispecific T cell engagers (BiTEs). Such molecules can target T cells by binding to a T cell antigen (e.g., by binding CD3) as well as a target antigen, e.g., TACI. BiTEs can be used to augment T cell response in, e.g., the tumor microenvironment. The two components of a BiTE can optionally be separated from one another by a linker as described herein (e.g., a glycine/serine-based linker), and may also be connected in either orientation, e.g., with the anti-CD3 component N-terminal to the anti-TACI component, or vice versa.

An exemplary BiTE useful for the methods described herein includes a CD3-binding domain and a TACI-binding domain. Such a BiTE may include as the CD3-binding domain an anti-CD3 scFv. The anti-CD3 scFv may be derived from any anti-CD3 antibodies known in the art.

In some instances, the TACI-binding domain (e.g., antibody) binds to TACI with a $K_D$ of about 5 nM or lower (e.g., about 5 nM or lower, about 4 nM or lower, about 3 nM or lower, about 2 nM or lower, about 1 nM or lower, about 900 pM or lower, about 875 pM or lower, about 850 pM or lower, about 825 pM or lower, about 800 pM or lower, about 700 pM or lower, about 600 pM or lower, or about 500 pM or lower). In one embodiment, the TACI-binding domain (e.g., antibody) binds to TACI with a $K_D$ between about 500 pM and about 1 nM. In one embodiment, the TACI-binding domain (e.g., antibody) binds to TACI with a $K_D$ between about 700 pM and about 900 pM. In one embodiment, the TACI-binding domain (e.g., antibody) binds to TACI with a $K_D$ of about 861 pM.

Furthermore, the BiTE may include a TACI-binding domain derived from an anti-TACI antibody as described above. In some embodiments, the TACI-binding domain includes a VH having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 1. In further embodiments, the TACI-binding domain includes a VL sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 2. In certain embodiments, the TACI-binding domain includes a VH sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 1 and a VL sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 2.

The TACI-binding domain may be positioned N-terminal to the CD3-binding domain, or the CD3-binding domain may be positioned N-terminal to the TACI-binding domain. The TACI-binding domain and CD3-binding domain may optionally be connected via a linker sequence, e.g., a linker sequence of SEQ ID NO: 3, 14, 15, 16, or 17 (described below), as well as any other linker described herein or known in the art.

Chimeric Antigen Receptors (CARs)

The technology described herein provides improved chimeric antigen receptors (CARs) for use in immunotherapy. The following discusses CARs and the various improvements.

A CAR refers to an engineered T cell receptor onto which grafts a ligand or antigen specificity onto the cell (e.g., a T cell, a natural killer (NK) cell, or an induced pluripotent stem cell (iPSC)) engineered to express the CAR. CAR places a chimeric extracellular target-binding domain that specifically binds a target, e.g., a polypeptide, expressed on the surface of a cell to be targeted for a T cell response onto a construct including a transmembrane domain and intracellular domain(s) of a T cell receptor molecule. In one embodiment, the chimeric extracellular target-binding domain includes the antigen-binding domain(s) of an antibody that specifically binds an antigen expressed on a cell to be targeted for a T cell response. The properties of the intracellular signaling domain(s) of the CAR can vary as known in the art and as disclosed herein, but the chimeric target/antigen-binding domains(s) render the receptor sensitive to signaling activation when the chimeric target/antigen binding domain binds the target/antigen on the surface of a targeted cell.

With respect to intracellular signaling domains, so-called "first-generation" CARs include those that solely provide CD3zeta (CD3ζ) signals upon antigen binding. So-called "second-generation" CARs include those that provide both co-stimulation (e.g., CD28 or CD137) and activation (CD3ζ) domains, and so-called "third-generation" CARs include those that provide multiple costimulatory (e.g., CD28 and CD137) domains and activation domains (e.g., CD3ζ). In various embodiments, the CAR is selected to have high affinity or avidity for the target/antigen—for example, antibody-derived target or antigen binding domains will generally have higher affinity and/or avidity for the target antigen than would a naturally-occurring T cell receptor. This property, combined with the high specificity one can select for an antibody provides highly specific T cell targeting by CAR T cells.

Extracellular Target Binding Domain

As used herein, the term "extracellular target binding domain" refers to a polypeptide found on the outside of the cell that is sufficient to facilitate binding to a target. The extracellular target binding domain will specifically bind to its binding partner, i.e., the target. As non-limiting examples, the extracellular target-binding domain can include an antigen-binding domain of an antibody or antibody reagent, or a ligand, which recognizes and binds with a cognate binding partner protein. In this context, a ligand is a molecule that binds specifically to a portion of a protein and/or receptor. The cognate binding partner of a ligand useful in the methods and compositions described herein can generally be found on the surface of a cell. Ligand:cognate partner binding can result in the alteration of the ligand-bearing receptor, or activate a physiological response, for example, the activation of a signaling pathway. In one embodiment, the ligand can be non-native to the genome. Optionally, the ligand has a conserved function across at least two species.

Antibody Reagents

In various embodiments, the CARs described herein include an antibody reagent or an antigen-binding domain thereof as an extracellular target-binding domain.

As used herein, the term "antibody reagent" refers to a polypeptide that includes at least one immunoglobulin variable domain or immunoglobulin variable domain sequence and which specifically binds a given antigen. For example, an antibody reagent useful for the CARs described herein includes any one of the antibodies described above. An antibody reagent can include an antibody or a polypeptide including an antigen-binding domain of an antibody. In some embodiments of any of the aspects, an antibody reagent can include a monoclonal antibody or a polypeptide including an antigen-binding domain of a monoclonal antibody. For example, an antibody can include VH and a VL. In another example, an antibody includes two VHs and two VLs. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g., de Wildt et al., Eur. J. Immunol. 26(3):629-639, 1996; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like. Fully human antibody binding domains can be selected, for example, from phage display libraries using methods known to those of ordinary skill in the art. Furthermore, antibody reagents include single domain antibodies, such as camelid antibodies.

In one embodiment, the extracellular target binding domain of a CAR includes or consists essentially of a single-chain Fv (scFv) fragment created by fusing the VH and VL domains of an antibody, generally a monoclonal antibody, via a flexible linker peptide. In various embodiments, the scFv is fused to a transmembrane domain and to a T cell receptor intracellular signaling domain, e.g., an engineered intracellular signaling domain as described herein. In another embodiment, the extracellular target binding domain of a CAR includes a single domain (e.g., camelid) antibody. Antibody binding domains and ways to select and clone them are well-known to those of ordinary skill in the art.

Target/Antigen

Any cell-surface moiety can be targeted by a CAR. Often, the target will be a cell-surface polypeptide that may be differentially or preferentially expressed on a cell that one wishes to target for a T cell response. To target tumors or cancer cells, antibody domains can be targeted against, e.g., TACI, as described herein. Targeting tumor antigens or tumor-associated antigens that are specific to the tumors can provide a means to target tumor cells while avoiding or at least limiting collateral damage to non-tumor cells or tissues.

The CARs provided herein target TACI, which is receptor that recognizes APRIL, BAFF, and CAML. TACI sequences are known for a number of species, e.g., human TACI (NCBI Gene ID: 23495) polypeptide (e.g., NCBI Ref Seq: NP_036584.1) and mRNA (e.g., NCBI Ref Seq: NM_012452.2). TACI can refer to human TACI, including naturally occurring variants, molecules, and alleles thereof. Homologs and/or orthologs of human TACI are readily identified for such species by one of skill in the art, e.g., using the NCBI ortholog search function or searching available sequence data for a given species for sequence similar to a reference TACI sequence.

In certain examples, the CARs described herein may also target an additional, second target. Non-limiting examples of additional targets, e.g., tumor antigens, tumor-associated antigens, or other antigen of interest, include BCMA, CD19, CD37, CEA, immature laminin receptor, TAG-72, HPV E6 and E7, BING-4, calcium-activated chloride channel 2, cyclin B1, 9D7, Ep-CAM, EphA3, Her2/neu, telomerase, mesothelin, SAP-1, survivin, BAGE family, CAGE family, GAGE family, MAGE family, SAGE family, XAGE family, NY-ESO-1/LAGE-1, PRAME, SSX-2, Melan-A/MART-1, gp100/pmel17, tyrosinase, TRP-1/-2, MC1R, BRCA1/2, CDK4, MART-2, p53, Ras, MUC1, TGF-βRII, IL-15, IL13Ra2, and CSF1R. In certain embodiments, the second target is BCMA.

TACI-Binding Domain

In some embodiments, the invention provides an anti-TACI CAR including a TACI-binding domain including an antibody reagent. In some instances, the TACI-binding domain binds to TACI with a $K_D$ of about 5 nM or lower (e.g., about 5 nM or lower, about 4 nM or lower, about 3 nM or lower, about 2 nM or lower, about 1 nM or lower, about 900 pM or lower, about 875 pM or lower, about 850 pM or lower, about 825 pM or lower, about 800 pM or lower, about 700 pM or lower, about 600 pM or lower, or about 500 pM or lower). In one embodiment, the TACI-binding domain binds to TACI with a $K_D$ between about 500 pM and about 1 nM. In one embodiment, the TACI-binding domain binds to TACI with a $K_D$ between about 700 pM and about 900 pM. In one embodiment, the TACI-binding domain binds to TACI with a $K_D$ of about 861 pM.

For example, the antibody reagent can be an anti-TACI antibody or antigen binding fragment thereof, e.g., an anti-TACI scFv. In some embodiments, the anti-TACI scFv includes a VH sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 1. In other embodiments, the anti-TACI scFv includes a VL sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 2. In some instances, the anti-TACI scFv includes a VH sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 1 and a VL sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 2. The VH may be positioned N-terminal to the VL (VH-VL), or the VL may be positioned N-terminal to the VH (VL-VH)

The VH and VL domains may be connected via a linker sequence. For instance, linker sequences useful for the invention include, but are not limited to, glycine/serine linkers, e.g., GGGSGGGSGGGS (SEQ ID NO: 14) and Gly4Ser (G4S) linkers such as (G4S)3 (GGGGSGGGGSGGGGS (SEQ ID NO: 15)) and (G4S)4 (GGGGSGGGGSGGGGSGGGGS (SEQ ID NO: 3)); the linker sequence of GSTSGSGKPGSGEGSTKG (SEQ ID NO: 16) as described by Whitlow et al., Protein Eng. 6(8):989-95, 1993, the contents of which are incorporated herein by reference in its entirety; the linker sequence of GGSSRSSSSGGGGSGGGG (SEQ ID NO: 17) as described by Andris-Widhopf et al., Cold Spring Harb. Protoc. 2011 (9), 2011, the contents of which are incorporated herein by reference in its entirety; as well as linker sequences with added functionalities, e.g., an epitope tag or an encoding sequence containing Cre-Lox recombination site as described by Sblattero et al., Nat. Biotechnol. 18(1):75-80, 2000, the contents of which are incorporated herein by reference in its entirety.

In specific embodiments, an anti-TACI CAR as described herein may include an anti-TACI scFv having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to, or the sequence of, SEQ ID NO: 3 (VH-VL) or 4 (VL-VH).

Bispecific CARs

In another embodiment, the CARs useful in the technology described herein include extracellular target binding domain including at least two antigen-specific targeting regions, a transmembrane domain, and an intracellular signaling domain. In such embodiments, the two or more antigen-specific targeting regions target at least two different antigens and may be arranged in tandem and separated by linker sequences. In another embodiment, the CAR is a bispecific CAR. A bispecific CAR is specific to two different antigens, e.g., TACI and any one of the additional targets described herein (e.g., BCMA).

For example, a bispecific CAR can target TACI and BCMA and includes a TACI-binding domain and a BCMA-binding domain. Such a bispecific CAR may include the TACI-binding domain (e.g., an anti-TACI scFv) as described above. In some embodiments, the BCMA-binding domain includes an anti-BCMA scFv. The anti-BCMA scFv may be derived from any anti-BCMA antibodies known in the art. The TACI-binding domain may be positioned N-terminal to the BCMA-binding domain, or the BCMA-binding domain may be positioned N-terminal to the TACI-binding domain. The TACI-binding domain and BCMA-binding domain may optionally be connected via a linker sequence, e.g., a linker sequence of SEQ ID NO: 3, 14, 15, 16, or 17, as well as any other linker described herein or known in the art.

In some embodiments, the bispecific CAR targeting TACI and BCMA described herein comprises an amino acid sequence that is at least 80%, at least 85%, at least 90%, at least 95%, or at least 99% identical to the amino acid sequence of any one of SEQ ID NOs: 18-25. In some embodiments, the bispecific CAR targeting TACI and BCMA described herein comprises an amino acid sequence that is 80%, 85%, 90%, 95%, or 99% identical to the amino acid sequence of any one of SEQ ID NOs: 18-25. In some embodiments, the bispecific CAR targeting TACI and BCMA described herein comprises the amino acid sequence of any one of SEQ ID NOs: 18-25.

Hinge and Transmembrane Domains

Each CAR as described herein includes a transmembrane domain, e.g., a hinge/transmembrane domain, which joins the extracellular target-binding domain to the intracellular signaling domain.

The binding domain of the CAR is optionally followed by one or more "hinge domains," which plays a role in positioning the antigen binding domain away from the effector cell surface to enable proper cell/cell contact, antigen binding and activation. A CAR optionally includes one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8 (e.g., CD8a), CD4, CD28, 4-1BB, and CD7, which may be wild-type hinge regions from these molecules or may be altered. In some embodiments, the hinge region is derived from the hinge region of an immunoglobulin-like protein (e.g., IgA, IgD, IgE, IgG, or IgM), CD28, or CD8. In one embodiment, the hinge domain includes a CD8a hinge region.

As used herein, "transmembrane domain" (TM domain) refers to the portion of the CAR that fuses the extracellular binding portion, optionally via a hinge domain, to the intracellular portion (e.g., the co-stimulatory domain and intracellular signaling domain) and anchors the CAR to the plasma membrane of the immune effector cell. The transmembrane domain is a generally hydrophobic region of the CAR which crosses the plasma membrane of a cell. The TM domain can be the transmembrane region or fragment thereof of a transmembrane protein (for example a Type I transmembrane protein or other transmembrane protein), an artificial hydrophobic sequence, or a combination thereof. While specific examples are provided herein and used in the Examples, other transmembrane domains will be apparent to those of skill in the art and can be used in connection with alternate embodiments of the technology. A selected transmembrane region or fragment thereof would preferably not interfere with the intended function of the CAR. As used in relation to a transmembrane domain of a protein or polypeptide, "fragment thereof" refers to a portion of a transmembrane domain that is sufficient to anchor or attach a protein to a cell surface.

In some examples, the transmembrane domain or fragment thereof of the CAR described herein includes a transmembrane domain selected from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), 4-1BBL, GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

As used herein, a "hinge/transmembrane domain" refers to a domain including both a hinge domain and a transmembrane domain. For example, a hinge/transmembrane domain can be derived from the hinge/transmembrane domain of CD8, CD28, CD7, or 4-1BB. In one embodiment, the hinge/transmembrane domain of a CAR or fragment thereof is derived from or includes the hinge/transmembrane domain of CD8.

CD8 is an antigen preferentially found on the cell surface of cytotoxic T lymphocytes. CD8 mediates cell-cell interactions within the immune system, and acts as a T cell co-receptor. CD8 consists of an alpha (CD8a or CD8a) and beta (CD8β or CD8b) chain. CD8a sequences are known for a number of species, e.g., human CD8a, (NCBI Gene ID: 925) polypeptide (e.g., NCBI Ref Seq NP_001139345.1) and mRNA (e.g., NCBI Ref Seq NM_000002.12). CD8 can refer to human CD8, including naturally occurring variants, molecules, and alleles thereof. In some embodiments of any of the aspects, e.g., in veterinary applications, CD8 can refer to the CD8 of, e.g., dog, cat, cow, horse, pig, and the like. Homologs and/or orthologs of human CD8 are readily identified for such species by one of skill in the art, e.g., using the NCBI ortholog search function or searching available sequence data for a given species for sequence similar to a reference CD8 sequence.

In some embodiments, the CD8 hinge and transmembrane sequence corresponds to the amino acid sequence of SEQ ID NO: 7; or includes the sequence of SEQ ID NO: 7; or includes a sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to the sequence of SEQ ID NO: 7.

Co-Stimulatory Domains

Each CAR described herein optionally includes the intracellular domain of one or more co-stimulatory molecule or co-stimulatory domain. As used herein, the term "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. The co-stimulatory domain can be, for example, the co-stimulatory domain of 4-1BB, CD27, CD28, or OX40.

Additional illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70.

In one embodiment, the co-stimulatory domain is the co-stimulatory domain of 4-1BB. 4-1BB is a membrane receptor protein, also known as CD137, which is a member of the tumor necrosis factor (TNF) receptor superfamily. 4-1BB is expressed on activated T lymphocytes. 4-1BB sequences are known for a number of species, e.g., human 4-1BB, also known as TNFRSF9 (NCBI Gene ID: 3604) and mRNA (NCBI Reference Sequence: NM_001561.5). 4-1BB can refer to human 4-1BB, including naturally occurring variants, molecules, and alleles thereof. In some embodiments of any of the aspects, e.g., in veterinary applications, 4-1BB can refer to the 4-1BB of, e.g., dog, cat, cow, horse, pig, and the like. Homologs and/or orthologs of human 4-1BB are readily identified for such species by one of skill in the art, e.g., using the NCBI ortholog search function or searching available sequence data for a given species for sequence similar to a reference 4-1BB sequence.

In some embodiments, the co-stimulatory domain of 4-1BB corresponds to an amino acid sequence of SEQ ID NO: 8; or includes a sequence of SEQ ID NO: 8; or includes an amino acid having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to a sequence of SEQ ID NO: 8.

Intracellular Signaling Domains

CARs as described herein include an intracellular signaling domain. An "intracellular signaling domain," refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain. In various examples, the intracellular signaling domain is from CD3 (see, e.g., below). Additional non-limiting examples of immunoreceptor tyrosine-based activation motif (ITAM)-containing intracellular signaling domains that are of particular use in the technology include those derived from TCRζ, FcRγ, FcRβ, CD3γ, CD3θ, CD3δ, CD3η, CD3ε, CD3ζ, CD22, CD79a, CD79b, and CD66d.

CD3 is a T cell co-receptor that facilitates T lymphocyte activation when simultaneously engaged with the appropriate co-stimulation (e.g., binding of a co-stimulatory molecule). A CD3 complex consists of 4 distinct chains; mammalian CD3 consists of a CD3γ chain, a CD3δ chain, and two CD3ε chains. These chains associate with a molecule known as the T cell receptor (TCR) and the CD3ζ to generate an activation signal in T lymphocytes. A complete TCR complex includes a TCR, CD3ζ, and the complete CD3 complex.

In some embodiments of any aspect, a CAR polypeptide described herein includes an intracellular signaling domain that includes an Immunoreceptor Tyrosine-based Activation Motif or ITAM from CD3 zeta (CD3ζ), including variants of CD3ζ such as ITAM-mutated CD3ζ, CD3η, or CD3θ. In some embodiments of any aspect, the ITAM includes three motifs of ITAM of CD3ζ (ITAM3). In some embodiments of any aspect, the three motifs of ITAM of CD3ζ are not mutated and, therefore, include native or wild-type sequences. In some embodiments, the CD3ζ sequence includes the sequence of a CD3ζ as set forth in the sequences provided herein, e.g., a CD3ζ sequence of SEQ ID NO: 9, or variants thereof.

For example, a CAR polypeptide described herein includes the intracellular signaling domain of CD3ζ. In one embodiment, the CD3ζ intracellular signaling domain corresponds to an amino acid sequence of SEQ ID NO: 9; or includes a sequence of SEQ ID NO: 9; or includes a sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to a sequence of SEQ ID NO: 9.

Individual CAR and other construct components as described herein can be used with one another and swapped in and out of various constructs described herein, as can be determined by those of skill in the art. Each of these components can include or consist of any of the corresponding sequences set forth herein, or variants thereof.

A more detailed description of CARs and CAR T cells can be found in Maus et al., Blood 123:2624-2635, 2014; Reardon et al., Neuro-Oncology 16:1441-1458, 2014; Hoyos et al., Haematologica 97:1622, 2012; Byrd et al., J. Clin. Oncol. 32:3039-3047, 2014; Maher et al., Cancer Res 69:4559-4562, 2009; and Tamada et al., Clin. Cancer Res. 18:6436-6445, 2012; each of which is incorporated by reference herein in its entirety.

In some embodiments, a CAR polypeptide as described herein includes a signal peptide. Signal peptides can be derived from any protein that has an extracellular domain or is secreted. A CAR polypeptide as described herein may include any signal peptides known in the art. In some embodiments, the CAR polypeptide includes a CD8 signal peptide, e.g., a CD8 signal peptide corresponding to the amino acid sequence of SEQ ID NO: 6, or including the amino acid sequence of SEQ ID NO: 6, or including an amino acid sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to the sequence of SEQ ID NO: 6.

In further embodiments, a CAR polypeptide described herein may optionally exclude one of the signal peptides described herein, e.g., a CD8 signal peptide of SEQ ID NO: 6.

In one embodiment, the CAR further includes a linker domain. As used herein, "linker domain" refers to an oligo- or polypeptide region from about 2 to 100 amino acids in length, which links together any of the domains/regions of the CAR as described herein. In some embodiment, linkers can include or be composed of flexible residues such as glycine and serine so that the adjacent protein domains are free to move relative to one another. Linker sequences useful for the invention can be from 2 to 100 amino acids, 5 to 50 amino acids, 10 to 15 amino acids, 15 to 20 amino acids, or 18 to 20 amino acids in length, and include any suitable linkers known in the art and/or described herein (e.g., the linker sequence of SEQ ID NO: 3, 14, 15, 16, or 7). Longer linkers may be used when it is desirable to ensure that two adjacent domains do not sterically interfere with one another. Furthermore, linkers may be cleavable or non-cleavable. Examples of cleavable linkers include 2A linkers (e.g., P2A and T2A), 2A-like linkers or functional equivalents thereof and combinations thereof. In various examples, linkers having sequences as set forth herein, or variants thereof, are used. It is to be understood that the indication of a particular linker in a construct in a particular location does not mean that only that linker can be used there. Rather, different linker sequences (e.g., P2A and T2A) can be swapped with one another (e.g., in the context of the constructs of the present invention), as can be determined by those of skill in the art. In one embodiment, the linker region is T2A derived from *Thosea asigna* virus. Non-limiting examples of linkers that can be used in this technology include T2A, P2A, E2A, BmCPV2A, and BmIFV2A.

In some embodiments, a CAR as described herein optionally further includes a reporter molecule, e.g., to permit for non-invasive imaging (e.g., positron-emission tomography PET scan). In a bispecific CAR that includes a reporter molecule, the first extracellular binding domain and the second extracellular binding domain can include different or the same reporter molecule. In a bispecific CAR T cell, the first CAR and the second CAR can express different or the same reporter molecule. In another embodiment, a CAR as described herein further includes a reporter molecule (for example hygromycin phosphotransferase (hph)) that can be imaged alone or in combination with a substrate or chemical (for example 9-[4-[$^{18}$F]fluoro-3-(hydroxymethyl)butyl]guanine ([$^{18}$F]FHBG)). In another embodiment, a CAR as described herein further includes nanoparticles at can be readily imaged using non-invasive techniques (e.g., gold nanoparticles (GNP) functionalized with $^{64}$Cu$^{2+}$). Labeling of CAR T cells for non-invasive imaging is reviewed, for example in Bhatnagar et al., Integr. Biol. (Camb). 5(1):231-238, 2013, and Keu et al., Sci. Transl. Med. 18; 9(373), 2017, which are incorporated herein by reference in their entireties.

GFP and mCherry are demonstrated herein as fluorescent tags useful for imaging a CAR expressed on a T cell (e.g., a CAR T cell). It is expected that essentially any fluorescent protein known in the art can be used as a fluorescent tag for this purpose. For clinical applications, the CAR need not include a fluorescent tag or fluorescent protein. In each instance of particular constructs provided herein, therefore, any markers present in the constructs can be removed. The invention includes the constructs with or without the markers. Accordingly, when a specific construct is referenced herein, it can be considered with or without any markers or tags as being included within the invention.

In some embodiments, the CAR polypeptide sequence corresponds to, includes, or includes a sequence having at least 80% sequence identity (e.g., at least 81%, 82%, 83%, 84%, 85%, 86%, 87%, 88%, 89%, 90,% 91%, 92%, 93%, 94%, 95%, 96%, 97%, 98%, or 99% sequence identity) to the sequence of SEQ ID NO: 10, 11, 12, or 13, optionally excluding a CD8 signal peptide as described herein. As can be determined by those of skill in the art, various functionally similar or equivalent components of these CARs can be swapped or substituted with one another, as well as other similar or functionally equivalent components known in the art or listed herein.

Nucleic Acids Encoding CARs

In some embodiments, any of the CAR polypeptides described herein (e.g., a CAR polypeptide of SEQ ID NO: 10, 11, 12, or 13) are encoded by a polynucleotide comprised in a viral vector. Optionally, a polynucleotide encoding a CAR polypeptide as described herein can be codon-optimized to enhance expression or stability. Codon optimization may be performed according to any standard methods known in the art. In some embodiments, expression of the CAR can be driven by a constitutively expressed promoter (e.g., an EF1α promoter) or an inducibly expressed promoter (e.g., an NFAT response element).

Furthermore, the polynucleotides of the invention can include the expression of a suicide gene. This can be done to facilitate external, drug-mediated control of administered cells. For example, by use of a suicide gene, modified cells can be depleted from the patient in case of, e.g., an adverse event. In one example, the FK506 binding domain is fused to the caspase9 pro-apoptotic molecule. T cells engineered in this manner are rendered sensitive to the immunosuppressive drug tacrolimus. Other examples of suicide genes are thymidine kinase (TK), CD20, thymidylate kinase, truncated prostate-specific membrane antigen (PSMA), truncated low affinity nerve growth factor receptor (LNGFR), truncated CD19, and modified Fas, which can be triggered for conditional ablation by the administration of specific molecules (e.g., ganciclovir to TK+ cells) or antibodies or antibody-drug conjugates.

Retroviruses, such as lentiviruses, provide a convenient platform for delivery of nucleic acid sequences encoding a gene, or chimeric gene of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety. Lentiviral system for efficient DNA delivery can be purchased from OriGene; Rockville, MD In alternative embodiments, the CAR polypeptide of any of the CARs described herein are expressed in the mammalian cell via transfection or electroporation of an expression vector comprising nucleic acid encoding the CAR. Transfection or electroporation methods are known in the art.

Efficient expression of the CAR polypeptide of any of the CAR polypeptides described herein can be assessed using standard assays that detect the mRNA, DNA, or gene product of the nucleic acid encoding the CAR, such as RT-PCR, FACS, northern blotting, western blotting, ELISA, or immunohistochemistry. In some embodiments, the CAR polypeptide of any of the CAR polypeptides described herein is encoded by recombinant nucleic acid sequence.

Cells

Another aspect of the invention relates to a mammalian cell comprising any of the CAR polypeptides described herein; or a nucleic acid encoding any of the CAR polypeptides described herein. In one embodiment, the mammalian cell comprises an antibody, antibody reagent, antigen-binding portion thereof, or any of the CAR polypeptides described herein, or a nucleic acid encoding such an antibody, antibody reagent, antigen-binding portion thereof, or any of the CAR polypeptides described herein. The mammalian cell or tissue can be of human, primate, hamster, rabbit, rodent, cow, pig, sheep, horse, goat, dog or cat origin, but any other mammalian cell may be used. In a preferred embodiment of any aspect, the mammalian cell is human.

In one example, the mammalian cell is an induced pluripotent stem cell (iPSC), e.g., as described by Takahashi K and Yamanaka S, "Induction of pluripotent stem cells from mouse embryonic and adult fibroblast cultures by defined factors," *Cell*. 126(4):663-76 (2006), which is incorporated herein by reference in its entirety. In other embodiments, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the immune cell is a T cell; a NK cell; a NKT cell; lymphocytes, such as B cells and T cells; and myeloid cells, such as monocytes, macrophages, eosinophils, mast cells, basophils, and granulocytes. In one embodiment, the cell is a T cell or a natural killer (NK) cell.

The mammalian cell (e.g., an iPSC or an immune cell (e.g., a T cell or an NK cell)) can be obtained from a subject having or diagnosed as having cancer, a plasma cell disease or disorder, or an autoimmune disease or disorder. For example, the mammalian cell (e.g., an iPSC or an immune cell (e.g., a T cell or an NK cell)) can be obtained from a subject having a cancer, e.g., multiple myeloma, smoldering myeloma, or Waldenstrom's macroglobulenemia. In some embodiments, the mammalian cell (e.g., an iPSC or an immune cell (e.g., a T cell or an NK cell)) is obtained from a subject resistant to anti-BCMA therapy. Cells can also be obtained from allogeneic donors, which are non-genetically identical individuals of the same species as the intended recipients of the cells.

Mammalian cells (e.g., iPSCs or immune cells (e.g., T or NK cells)) that can be used in the invention include autologous cells, obtained from the subject to whom the cells are later to be administered, after ex vivo modification and expansion. For example, the mammalian cell (e.g., an iPSC or an immune cell (e.g., a T cell or an NK cell)) can be obtained from an individual having or diagnosed as having cancer, a plasma cell disease or disorder, or autoimmune disease or disorder. Mammalian cells (e.g., iPSCs or immune cells (e.g., T or NK cells)) can also be obtained from allogeneic donors, which are non-genetically identical individuals of the same species as the intended recipients of the cells. Mammalian cells useful for the invention include, without limitation, iPSCs and immune cells (e.g., T or NK cells).

Methods for obtaining T cells and NK are known in the art and can be useful for the engineered immune cells described herein. T cells and NK cells are typically obtained from peripheral blood that is collected from a subject by, e.g., venipuncture or withdrawal through an implanted port or catheter. Optionally, the blood can be obtained by a process including leukapheresis, in which white cells are obtained from the blood of a subject, while other blood components are returned to the subject. Blood or leukapheresis product (fresh or cryopreserved) is processed to enrich for T cells or NK cells using methods known in the art. For example, density gradient centrifugation (using, e.g., Ficoll) and/or counter-flow centrifugal elutriation can be carried out to enrich for mononuclear cells (including T cells or NK cells). In one example, for T cells, a T cell stimulation step employing, e.g., CD3/CD28 antibodies coated on magnetic beads or artificial antigen presenting cells (aAPCs) expressing, e.g., cell surface-bound anti-CD3 and anti-CD28 antibody fragments (see below), can further be carried out in order to stimulate T cells and to deplete other cells, e.g., B cells. The T cells of enriched T cell preparations can then be subject to genetic modification.

As an alternative to peripheral blood, tissues including bone marrow, lymph nodes, spleen, and tumors can be used as a source for T cells and NK cells. The T cells and NK cells can be of human, primate, hamster, rabbit, rodent, cow, pig, sheep, horse, goat, dog, or cat origin, but any other mammalian cell may be used. In a certain embodiments of any aspect, the T or NK cell is human.

A mammalian cell (e.g., an iPSC or an immune cell (e.g., a T cell or an NK cell)), can be engineered to comprise any of the CAR polypeptides described herein (e.g., the CAR polypeptide of SEQ ID NO: 10, 11, 12, or 13); or a nucleic acid encoding any of the CAR polypeptides described herein (e.g., a nucleic acid encoding the CAR polypeptide of SEQ ID NO: 10, 11, 12, or 13).

The invention furthermore provides compositions and methods for treating and preventing diseases and conditions including, e.g., cancer, autoimmune diseases or disorders, or plasma cell diseases or disorders. These methods include the use of a mammalian cell (e.g., an iPSC or an immune cell (e.g., a T cell or an NK cell)) including a CAR polypeptide, or a nucleic acid encoding said CAR, as described herein, and administering the modified mammalian cell to a subject to treat, e.g., cancer. In some embodiments of any of the aspect, the modified mammalian cell (e.g., an iPSC or an immune cell (e.g., a T cell or an NK cell) including one or more additional modification as described herein) is stimulated and/or activated prior to administration to the subject.
Therapeutic Methods The anti-TACI antibodies, antibody-drug conjugates, BiTEs, and/or anti-TACI CARs described herein may be useful for treating a disease or disorder in a subject, e.g., a cancer, an autoimmune disorder, or a plasma cell disease or disorder.

The term "cancer" as used herein refers to a hyperproliferation of cells whose unique trait, loss of normal cellular control, results in unregulated growth, lack of differentiation, local tissue invasion, and metastasis. As used herein, the term "tumor" refers to an abnormal growth of cells or tissues, e.g., of malignant type or benign type. Examples of cancers include, but are not limited to, glioblastoma, prostate cancer, glioma, leukemia, lymphoma, multiple myeloma, or a solid tumor, e.g., lung cancer and pancreatic cancer. Non-limiting examples of leukemia include acute myeloid leukemia (AML), chronic myeloid leukemia (CML), acute lymphocytic leukemia (ALL), and chronic lymphocytic leukemia (CLL). In one embodiment, the cancer is ALL or CLL. Non-limiting examples of lymphoma include diffuse large B-cell lymphoma (DLBCL), follicular lymphoma, small lymphocytic lymphoma (SLL), mantle cell lymphoma (MCL), marginal zone lymphomas, Burkitt's lymphoma, hairy cell leukemia (HCL), and T cell lymphoma (e.g., peripheral T cell lymphoma (PTCL), including cutaneous T cell lymphoma (CTCL) and anaplastic large cell lymphoma (ALCL)). In one embodiment, the cancer is DLBCL or follicular lymphoma. Non-limiting examples of solid tumors include adrenocortical tumor, alveolar soft part sarcoma, carcinoma, chondrosarcoma, colorectal carcinoma, desmoid tumors, desmoplastic small round cell tumor, endocrine tumors, endodermal sinus tumor, epithelioid hemangioendothelioma, Ewing sarcoma, germ cell tumors (solid tumor), giant cell tumor of bone and soft tissue, hepatoblastoma, hepatocellular carcinoma, melanoma, nephroma, neuroblastoma, non-rhabdomyosarcoma soft tissue sarcoma (NRSTS), osteosarcoma, paraspinal sarcoma, renal cell carcinoma, retinoblastoma, rhabdomyosarcoma, synovial sarcoma, and Wilms tumor. Solid tumors can be found in bones, muscles, or organs, and can be sarcomas or carcinomas.

As used herein, an "autoimmune disease or disorder" is characterized by the inability of one's immune system to distinguish between a foreign cell and a healthy cell. This results in one's immune system targeting one's healthy cells for programmed cell death. Non-limiting examples of an autoimmune disease or disorder include inflammatory arthritis, type 1 diabetes mellitus, multiples sclerosis, psoriasis, inflammatory bowel diseases, SLE, and vasculitis, allergic inflammation, such as allergic asthma, atopic dermatitis, and contact hypersensitivity. Other examples of autoimmune diseases or disorders include, but are not limited to, transplant rejection, graft versus host disease, hemophilia with Factor inhibitors, rheumatoid arthritis, multiple sclerosis (MS), systemic lupus erythematosus, Graves' disease (overactive thyroid), Hashimoto's thyroiditis (underactive thyroid), celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, acute disseminated encephalomyelitis, antiphospholipid antibody syndrome, aplastic anemia, idiopathic thrombocytopenic purpura, myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

A plasma cell is a white blood cell produces from B lymphocytes which function to generate and release antibodies needed to fight infections. As used herein, a "plasma cell disease or disorder" is characterized by abnormal multiplication of a plasma cell. Abnormal plasma cells are capable of "crowding out" healthy plasma cells, which results in a decreased capacity to fight a foreign object, such as a virus or bacterial cell. Non-limiting examples of plasma cell diseases or disorders include plasma cell dyscrasias, plasmacytoma, plasma cell leukemia, multiple myeloma, Waldenstrom's macroglobulinemia, solitary plasmacytoma, extramedullary plasmacytoma, osteosclerotic myeloma, heavy chain diseases, monoclonal gammopathy of undetermined significance, and smoldering multiple myeloma.

Exemplary cancers that may be treated by the anti-TACI antibodies, antibody-drug conjugates, BiTEs, and/or anti-TACI CARs described herein include cancers including cells that express TACI, e.g., multiple myeloma. Exemplary autoimmune disease that may be treated by the anti-TACI antibodies, antibody-drug conjugates, BiTEs, and/or anti-TACI CARs described herein include autoimmune diseases characterized by a high titer of antibodies contributing to the autoimmune disorder. For example, the autoimmune disorder can be transplant rejection, graft versus host disease, or hemophilia with Factor inhibitors. Plasma cell diseases or disorders that may be treated by the anti-TACI antibodies, antibody-drug conjugates, BiTEs, and/or anti-TACI CARs described herein include plasma cell dyscrasias, plasmacytoma, plasma cell leukemia, multiple myeloma, Waldenstrom's macroglobulinemia, solitary plasmacytoma, extramedullary plasmacytoma, osteosclerotic myeloma, heavy chain diseases, monoclonal gammopathy of undetermined significance, and smoldering multiple myeloma. In certain embodiments, the subject is resistant to anti-BCMA therapy.
Administration In some embodiments, the methods described herein relate to treating a subject having or diagnosed as having a cancer, a plasma cell disease or disorder, or an autoimmune disease or disorder with a mammalian cell including any of the anti-TACI antibodies, antibody-drug conjugates, BiTEs, and/or anti-TACI CARs described herein. For example, the anti-TACI CARs described herein include mammalian cells including any of the anti-TACI CAR polypeptides (and optional antibody reagents or cytokines) described herein, or a nucleic acid encoding any of the anti-TACI CAR polypeptides (and optional antibody reagents or cytokines) described herein. Subjects having a cancer, a plasma cell disease or disorder, or an autoimmune disease or disorder can be identified by a physician using current methods of diagnosing the condition. Symptoms and/or complications of the condition, which characterize these conditions and aid in diagnosis are well known in the art and include but are not limited to, fatigue, persistent infections, and persistent bleeding. Tests that may aid in a diagnosis of, e.g., the condition, but are not limited to, blood screening and bone marrow testing, and are known in the art for a given condition. A family history for a condition, or exposure to risk factors for a condition can also aid in determining if a subject is likely to have the condition or in making a diagnosis of the condition.

The compositions described herein can be administered to a subject having or diagnosed as having a condition. In some embodiments, the methods described herein include administering an effective amount of activated CAR T cells described herein to a subject in order to alleviate a symptom of the condition. As used herein, "alleviating a symptom of the condition" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art, including oral, parenteral, intrapulmonary, and intranasal, and, if desired for local treatment, intralesional administration. Parenteral infusions include intramuscular, intravenous, intraarterial, intraperitoneal, or subcutaneous administration. In one embodiment, the compositions described herein are administered systemically or locally. In a preferred embodiment, the compositions described herein are administered intravenously. In another embodiment, the compositions described herein are administered at the site of a tumor. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of activated CAR T cells, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bone marrow testing, among others. The dosage can be determined by a physician and adjusted, as necessary, to suit observed effects of the treatment.

In one aspect of the technology, the technology described herein relates to a pharmaceutical composition including activated CAR T cells as described herein, and optionally a pharmaceutically acceptable carrier. The active ingredients of the pharmaceutical composition at a minimum include activated CAR T cells as described herein. In some embodiments, the active ingredients of the pharmaceutical composition consist essentially of activated CAR T cells as described herein. In some embodiments, the active ingredients of the pharmaceutical composition consist of activated CAR T cells as described herein. Pharmaceutically acceptable carriers for cell-based therapeutic formulation include saline and aqueous buffer solutions, Ringer's solution, and serum component, such as serum albumin, HDL and LDL. The terms such as "excipient," "carrier," "pharmaceutically acceptable carrier" or the like are used interchangeably herein.

In some embodiments, the pharmaceutical composition including activated CAR T cells as described herein can be a parenteral dose form. Since administration of parenteral dosage forms typically bypasses the patient's natural defenses against contaminants, the components apart from the CAR T cells themselves are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Any of these can be added to the activated CAR T cells preparation prior to administration.

Suitable vehicles that can be used to provide parenteral dosage forms of activated CAR T cells as disclosed within are well known to those skilled in the art. Examples include, without limitation: saline solution; glucose solution; aqueous vehicles including but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Dosage

"Unit dosage form" as the term is used herein refers to a dosage for suitable one administration. By way of example, a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

In some embodiments, the anti-TACI antibodies, antibody-drug conjugates, BiTEs, and/or anti-TACI CARs described herein are administered as a monotherapy, i.e., another treatment for the condition is not concurrently administered to the subject.

As a general proposition, the therapeutically effective amount of the anti-TACI antibody, antibody-drug conjugate, and/or BiTE administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.1 to about 10 mg/kg, or about 1 to about 10 mg/kg administered one (single administration) or more times (multiple administrations, e.g., daily administrations). In one example, the antibody used is about 10 mg/kg, preferably administered orally. In one embodiment, an anti-TACI antibody, antibody-drug conjugate, and/or BiTE described herein is administered to a human at a flat dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.01 mg/kg to about 10 mg/kg. Such doses may be administered intermittently, for example, every week or every three weeks (e.g., such that the patient receives from about two to about twenty, or, for example, about six doses of the anti-TACI antibody, antibody-drug conjugate, and/or BiTE). An initial higher loading dose, followed by one or more lower doses may be administered. The progress of this therapy is easily monitored by conventional techniques and assays.

On the other hand, a pharmaceutical composition including the mammalian cells including the anti-TACI CAR described herein can generally be administered at a dosage of $10^4$ to $10^9$ cells/kg body weight, in some instances $10^5$ to $10^6$ cells/kg body weight, including all integer values within those ranges. If necessary, the cell compositions can also be administered multiple times at these dosages. The cells can be administered by using infusion techniques that are commonly known in immunotherapy (see, e.g., Rosenberg et al., New Eng. J. Med. 319:1676, 1988). In some instances, it may be desirable to administer activated CAR T cells to a subject and then subsequently redraw blood (or have an apheresis performed), activate T cells therefrom as described herein, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc. Modes of administration can include, for example intravenous (i.v.) injection or infusion. The compositions described herein can be administered to a patient transarterially, intratumorally, intranodally, or intramedullary. In some embodiments, the compositions of T cells may be injected directly into a tumor, lymph node, or site of infection. In one embodiment, the compositions described herein are administered into a body cavity or body fluid (e.g., ascites, pleural fluid, peritoneal fluid, or cerebrospinal fluid).

In a particular exemplary aspect, subjects may undergo leukapheresis, wherein leukocytes are collected, enriched, or depleted ex vivo to select and/or isolate the cells of interest, e.g., T cells. These T cell isolates can be expanded by contact with an artificial APC, e.g., an aAPC expressing anti-CD28 and anti-CD3 CDRs, and treated such that one or more CAR constructs of the technology may be introduced, thereby creating a CAR T cell. Subjects in need thereof can subsequently undergo standard treatment with high dose chemotherapy followed by peripheral blood stem cell transplantation. Following or concurrent with the transplant, subjects can receive an infusion of the expanded CAR T cells. In one embodiment, expanded cells are administered before or following surgery.

In some embodiments, lymphodepletion is performed on a subject prior to administering one or more CAR T cell as described herein. In such embodiments, the lymphodepletion can include administering one or more of melphalan, cytoxan, cyclophosphamide, and fludarabine.

The dosage of the above treatments to be administered to a patient will vary with the precise nature of the condition being treated and the recipient of the treatment. The scaling of dosages for human administration can be performed according to art-accepted practices.

In some embodiments, a single treatment regimen is required. In others, administration of one or more subsequent doses or treatment regimens can be performed. For example, after treatment biweekly for three months, treatment can be repeated once per month, for six months or a year or longer. In some embodiments, no additional treatments are administered following the initial treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Combination Therapy

The anti-TACI antibodies, antibody-drug conjugates, BiTEs, and/or anti-TACI CARs described herein can optionally be used in combination with each other and with other known agents and therapies, as can determined to be appropriate by those of skill in the art. In one example, two or more different types of CARs targeting different cancer antigens (e.g., TACI and BCMA) can be administered in combination.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The anti-TACI antibodies, antibody-drug conjugates, BiTEs, and/or anti-TACI CARs described herein and the at least one additional therapeutic agent can be administered simultaneously, in the same or in separate compositions, or sequentially. For sequential administration, the anti-TACI antibodies, antibody-drug conjugates, BiTEs, and/or anti-TACI CARs described herein can be administered first, and the additional agent can be administered second, or the order of administration can be reversed. The anti-TACI antibody, antibody-drug conjugate, BiTE, and/or anti-TACI CAR therapy and/or other therapeutic agents, procedures or modalities can be administered during periods of active disorder, or during a period of remission or less active disease. The anti-TACI antibody, antibody-drug conjugate, BiTE, and/or anti-TACI CAR therapy can be administered before another treatment, concurrently with the treatment, post-treatment, or during remission of the disorder.

When administered in combination, the anti-TACI antibody, antibody-drug conjugate, BiTE, and/or anti-TACI CAR therapy and the additional agent (e.g., second or third agent), or all, can be administered in an amount or dose that is higher, lower or the same as the amount or dosage of each agent used individually, e.g., as a monotherapy. In certain embodiments, the administered amount or dosage of the activated CAR T cells, the additional agent (e.g., second or third agent), or all, is lower (e.g., at least 20%, at least 30%, at least 40%, or at least 50%) than the amount or dosage of each agent used individually. In other embodiments, the amount or dosage of the activated CAR T cells, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect. In further embodiments, the activated CAR T cells described herein can be used in a treatment regimen in combination with surgery, chemotherapy, radiation, an mTOR pathway inhibitor, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, rapamycin, mycophenolic acid, steroids, FR901228, cytokines, or a peptide vaccine, such as that described in Izumoto et al., J. Neurosurg. 108:963-971, 2008.

In one example, the anti-TACI antibodies, antibody-drug conjugates, BiTEs, and/or anti-TACI CARs described herein can be used in combination with a checkpoint inhibitor. Exemplary checkpoint inhibitors include anti-PD-1 inhibitors, anti-CTLA4 inhibitors, anti-PDL1 inhibitors, and anti-TIM3 inhibitors.

In another embodiment, the anti-TACI antibodies, antibody-drug conjugates, BiTEs, and/or anti-TACI CARs described herein can be used in combination with a chemotherapeutic agent.

Efficacy

The efficacy of the anti-TACI antibodies, antibody-drug conjugates, BiTEs, and/or anti-TACI CARs in, e.g., the treatment of a condition described herein, or to induce a response as described herein (e.g., a reduction in cancer cells) can be determined by the skilled clinician. However, a treatment is considered "effective treatment," as the term is used herein, if one or more of the signs or symptoms of a condition described herein is altered in a beneficial manner, other clinically accepted symptoms are improved, or even ameliorated, or a desired response is induced, e.g., by at least 10% following treatment according to the methods described herein. Efficacy can be assessed, for example, by measuring a marker, indicator, symptom, and/or the incidence of a condition treated according to the methods described herein or any other measurable parameter appropriate. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

Efficacy can also be measured by a failure of an individual to worsen as assessed by hospitalization, or need for medical interventions (i.e., progression of the disease is halted). Methods of measuring these indicators are known to those of skill in the art and/or are described herein.

Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy of a given approach can be assessed in animal models of a condition described herein. When using an experimental animal model, efficacy of treatment is evidenced when a statistically significant change in a marker is observed.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior technology or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples, which in no way should be construed as being further limiting.

EXAMPLES

The following are examples of useful methods and compositions. It is understood that various other embodiments may be practiced, given the description provided herein.

Example 1. Generation of Anti-TACI Antibodies

Monoclonal antibodies (mAbs) that specifically bind to transmembrane activator and calcium modulator and cyclophilin ligand interactor (TACI) were generated.

First, mAb-producing cells (i.e., hybridomas) were generated by fusing myeloma cells with B cells. After cell fusion, large numbers of clones were screened and selected on the basis of antigen specificity and immunoglobulin class. Once candidate hybridoma cell lines were identified, the antibodies were validated, and characterized using several downstream functional assays (FIG. 1). The mAb was sequenced and the variable heavy (VH) and variable light (VL) chains were used to produce a second-generation chimeric antigen receptor.

Figure 2:
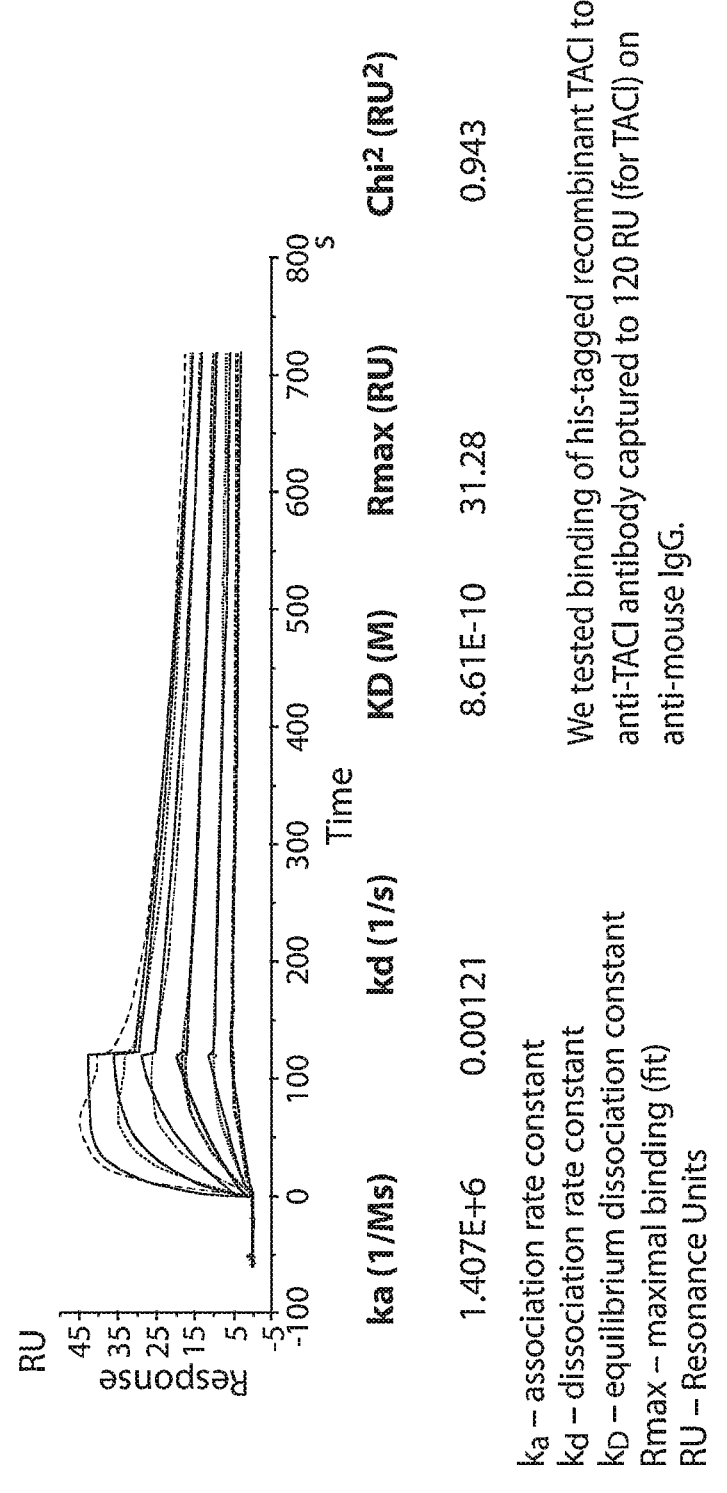
FIG. 2 is a graph showing results of a surface plasmon resonance assay with the anti-TACI antibodies.

The antibodies were analyzed by surface plasmon resonance according to the following procedure (FIG. 2). The binding of his-tagged recombinant TACI to anti-TACI antibody was captured to 120 RU (for TACI) on anti-mouse IgG.

Capture: Antibody was made 1 mg/mL in the running buffer and captured on anti-mouse IgG surface (CM5 chip, 10,000 RU anti-IgG antibody immobilized by standard amine-directed chemistry according to the manufacturer's instructions, GE Healthcare, Cat #BR-1008-38) to achieve 130 RU for TACI analysis.

Running buffer: PBS-P (10 mM sodium phosphate, 150 mM NaCl, 0.005% Tween 20, pH 7.4).

Regeneration buffer: 10 mM glycine, pH 2.1

Flow and injections scheme: Flow: 50 mL/min, 2 min contact time, 5 min dissociation The results of the assay are shown in FIG. 2. Results: $k_a$ (association rate constant)=1.407×10⁶ 1/Ms, $k_d$ (dissociation rate constant)=0.00121 1/s, $K_D$ (equilibrium dissociation constant)=8.61×10⁻¹⁰ M, Rmax (maximal binding (fit))=31.28 RU, and Chi²=0.943 RU². RU: Resonance Units.

Example 2. Design of Anti-TACI Chimeric Antigen Receptors (CARs)

Figure 3:
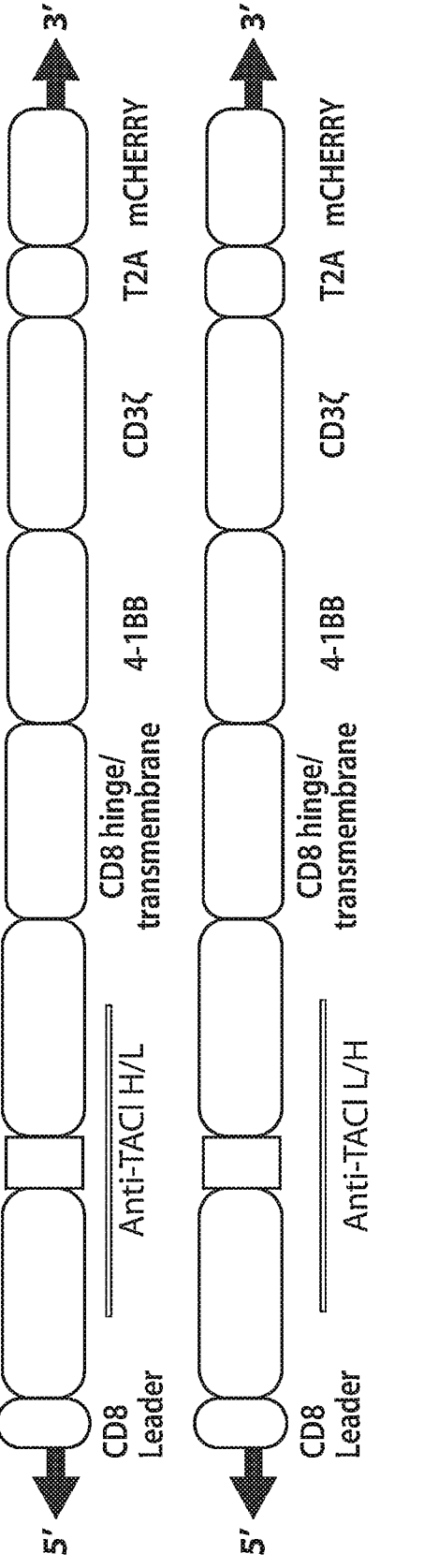
FIG. 3 is a diagram showing the design of anti-TACI CARs referred to herein as "Anti-TACI (H/L)" and "Anti-TACI (L/H)."

Second-generation chimeric antigen receptors (CARs) were designed as shown in FIG. 3. Two anti-TACI CAR constructs were generated, one with the VH N-terminal to the VL of the anti-TACI single chain variable fragment (scFv) (anti-TACI (H/L)), and the other with the VL N-terminal to the VH of the anti-TACI scFv (anti-TACI (L/H)).

The VH and VL sequences included in the CARs were derived from the anti-TACI antibody described in Example 1. Each CAR further includes a CD8 hinge/transmembrane domain, a 4-1BB co-stimulatory domain, and a CD3ζ intracellular signaling domain. CARs were expressed in T cells according to standard methods (see Examples 3 et seq.).

Figure 23:
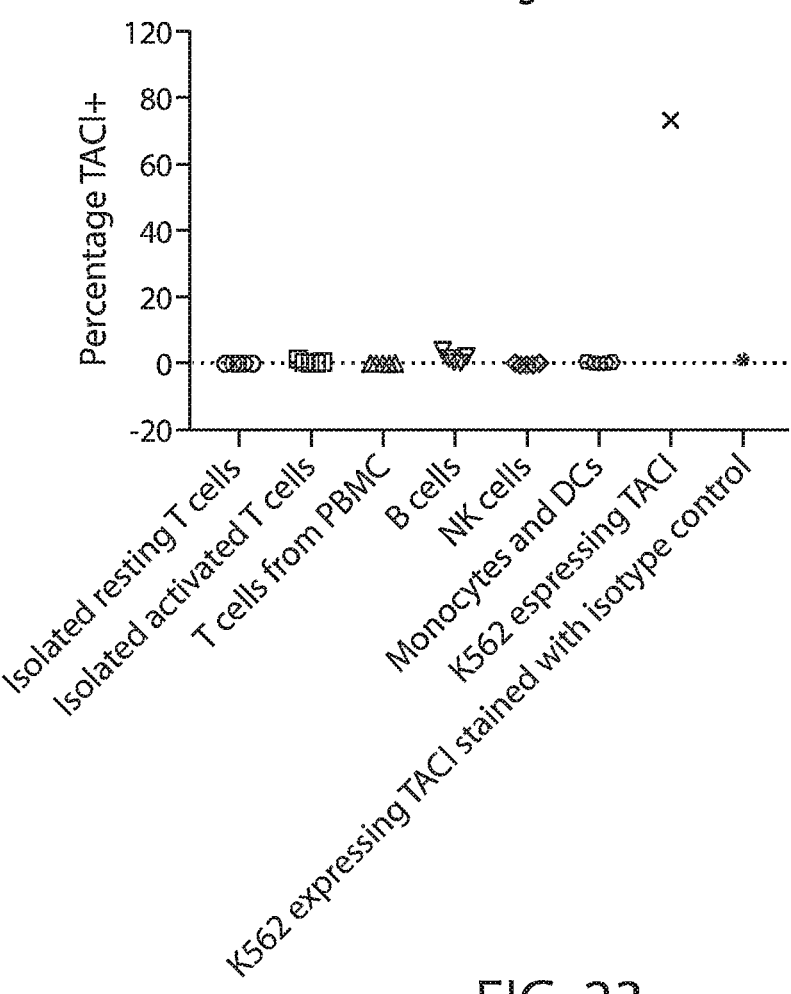
FIG. 23 shows staining of peripheral blood mononuclear cells (PBMCs) with TACI antibody, measured by flow cytometry.

To test potential effects of anti-TACI antibodies on immune cells, peripheral blood mononuclear cells (PBMCs) were incubated with anti-TACI antibody, and binding was measured by flow cytometry. Resultes demonstrated that the anti-TACI antibody did not bind isolated T cells (resting or activated) or various other PBMCs (FIG. 23). K562 over-expressing TACI were used as a positive control.

Figure 24:
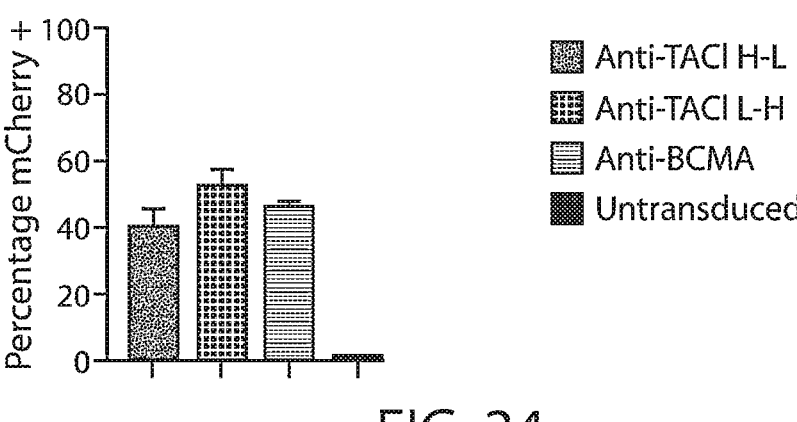
FIG. 24 shows transduction efficiency of normal donor T cells with anti-TACI H-L, anti-TACI L-H, or anti-BCMA, as measured by % mCherry positive cells in flow cytometric analysis.
Figure 25A:
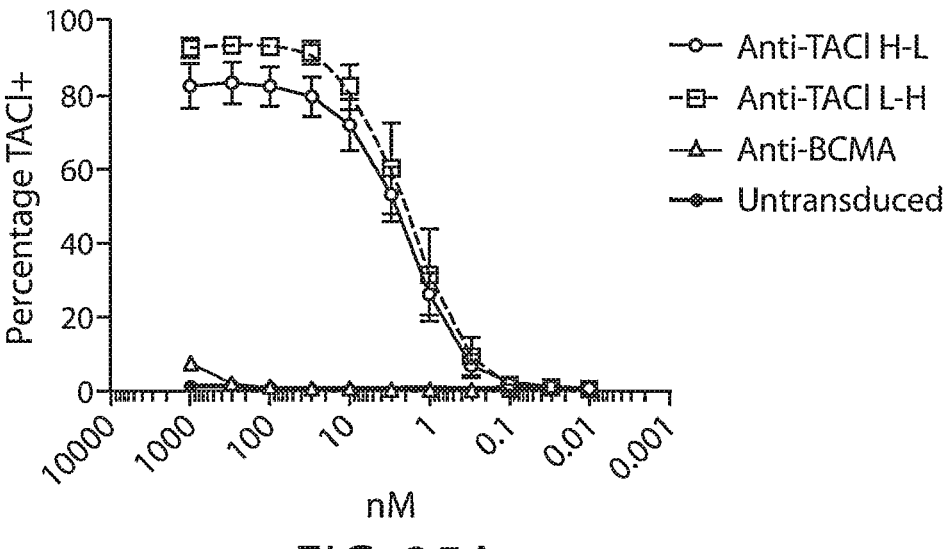
FIGS. 25A-25B show measurements of binding of soluble TACI protein to untransduced T cells, and to T cells expressing anti-TACI H-L, anti-TACI L-H, or anti-BCMA. Cells were incubated with fluorescent soluble TACI protein at various concentrations, after which fluorescence of the cells was measured using flow cytometry, represented as percentage of cells positive for TACI (FIG. 25A) or as median fluorescence intensity (MFI) relative to signal measured in untransduced cells (FIG. 25B).
Figure 25B:
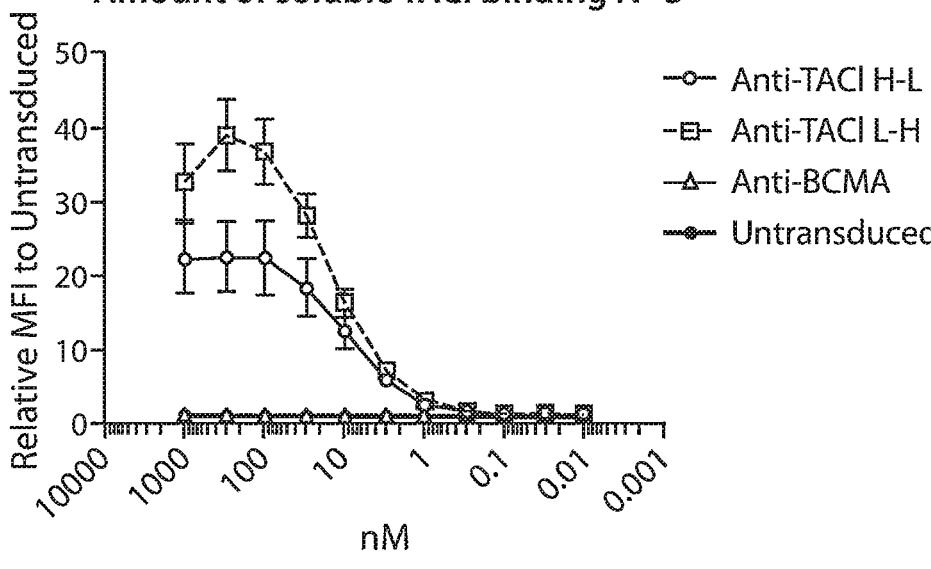

To evaluate the expression, binding efficacy, and binding specificity of anti-TACI CARs, normal donor T cells were transduced with anti-TACI H-L, anti-TACI L-H, or anti-BCMA and transduction efficiency was evaluated by measuring the percentage of each T cell population positive for mCherry expression by flow cytometry. Results demonstrated that transduction efficiency of both anti-TACI CAR constructs is high and similar to anti-BCMA CAR (FIG. 24). To compare binding efficiency and specificity of different CARs, T cells expressing each CAR construct were incubated with fluorescently-labeled soluble TACI and analyzed by flow cytometry. Results demonstrated that anti-TACI L-H CARs have higher binding affinity for soluble TACI than anti-TACI H-L CARs, and anti-BCMA CARs show no binding to soluble TACI protein (FIGS. 25A and 25B).

Figure 27A:
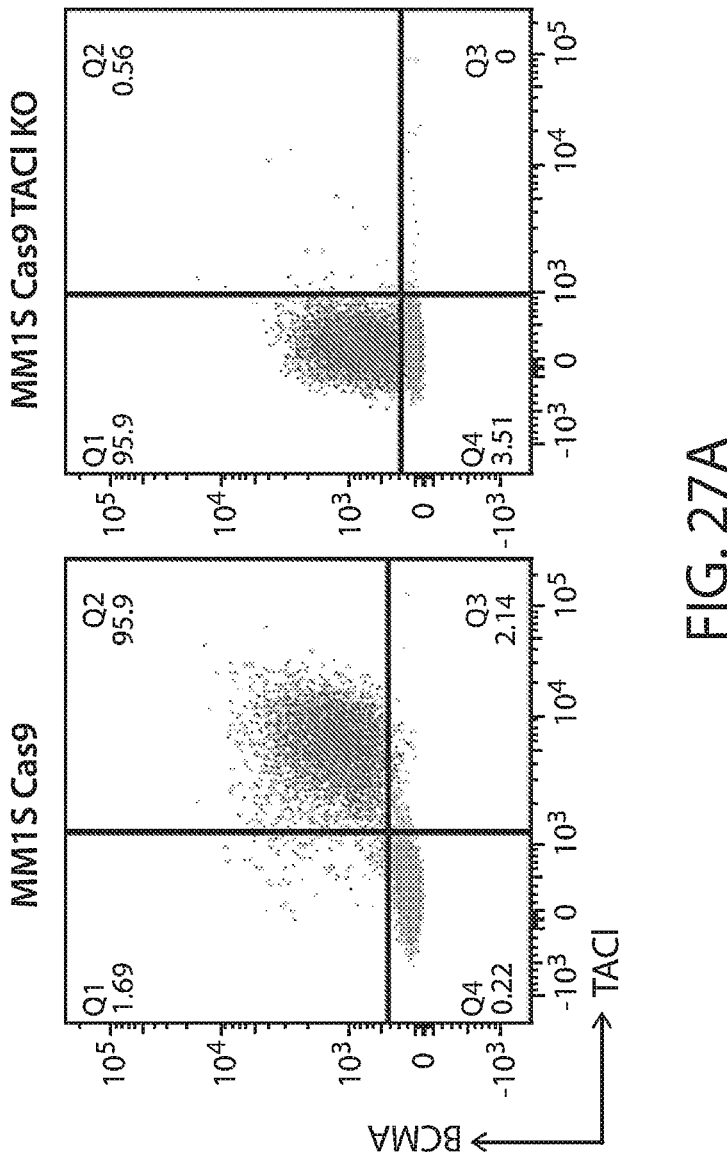
FIGS. 27A-27B show effects of anti-TACI CAR T cells are specific to TACI-expressing tumor cells.
Figure 27B:
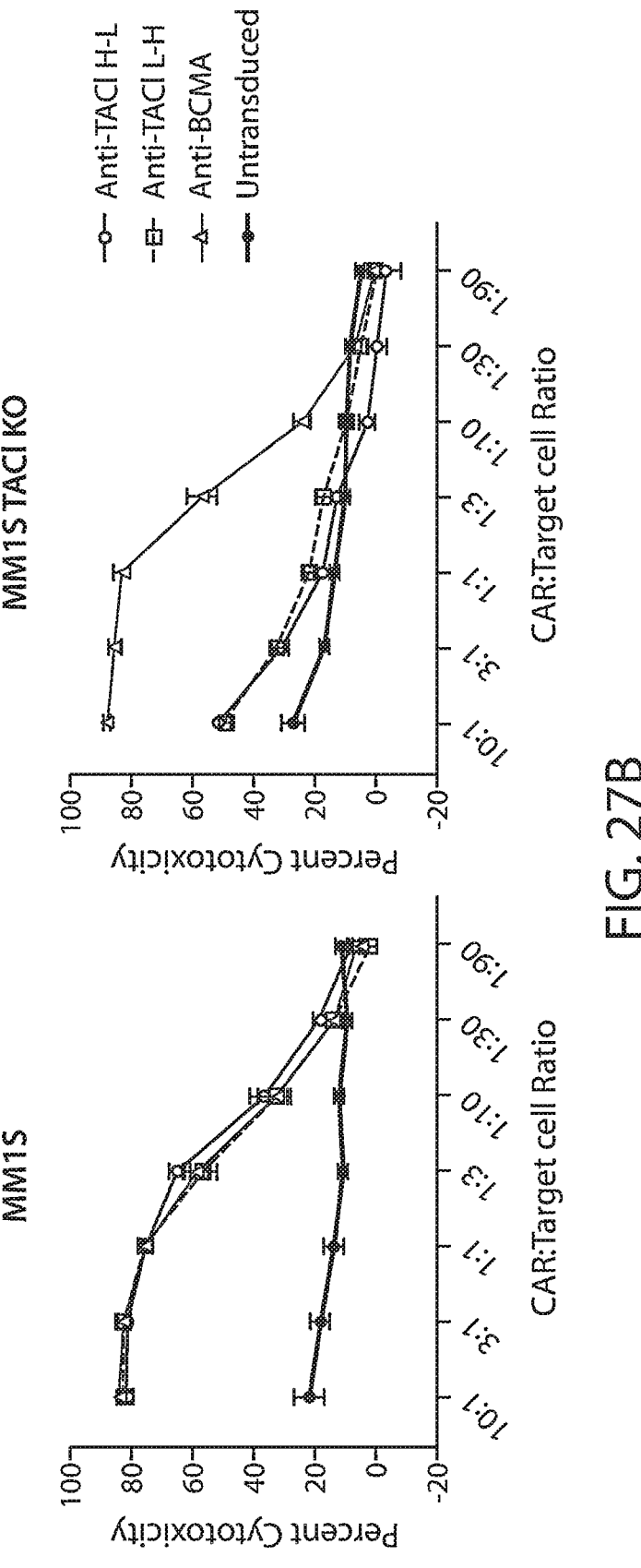

To further evaluate the specificity of anti-TACI CARs for TACI, MM1S cancer cells expressing Cas9 were generated. Cells expressing TACI or deficient in TACI via Cas9 knockout were generated. FIG. 27A shows that Cas9 knockout of TACI was successful. MM1S Cas9 and MM1S Cas9 TACI knockout (KO) cells were incubated with T cells which were either untransduced or transduced with anti-TACI H-L, anti-TACI L-H, or anti-BCMA and cytotoxicity was measured. Results demonstrate that anti-TACI CARs are specific to TACI and T cells expressing them have little efficacy against TACI KO cells, against which only the positive control anti-BCMA CAR T cells had substantial cytotoxicity (FIG. 27B).

Example 3. BCMA and TACI Antigen Expression

Figure 4:
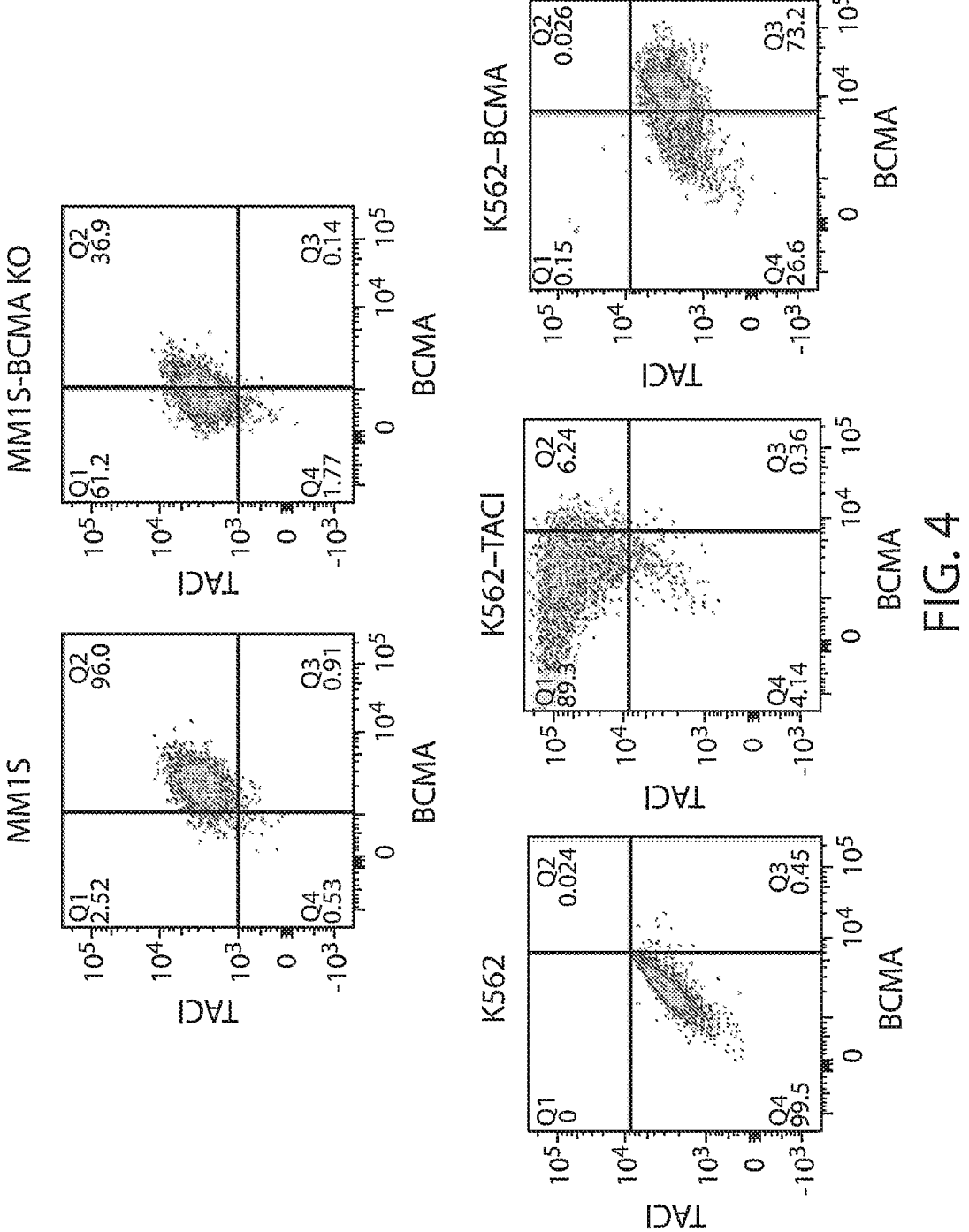
FIG. 4 is a series of graphs showing BCMA and TACI expression on MM1S, MM1S BCMA-knockout, K562, K562-TACI, and K562-BCMA cell lines.

The multiple myeloma cell line MM1S were used in the experiments described herein. MM1S expressed both TACI and B cell maturation antigen (BCMA). A BCMA-knockout MM1S cell line was generated, as well as a K562 cell line expressing TACI and a K562 cell line expressing BCMA (FIG. 4).

Figure 5:
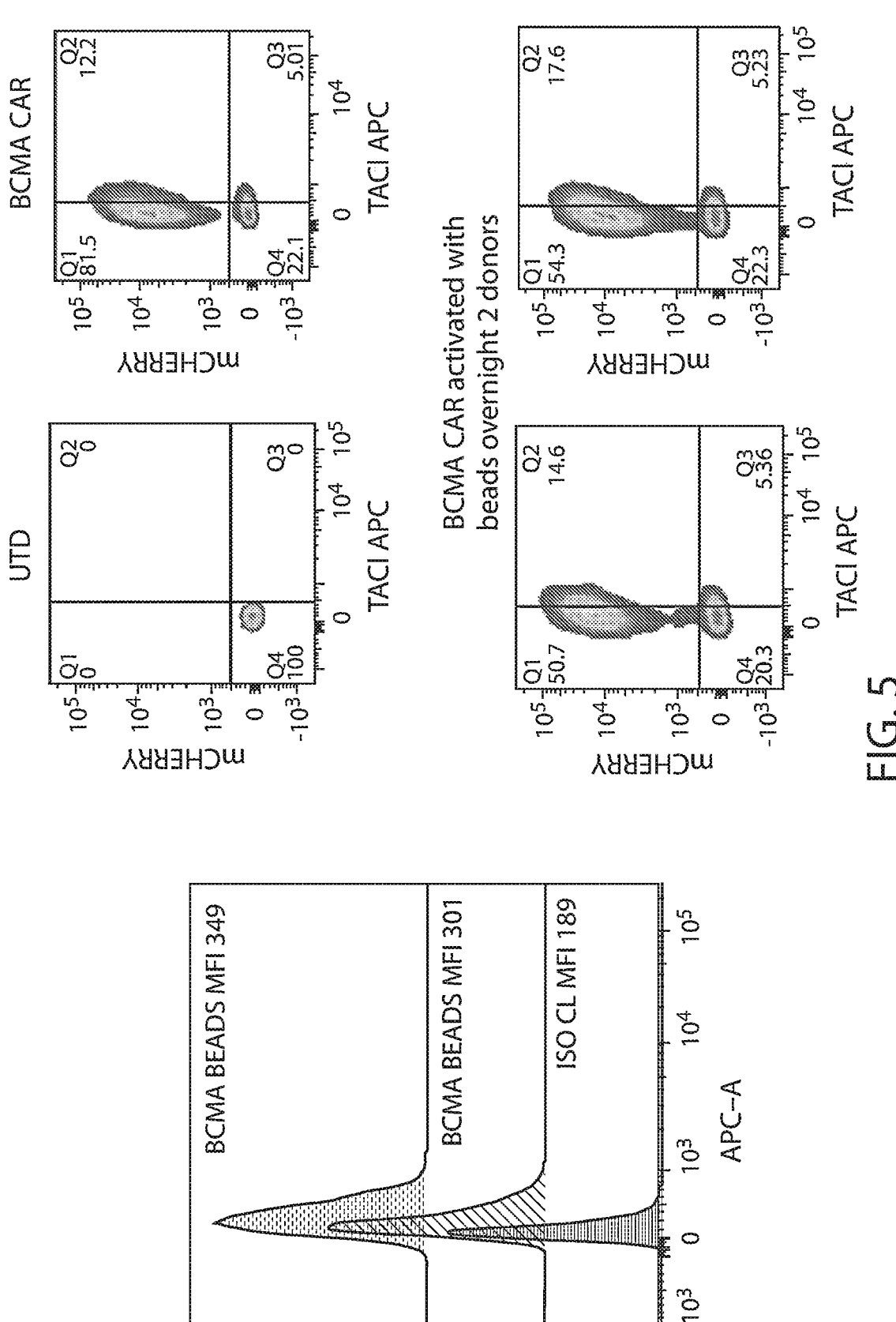
FIG. 5 is a series of graphs showing TACI expression in T cells.

Because TACI is expressed in activated T cells, it was evaluated if rested CAR T cells or activated CAR T cells (activated with beads) express or upregulate the expression of TACI. As shown in FIG. 5, there is some expression on rested cells but very small changes when the CAR T cells are activated.

Figure 6:
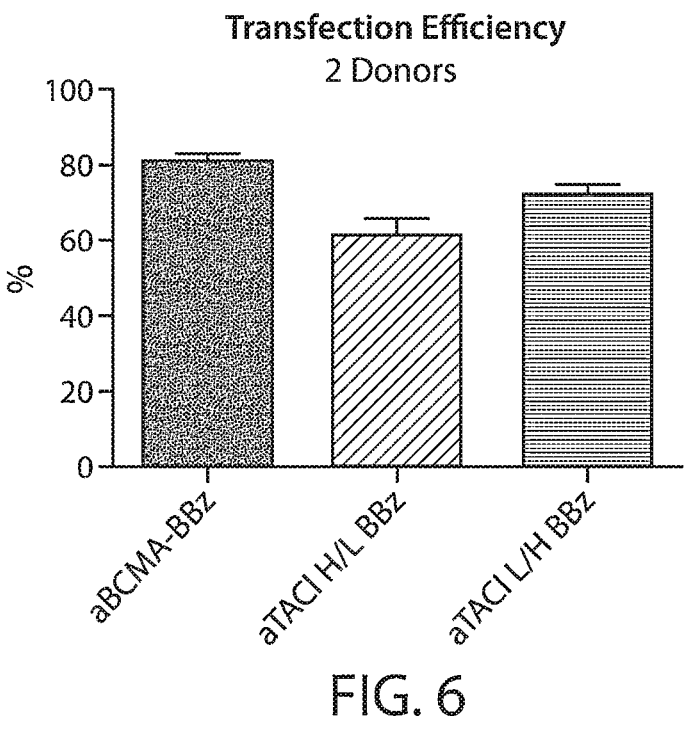
FIG. 6 is a graph showing transfection efficiency of anti-BCMA, anti-TACI (H/L), and anti-TACI (L/H) CAR T cells as measured by mCherry expression. Multiplicity of infection (MOI)=10.

Example 4. Transfection Efficiency and Killing Activity of Anti-TACI CAR T Cells The transfection efficiency of the anti-TACI CAR T cells is measured by the quantification of mCherry-positive cells, as the CAR T cells have been engineered to express mCherry (see FIG. 3). As evident in FIG. 6, the transfection efficiency of an anti-BCMA-BBz CAR is very similar to the transfection efficiency of both TACI CARs. Target multiplicity of infection (MOI)=10.

Figure 7:
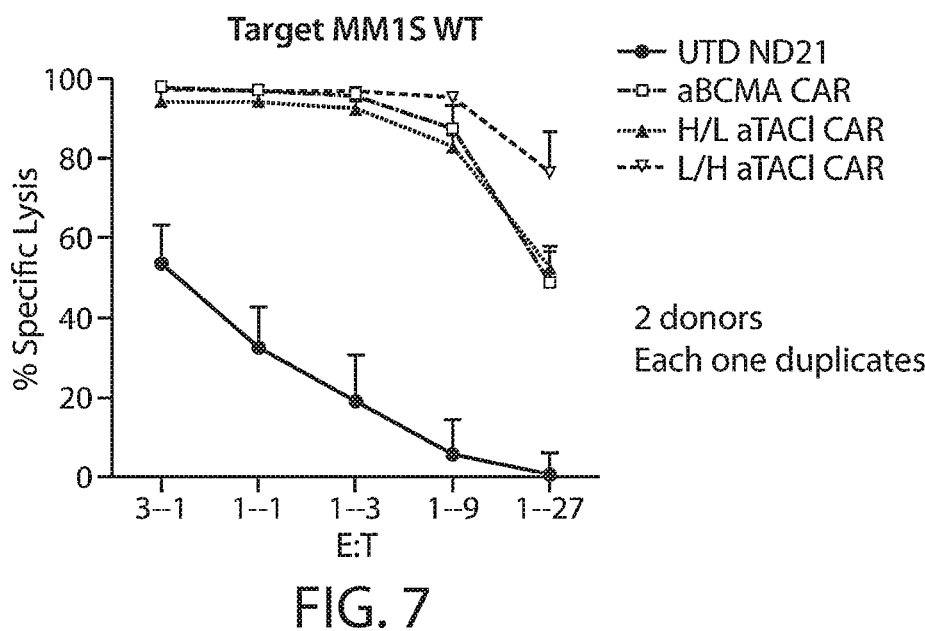
FIG. 7 is a graph showing killing activity of untransduced (UTD), anti-BCMA, anti-TACI (H/L), and anti-TACI (L/H) CAR T cells using MM1S cells as the target cells.

A killing assay was performed to evaluate the activity of the anti-TACI (H/L) and (L/H) CAR T cells compared to anti-BCMA CAR and untransduced (UTD) T cells. The results of the assay are presented in FIG. 7. The CAR T cells were incubated overnight with the target cells at various effector:target (E:T) ratios indicated in FIG. 7. The target cells used were MM1S cells that express both BCMA and TACI. It was demonstrated that anti-BCMA CAR and both anti-TACI CAR T cells are excellent killers. At low E:T ratios, the anti-TACI (L/H) CAR T cells appeared to be more efficient.

Figure 8:
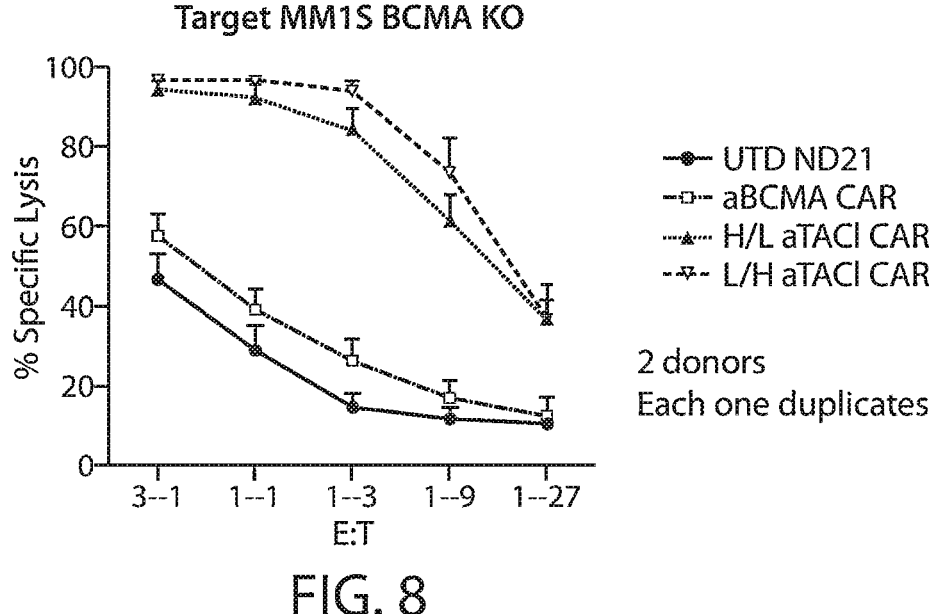
FIG. 8 is a graph showing killing activity of UTD, anti-BCMA, anti-TACI (H/L), and anti-TACI (L/H) CAR T cells using MM1S BCMA-knockout cells as the target cells.

A similar killing assay was performed with the anti-BCMA CAR, anti-TACI (H/L) CAR, anti-TACI (L/H) CAR, and UTD T cells as described above using the MM1S BCMA-knockout cell line generated in Example 3 as the target cells. It was observed that the anti-BCMA CAR T cells were unable to kill the MM1S BCMA-knockout cell line, while both anti-TACI CAR T cells specifically recognized TACI, killing the targets (FIG. 8).

Example 5. Immunophenotyping of CAR T Cells

Figure 9:
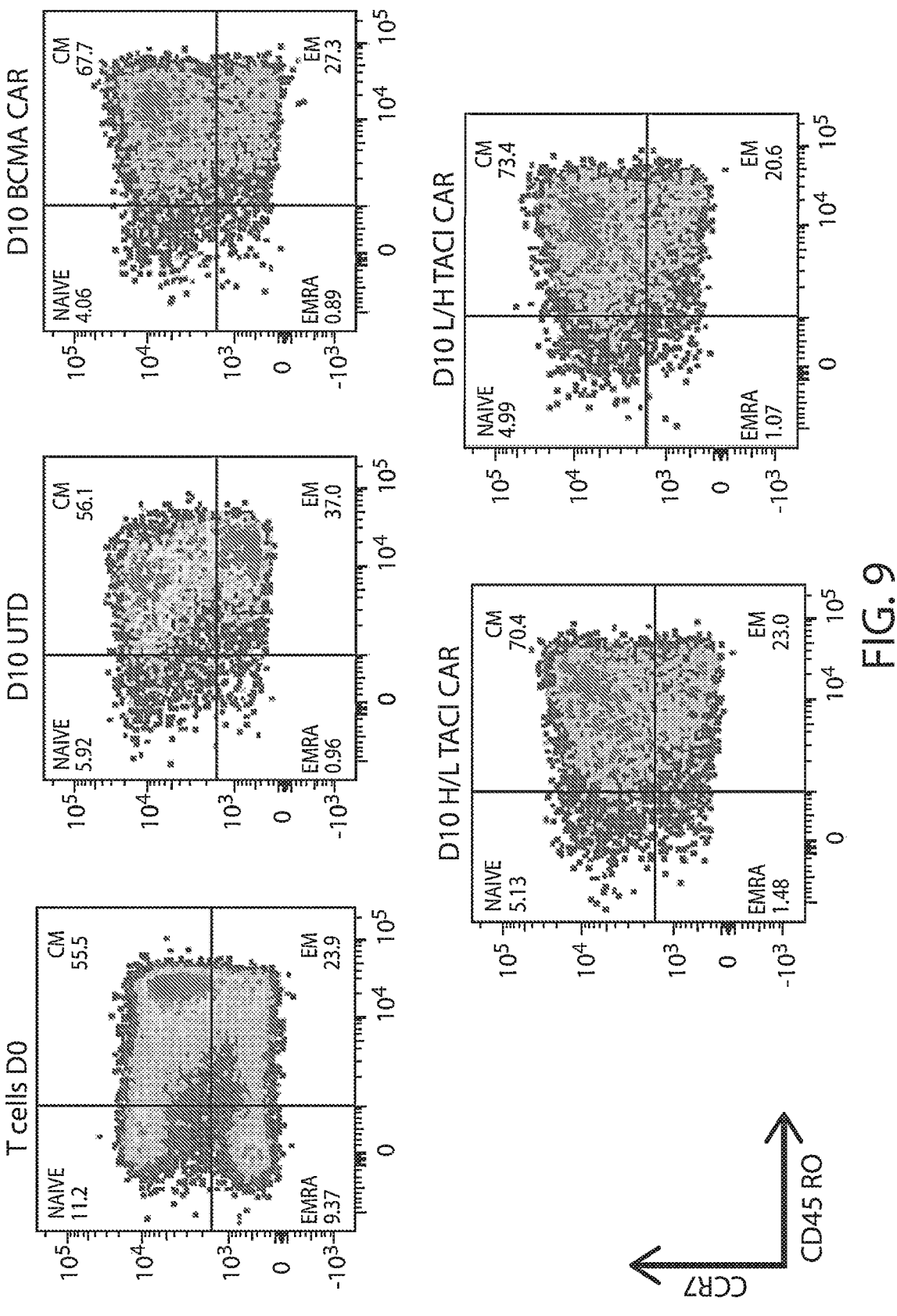
FIG. 9 is a series of graphs showing CD45RO and CCR7 expression on T cells to determine T cell immunophenotype (e.g., naïve T cells, central memory (CM) T cells, effector memory (EM) T cells, and late effector T cells (EMRA)). It is observed that the CM T cell population is enriched.

FIG. 9 shows T cells labeled for CD45RO and CCR7, which allows for characterization of 4 functional distinct populations: naïve, central memory (CM), effector memory (EM), and late effector (EMRA) T cells. As is typically observed with second-generation 4-1BB CARs, the CM population of T cells is enriched. When comparing the anti-BCMA CAR with both anti-TACI CARs, similar results were observed.

Figure 10:
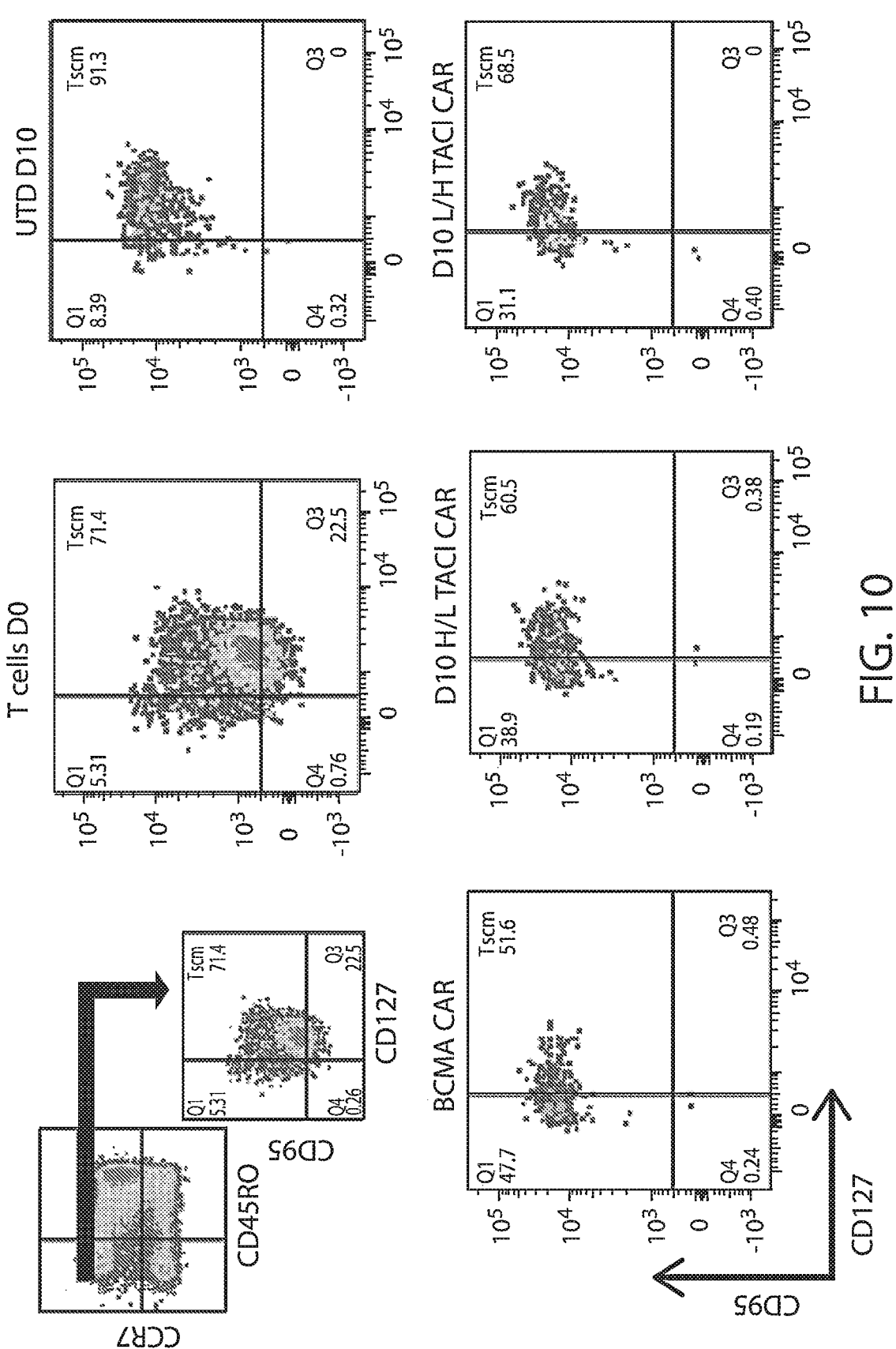
FIG. 10 is a series of graphs showing CD95 and CD127 expression on the naïve T cell population (i.e., CD45− CCR7+ T cells) identified in FIG. 9. CD95 and CD127 are biomarkers for the T stem cell memory (TSCM) population.

A population previously described important for long term memory in the immune system is the T Stem Cell Memory (TSCM) population, which is defined by specific markers from the naïve population (CD45– CCR7+) shown in FIG. 9. The markers specific to the TSCM population are CD95 and CD127. It is shown in FIG. 10 that anti-TACI CAR T cells have a TSCM population.

Example 6. Degranulation and Specific Binding of CAR T Cells

Figure 11:
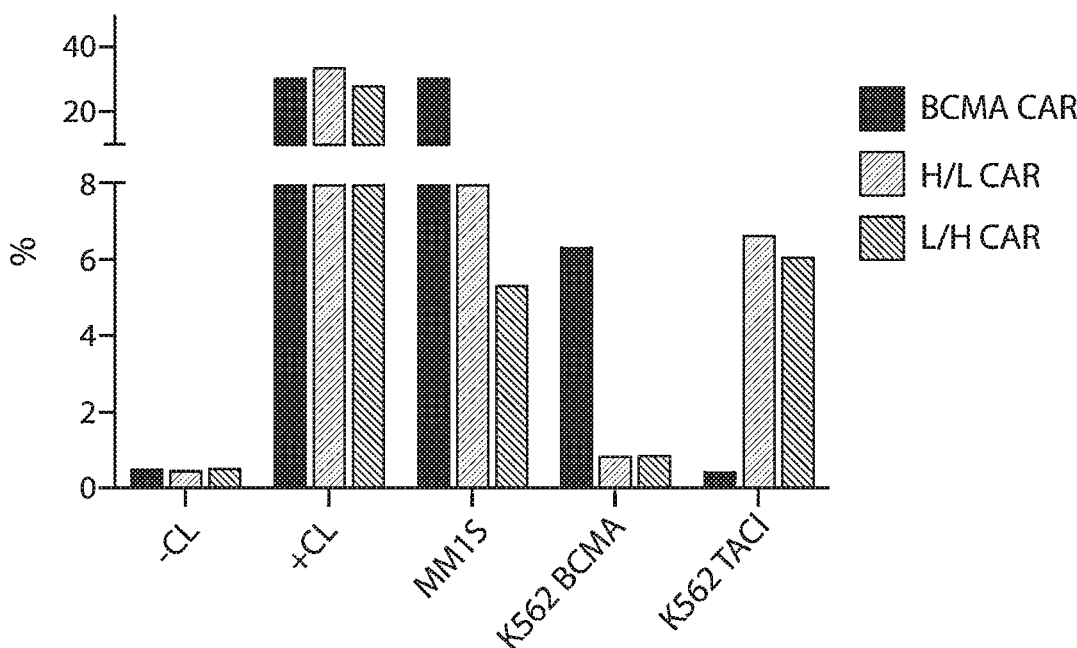
FIG. 11 is a graph showing CD107a expression of anti-BCMA, anti-TACI (H/L), and anti-TACI (L/H) CAR T cells. CD107a is a marker of cytotoxic degranulation.

BCMA and TACI CAR T cells were stained with anti-CD107a antibody (protein transporter inhibitor was added) and left alone (negative control: –CL), co-incubated with different targets, or activated with PMA/ionomycin (positive control: +CL) for 6 hours. Flow cytometry was performed and the live CAR T cells were gated to evaluate expression of CD107a, a marker of cytotoxic degranulation. Results are shown in FIG. 11. It was observed that anti-TACI CAR T cells degranulate specifically in response to TACI+ targets, but not BCMA+/TACI– targets.

Figure 12A:
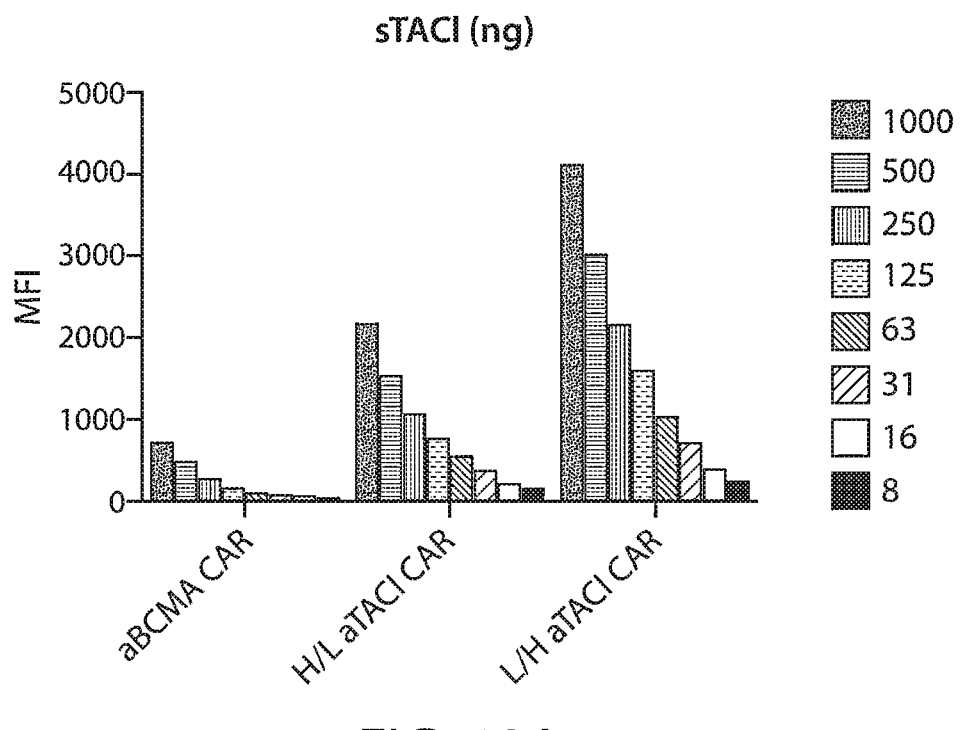
FIGS. 12A-12C are a series of graphs showing binding of anti-BCMA, anti-TACI (H/L), and anti-TACI (L/H) CAR T cells to soluble TACI (sTACI) (FIG. 12A), soluble BCMA (sBCMA) (FIG. 12B), and soluble APRIL (sAPRIL) (FIG. 12C).
Figure 12B:
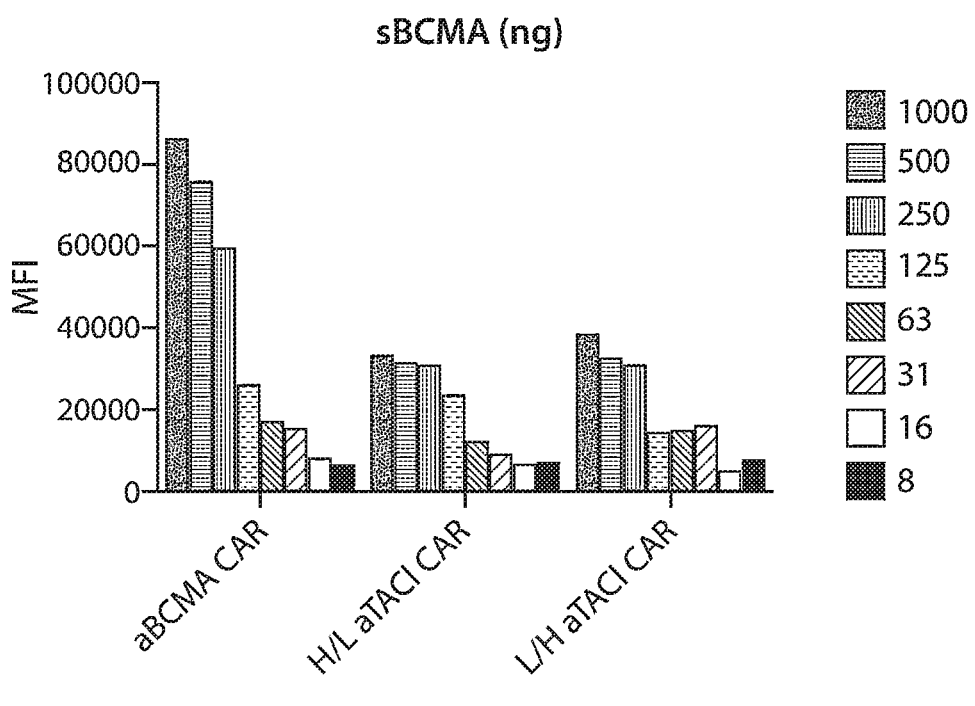
Figure 12C:
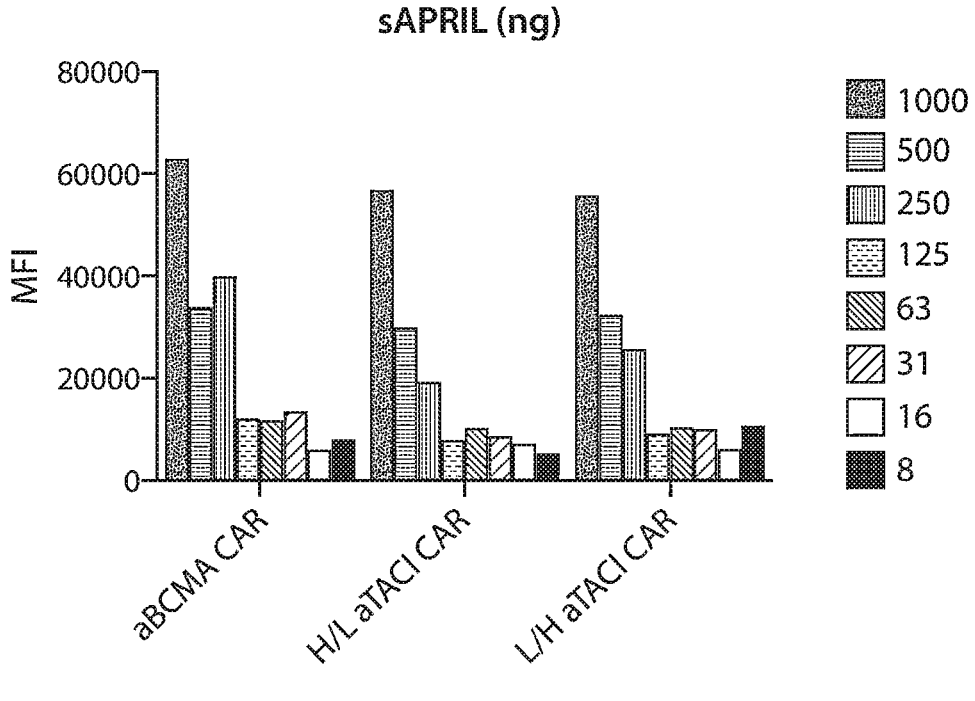

The anti-BCMA, anti-TACI (H/L), and anti-TACI (L/H) CAR T cells were evaluated for their capabilities to bind to soluble TACI (sTACI), soluble BCMA (sBCMA), and soluble APRIL (sAPRIL) was determined. T cells were washed 4 times in PBS 4% BSA, and incubated with labeled protein on ice at 4° C. for 40 min. After incubation, cells were washed twice with FACS buffer and flow cytometry was performed gating on live, CAR T cells to calculate protein binding. The results are shown in FIGS. 12A-12C. As evident in FIG. 12A, anti-TACI (L/H) CAR T cells have higher binding efficiency to soluble TACI than anti-TACI (H/L) CAR T cells. In FIG. 12B, it is demonstrated that both anti-TACI CAR T cells have negligible binding to BCMA. Finally, FIG. 12C shows that anti-BCMA and both anti-TACI CAR T cells have similar binding efficiency to soluble APRIL.

Figures 13A, 13B:
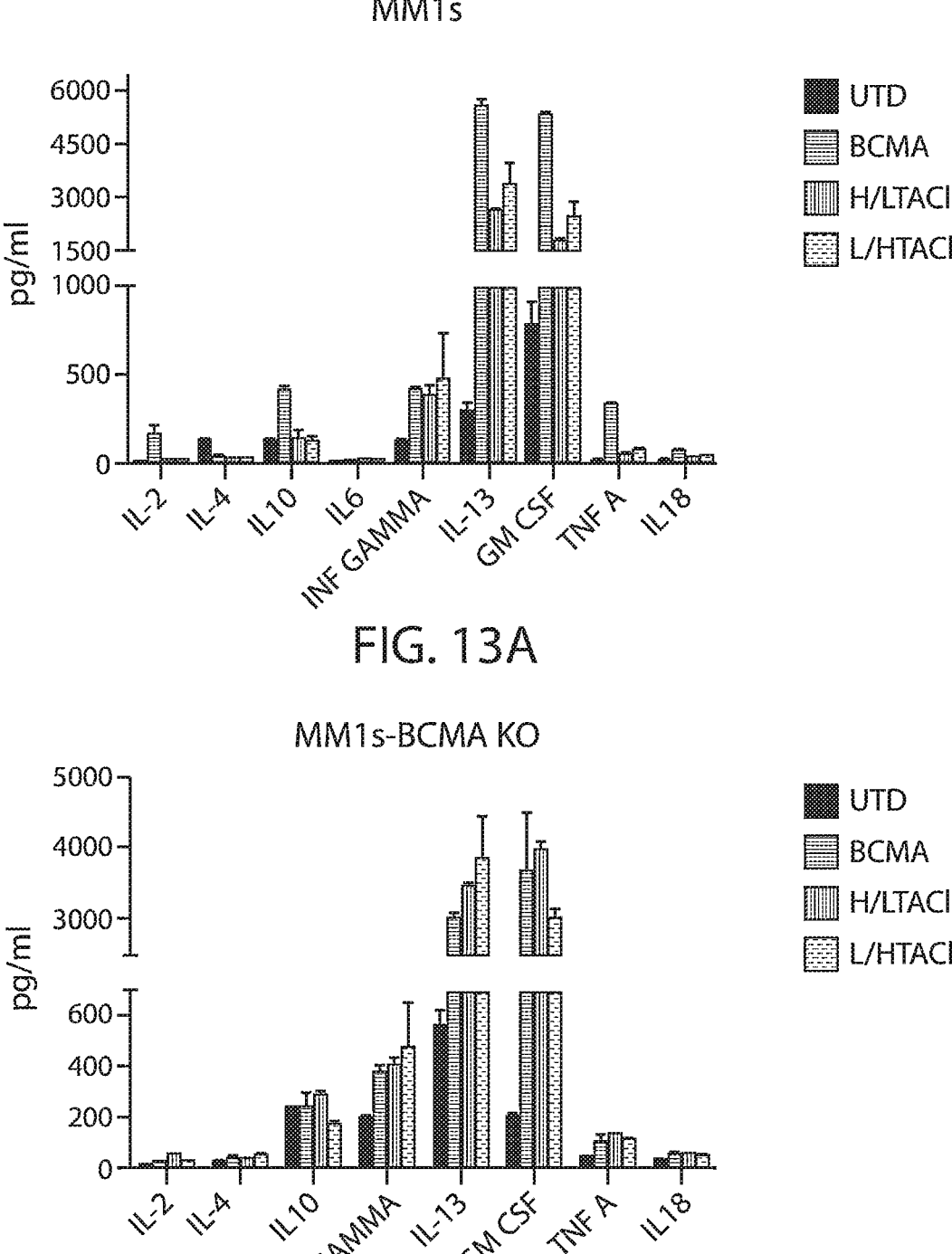
FIGS. 13A-13E are a series of graphs showing cytokine production of anti-BCMA, anti-TACI (H/L), and anti-TACI (L/H) CAR T cells incubated with MM1S target cells (FIG. 13A), MM1S BCMA-knock out cells (FIG. 13B), K562-BCMA cells (FIG. 13C), K562-TACI cells (FIG. 13D), and U266 cells (FIG. 13E).
Figure 13C:
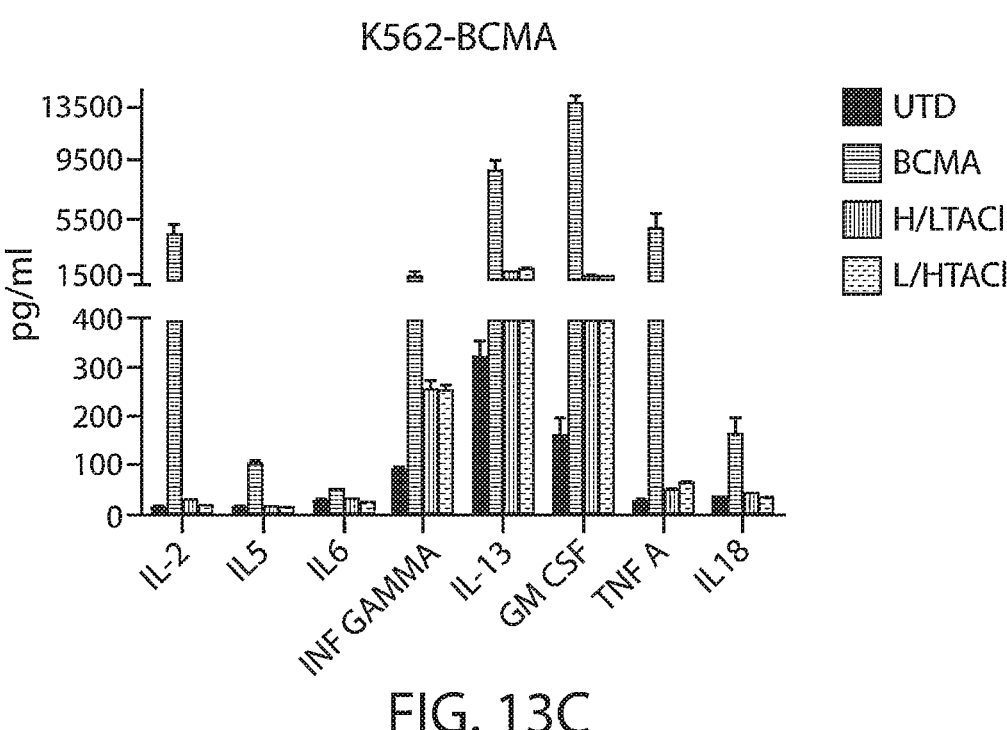
Figure 13D:
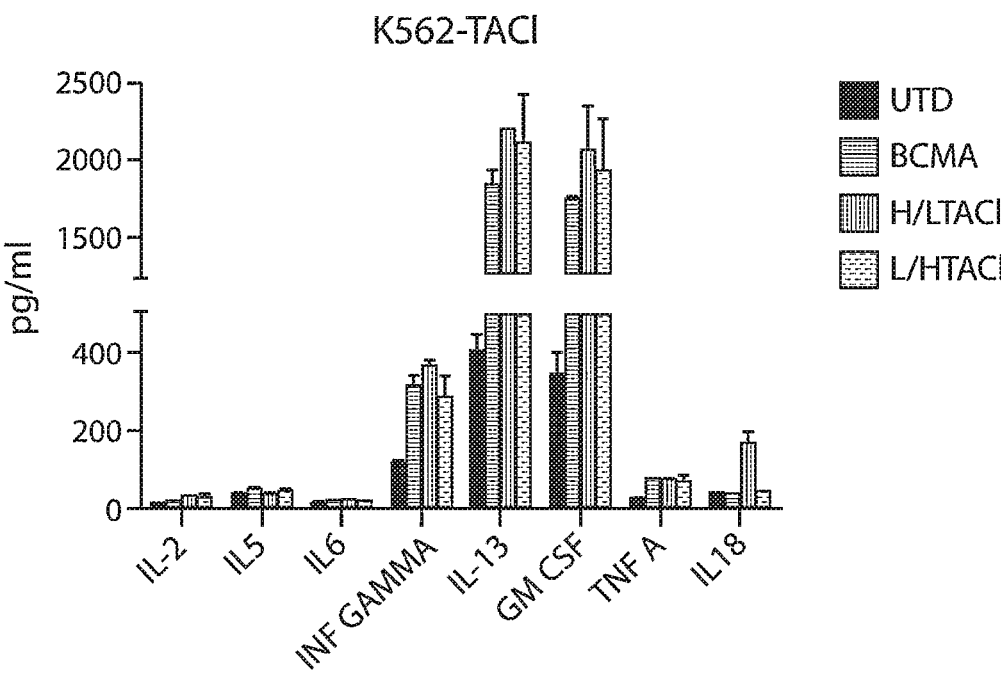
Figure 13E:
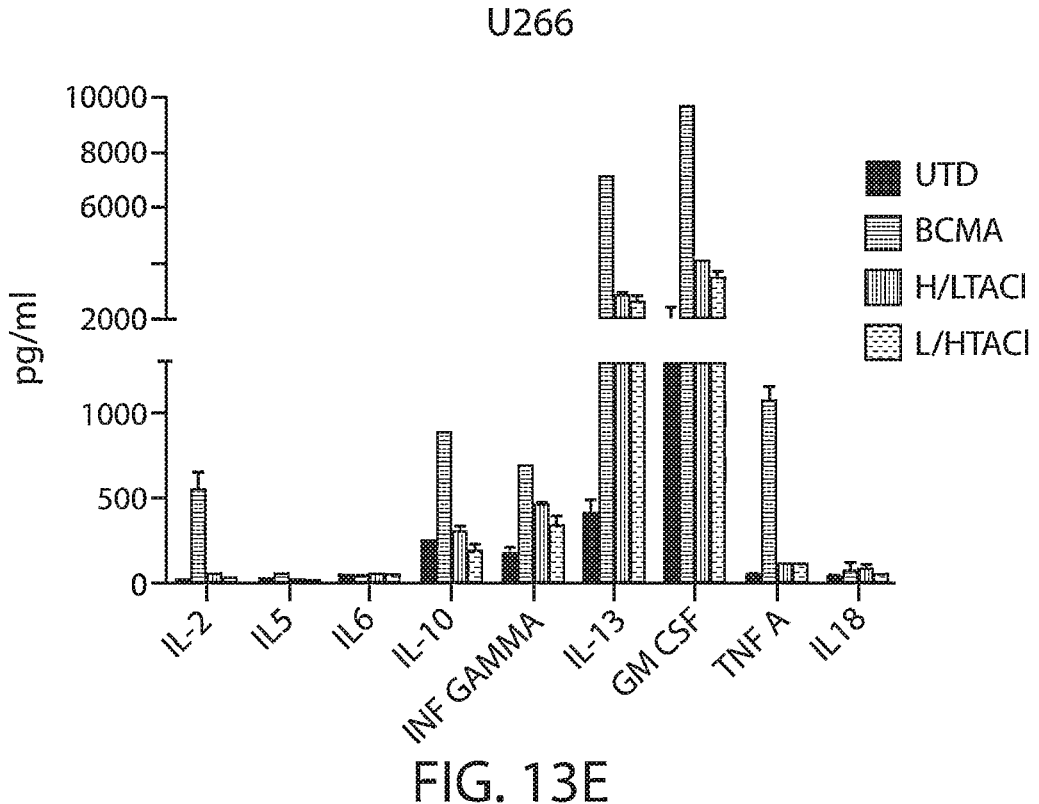

Example 7. Cytokine Production and Long-Term Proliferation of Anti-TACI CAR T Cells Cytokine production of anti-BCMA and both anti-TACI CAR T cells was evaluated by incubating the CAR T cells with the specified targets (MM1S or MM1S BCMA-knock-out cell lines). Untransduced cells were used as the control. Levels of cytokine production are shown in FIGS. 13A and 13B. The anti-TACI CAR T cells were demonstrated to produce cytokines in response to both MM1S and MM1S BCMA-knockout cells. Similarly, the cytokine production of anti-BCMA and both anti-TACI CAR T cells was evaluated, this time using K562-TACI and K562-BCMA cell lines as the targets (FIGS. 13C and 13D). Both anti-TACI CAR T cells produce cytokines in response to target expressing TACI more than they do in response to targets expressing BCMA. Finally, cytokine production of the CAR T cells were evaluated with U266 cells, another multiple myeloma cell line. Results are shown in FIG. 13E.

Figure 14:
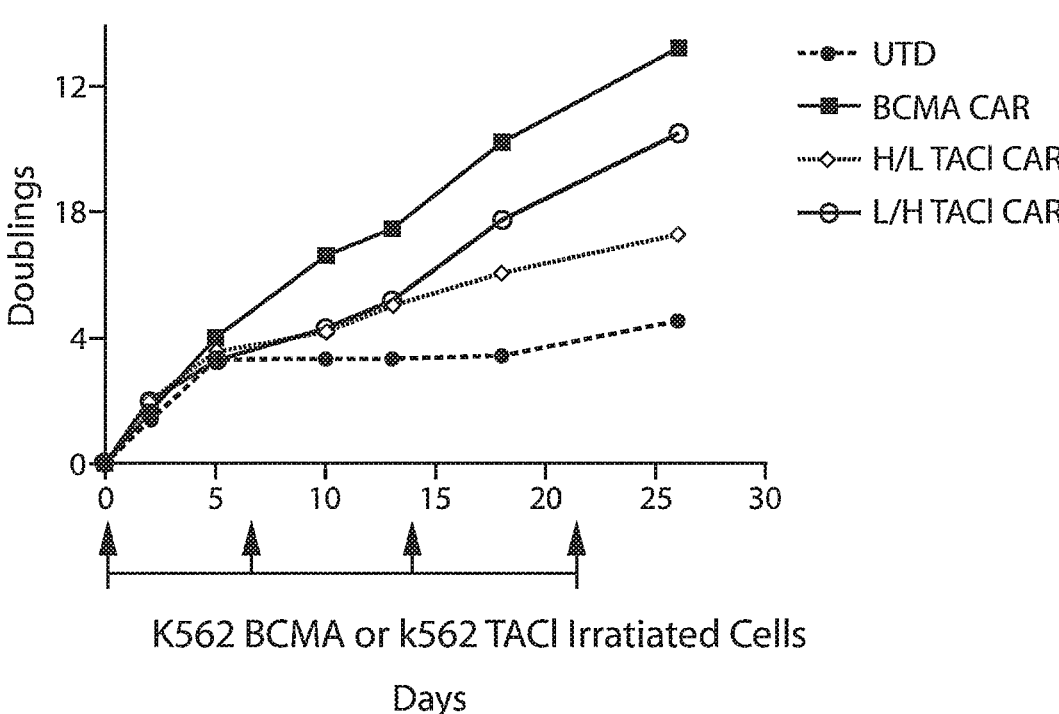
FIG. 14 is a graph showing population doubling of anti-BCMA, anti-TACI (H/L), and anti-TACI (L/H) CAR T cells in response to stimulation with K562-expressing target cells.

Furthermore, it was demonstrated that anti-TACI CAR T cells can undergo long-term proliferation in vitro when stimulated with K562 target cells. The CAR T cells were stimulated on the days indicated by the arrows, and the population doubling of the CAR T cells is shown in FIG. 14.

Example 8. Anti-TACI CAR T Cells In Vivo

Figure 15:
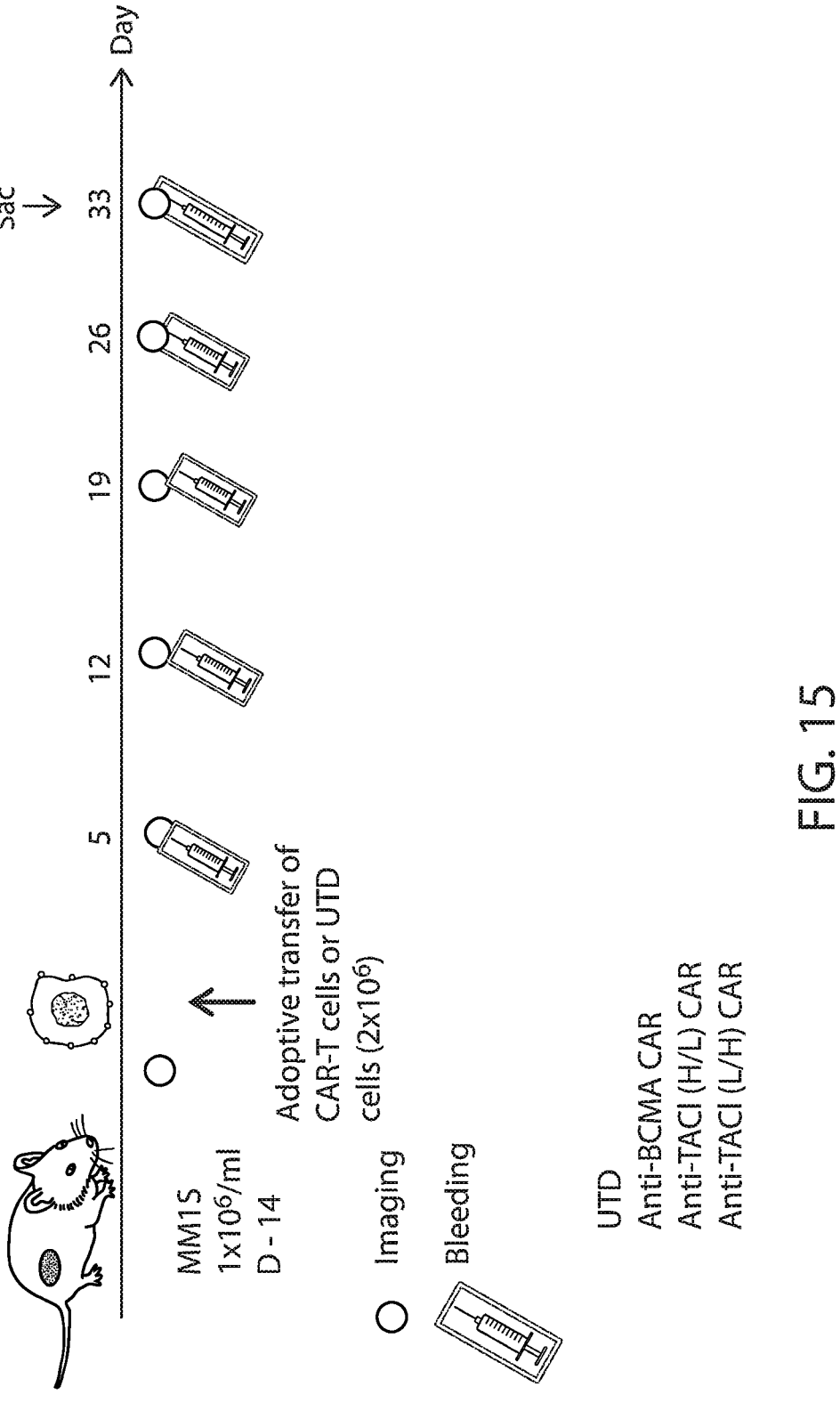
FIG. 15 is a diagram showing the experimental design testing UTD, anti-BCMA, anti-TACI (H/L), and anti-TACI (L/H) CAR T cells in vivo. Mice are injected intravenously (i.v.) with 1×10⁶ MM1S cells. After two weeks, mice are injected with 2×10⁶ CAR T or UTD cells. Bioluminescence images are taken twice per week.
Figure 16A:
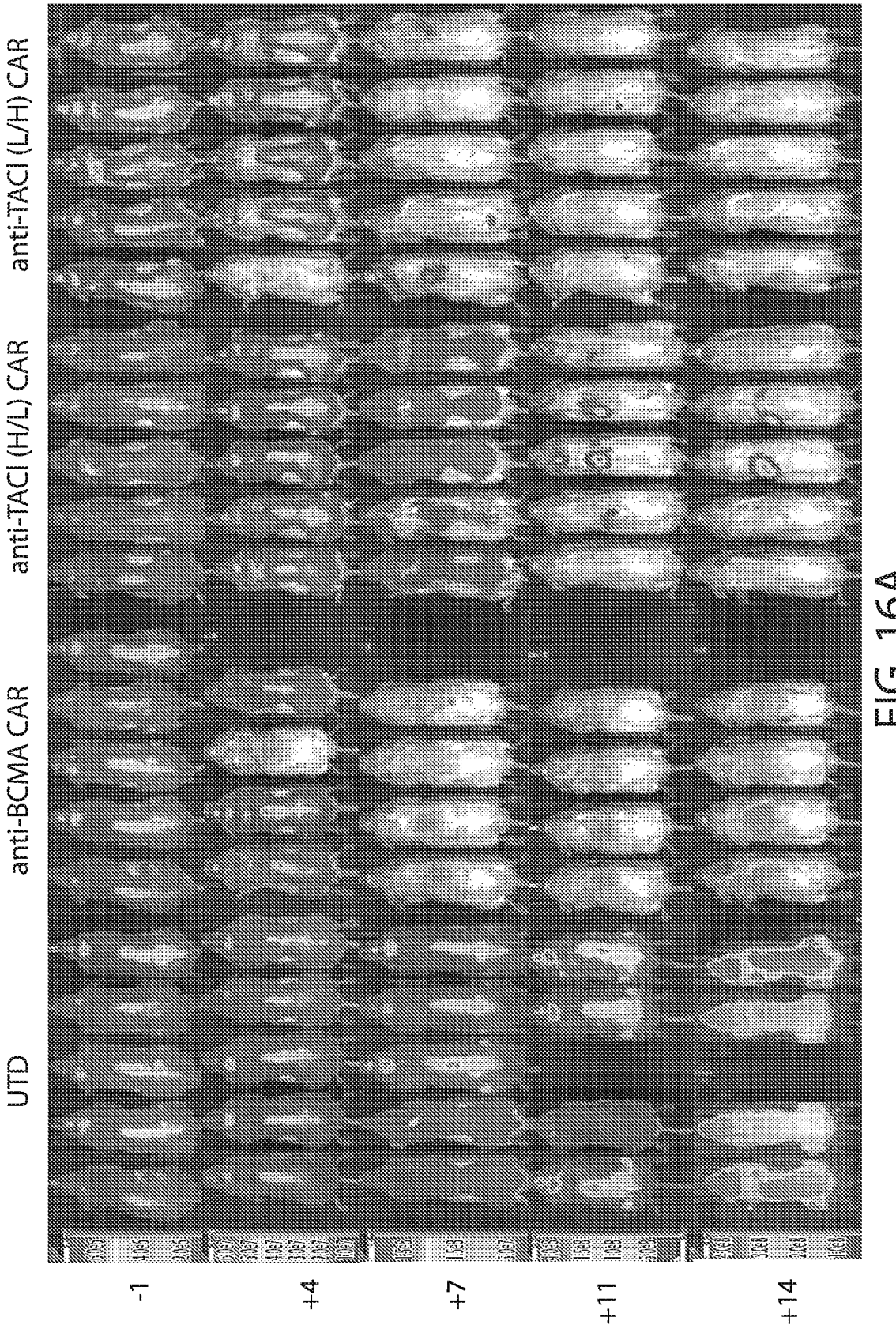
FIGS. 16A and 16B are images taken by bioluminescence imaging showing tumor burden in mice.
Figure 16B:
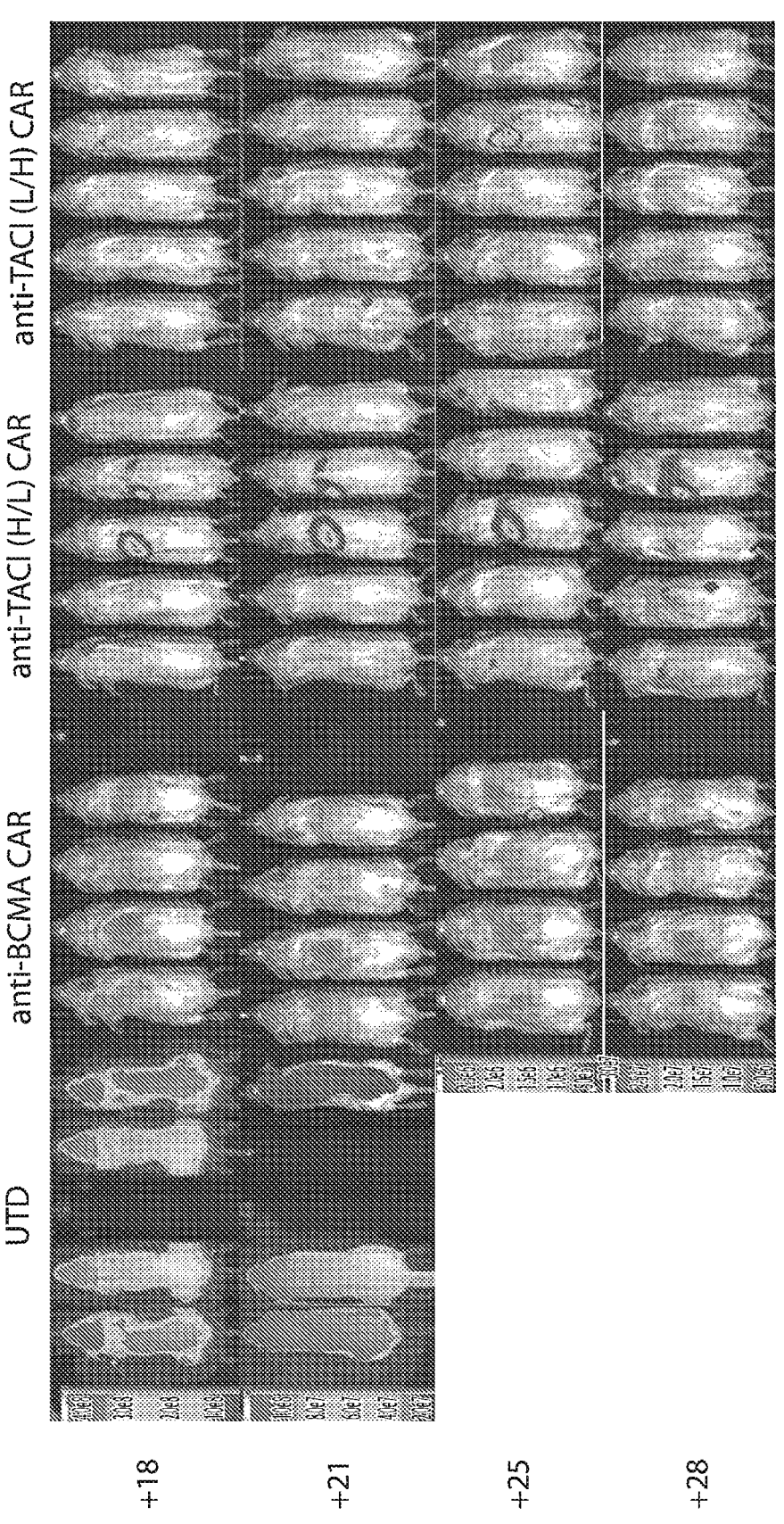
Figure 17:
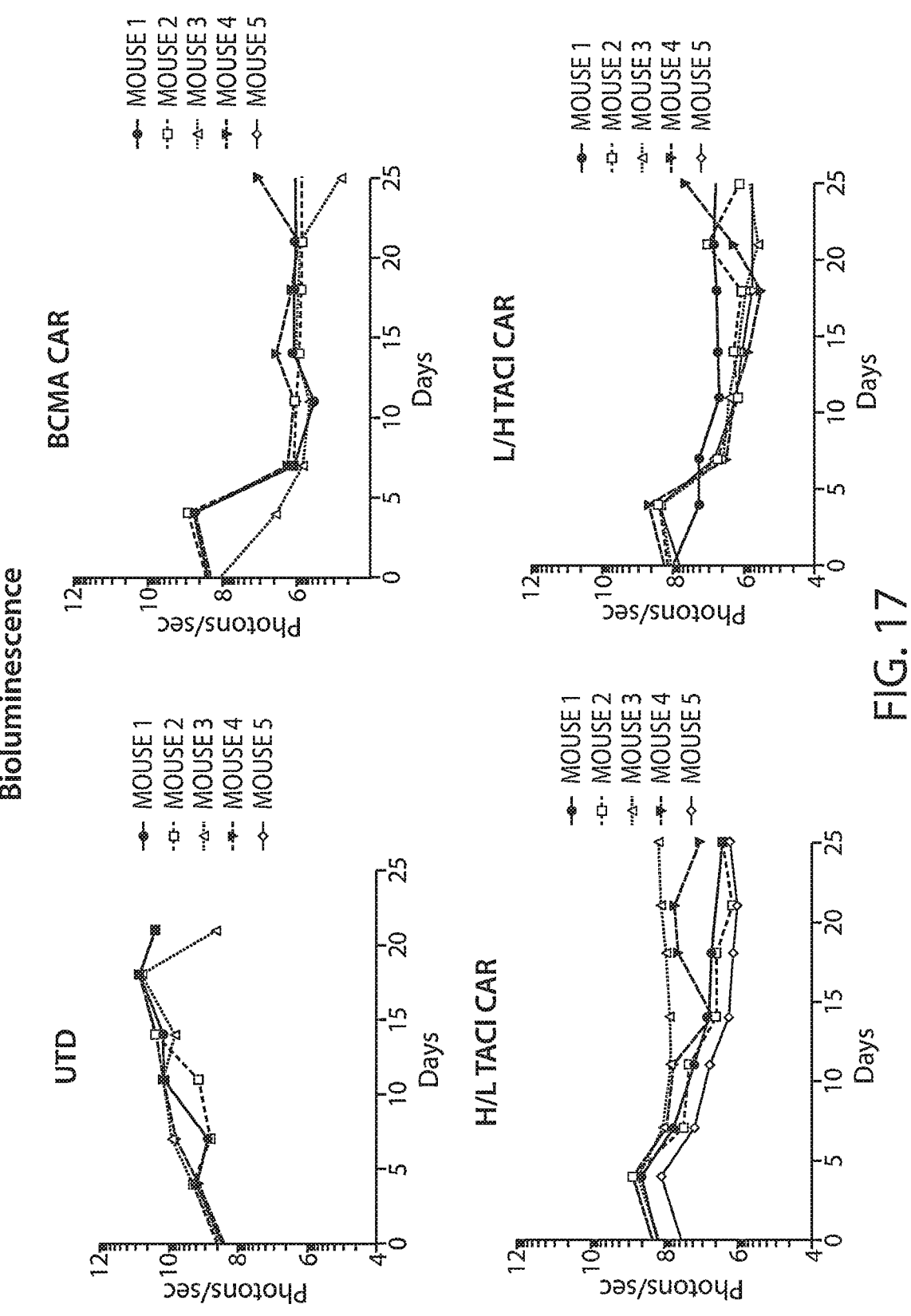
FIG. 17 is a graph showing quantification of tumor burden in mice measured by bioluminescence (photons/sec).

The experimental design of an in vivo experiment using the anti-TACI CAR T cells is shown in FIG. 15. One million MM1S cells were injected intravenously (i.v.) into mice. After 2 weeks, mice were injected with 2 million of CAR T cells or UTD cells. Images were taken twice per week and bioluminescence was quantified. Bioluminescence images are shown in FIGS. 16A and 16B. In FIG. 17, bioluminescence was quantified by photos/sec and is presented in the four graphs for each CAR T cell used.

Figure 18:
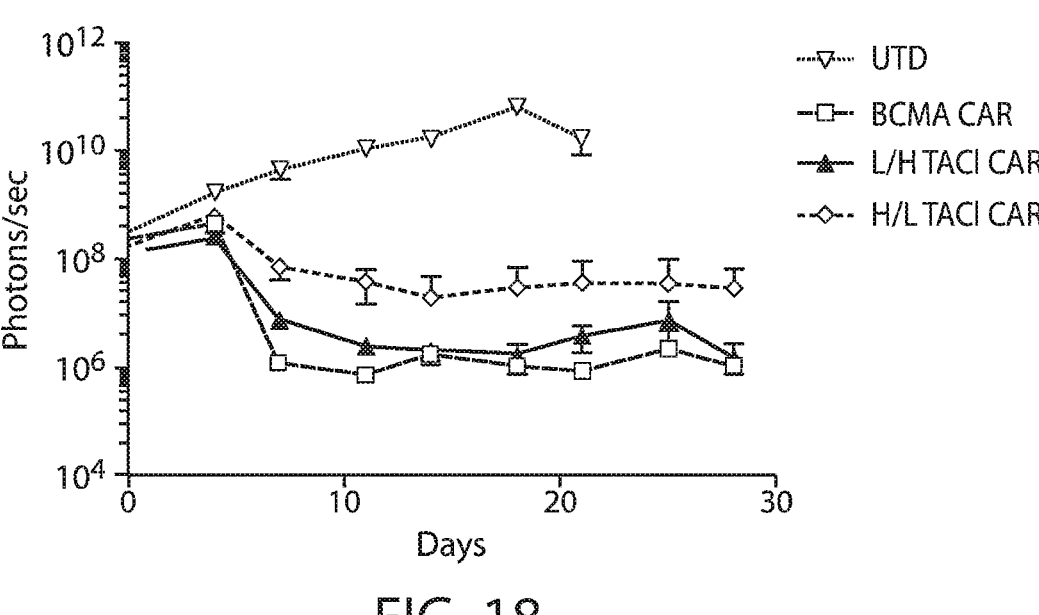
FIG. 18 is a graph showing killing of tumors by UTD, anti-BCMA, anti-TACI (H/L), and anti-TACI (L/H) CAR T cells.
Figure 19:
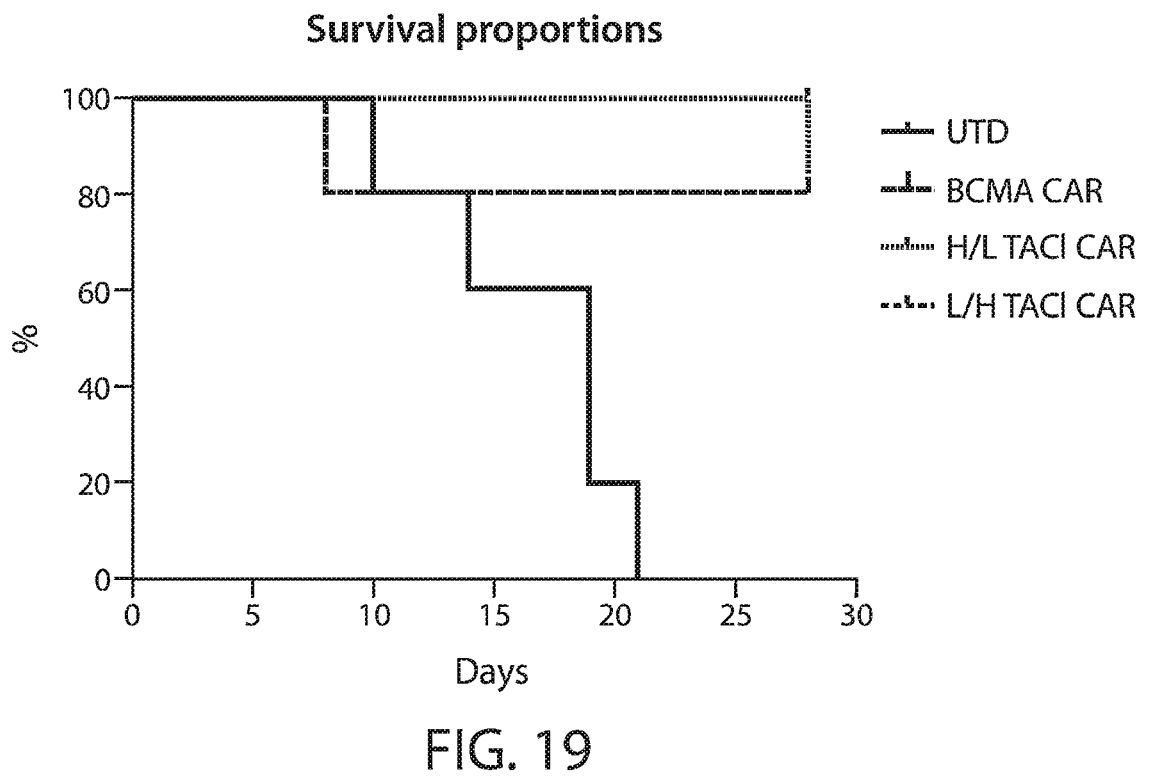

As shown in FIG. 18, anti-TACI (L/H) CAR T cells are as effective as anti-BCMA CAR T cells in treating BCMA+/TACI+ multiple myeloma. FIG. 19 demonstrates the capability of anti-TACI CAR T cells to be curative in TACI+ multiple myeloma.

Figure 26A:
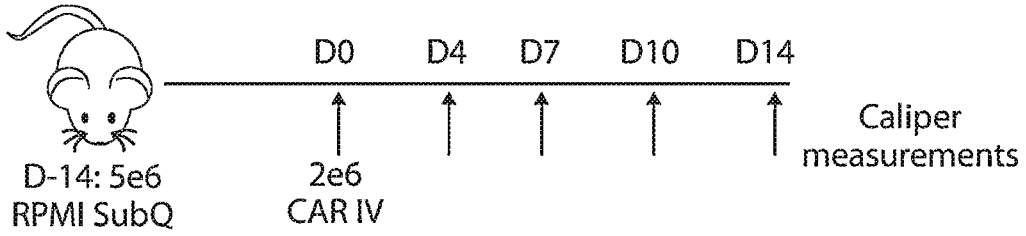
FIGS. 26A-26H show effects of CAR T cells on RPMI8226 sub-cutaneous tumor in mice.
Figure 26B:
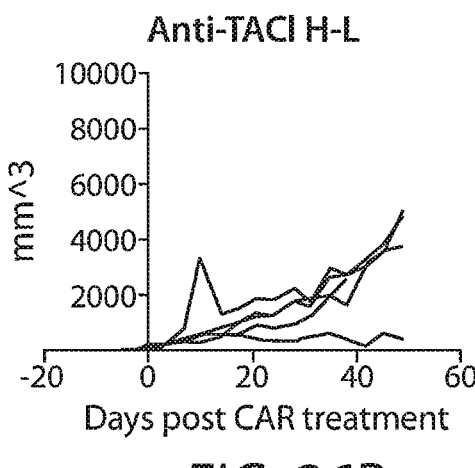
Figure 26C:
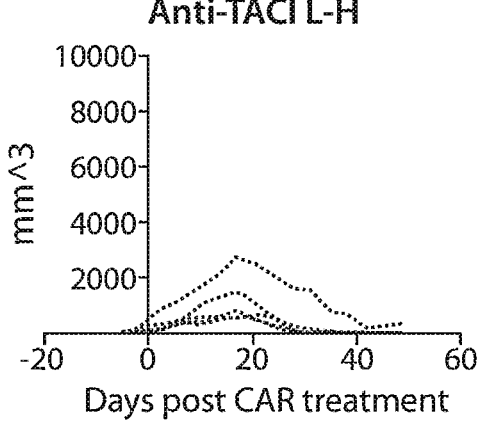
Figure 26D:
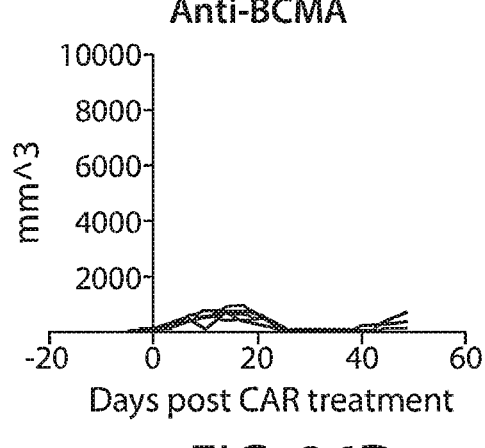
Figure 26E:
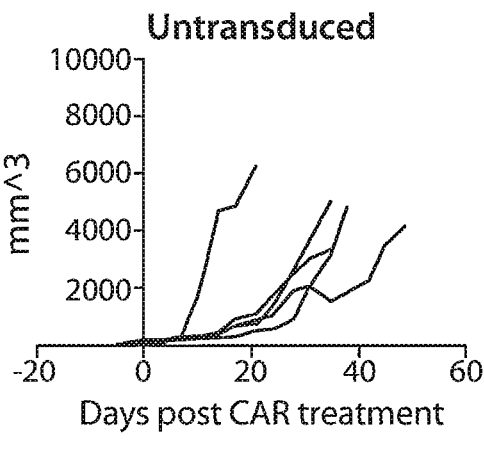
Figure 26F:
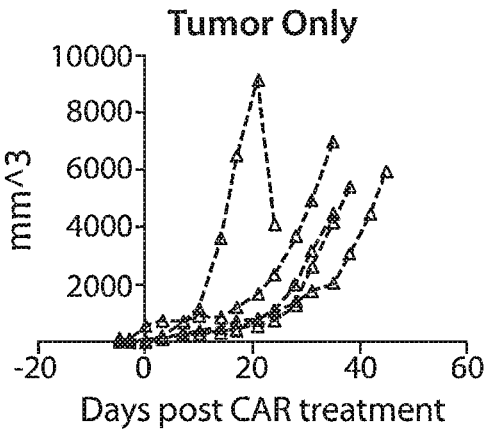
Figure 26G:
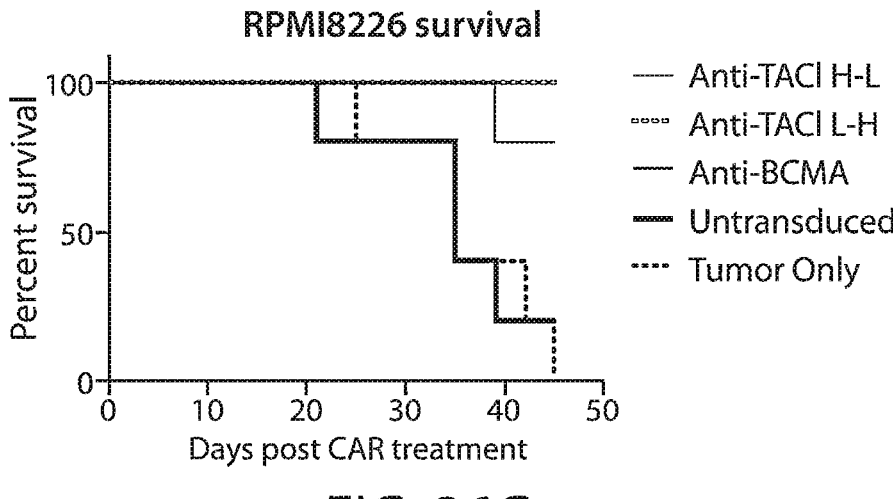
Figure 26H:
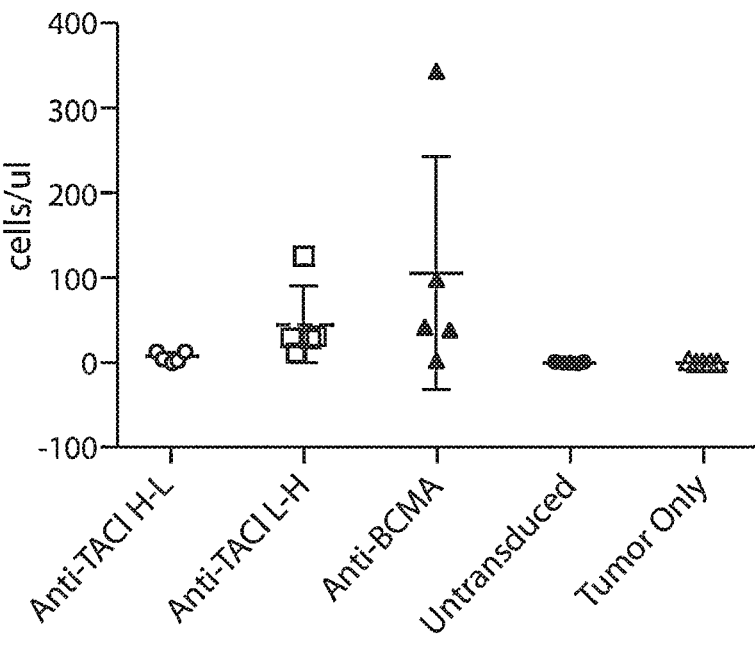

The design of an additional in vivo experiment using the anti-TACI CAR T cells is shown in FIG. 26A. $5 \times 10^6$ RPMI8226 cells were implanted subcutaneously into mice. After 2 weeks, mice were injected intravenously with $2 \times 10^6$ CAR T cells or untransduced cells, or were left untreated. Tumor volumes were measured by calipers 4, 7, 10, and 14 days after CAR T treatment. Individual tumor growth curves are shown in FIGS. 26B, 26C, 26D, 26E, and 26F. FIG. 26G shows survival of mice from each treatment group. Results demonstrate that anti-TACI CAR T cells are efficacious in vivo in a sub-cutaneous tumor growth model at both suppressing tumor growth and extending survival, and suggest that the L-H construct may be more effective than the H-L construct. FIG. 26H further shows that anti-TACI L-H CAR T cells show expansion in the blood at day 21. Anti-BCMA CAR T cells served as a positive control, and untransduced and tumor only groups served as negative controls.

Example 9. Overcoming Antigen Loss in Hematological Malignancies with CAR T Cell Therapy Currently, one of the most promising candidates for CAR T cell therapy beyond CAR19 (CARs targeting CD19) is treatment of multiple myeloma with CAR T cells targeting B cell maturation antigen (BCMA), a member of the TNF receptor superfamily. Multiple myeloma accounts for 13% of all hematological malignancies and has an unmet clinical need for novel treatments. Current reports of BCMA CAR in the clinic have a median progression free survival of 11.8 months, suggesting that targeting BCMA alone may not be sufficient. Similar to what is observed with CAR19 treatment and CD19 negative relapse, evidence suggests patients treated with BCMA-targeted therapies may be thwarted by BCMA negative relapse. In CD19+ malignancies, there have been many approaches to overcoming CD19 negative malignancy including tandem CAR T cells targeting two antigens, such as CD19 and CD20 or CD19 and CD22. In multiple myeloma, a plausible target beyond BCMA is transmembrane activator and CAML interactor (TACI) Like BCMA, TACI is also a member of the TNF receptor superfamily and provides plasma cells with survival signals. This antigen has been targeted with CAR T cells using its natural ligand, A Proliferation-Inducing Ligand (APRIL), which also recognizes BCMA. Currently there is no published CAR T cell that targets TACI alone. To date, there has been no direct comparison of dual-targeting CAR T cells based on scFvs versus a natural ligand design.

Figure 20A:
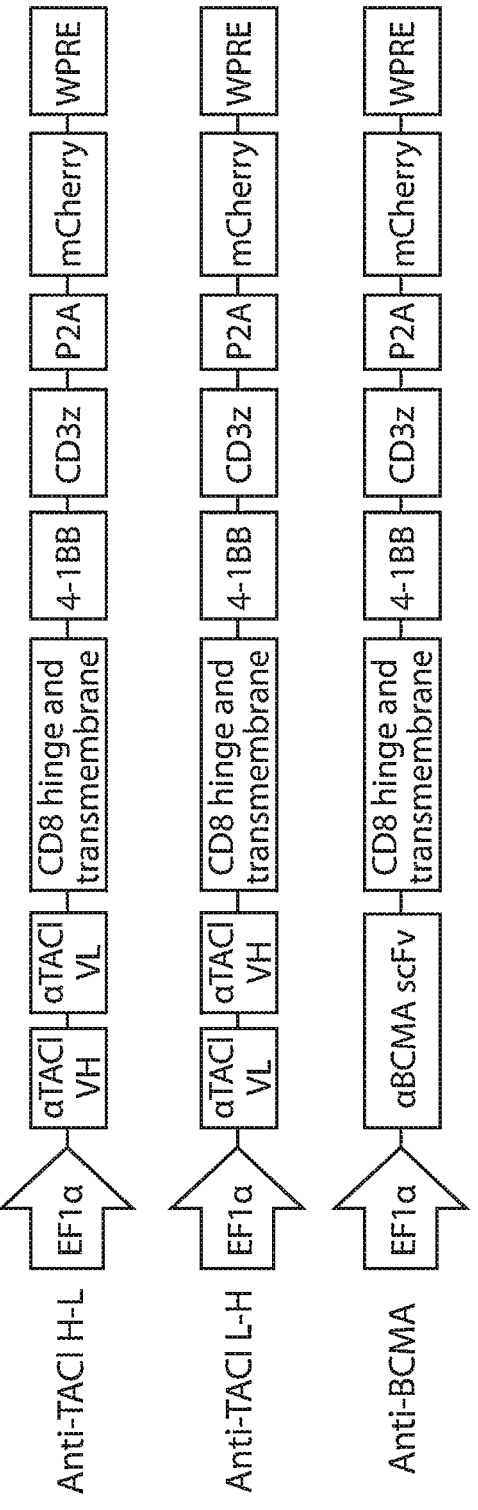
FIGS. 20A-20E show functionality of anti-TACI CAR.
Figure 20B:
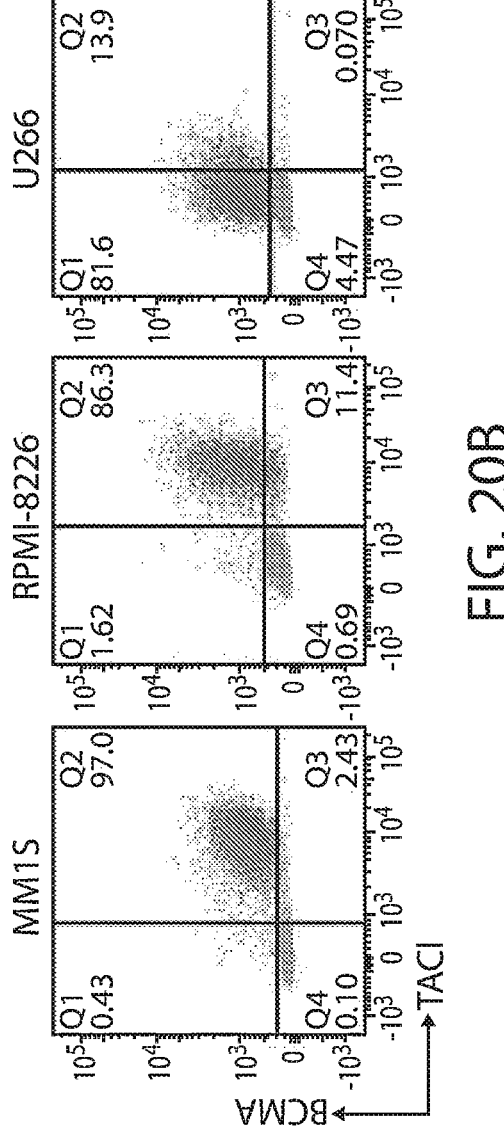
Figure 20C:
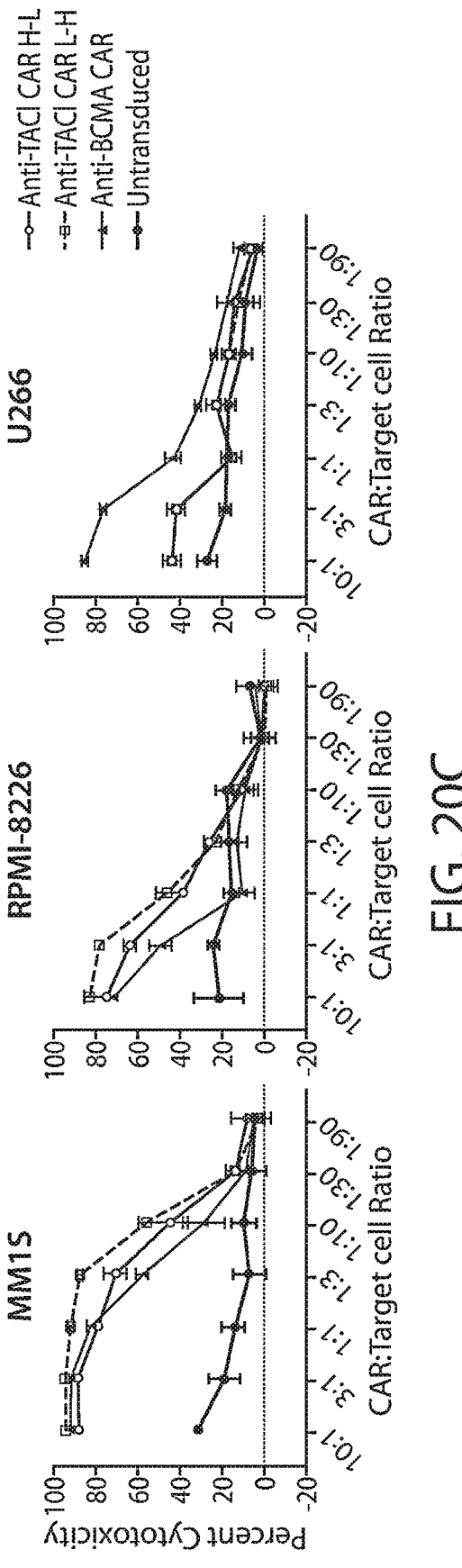
Figure 20D:
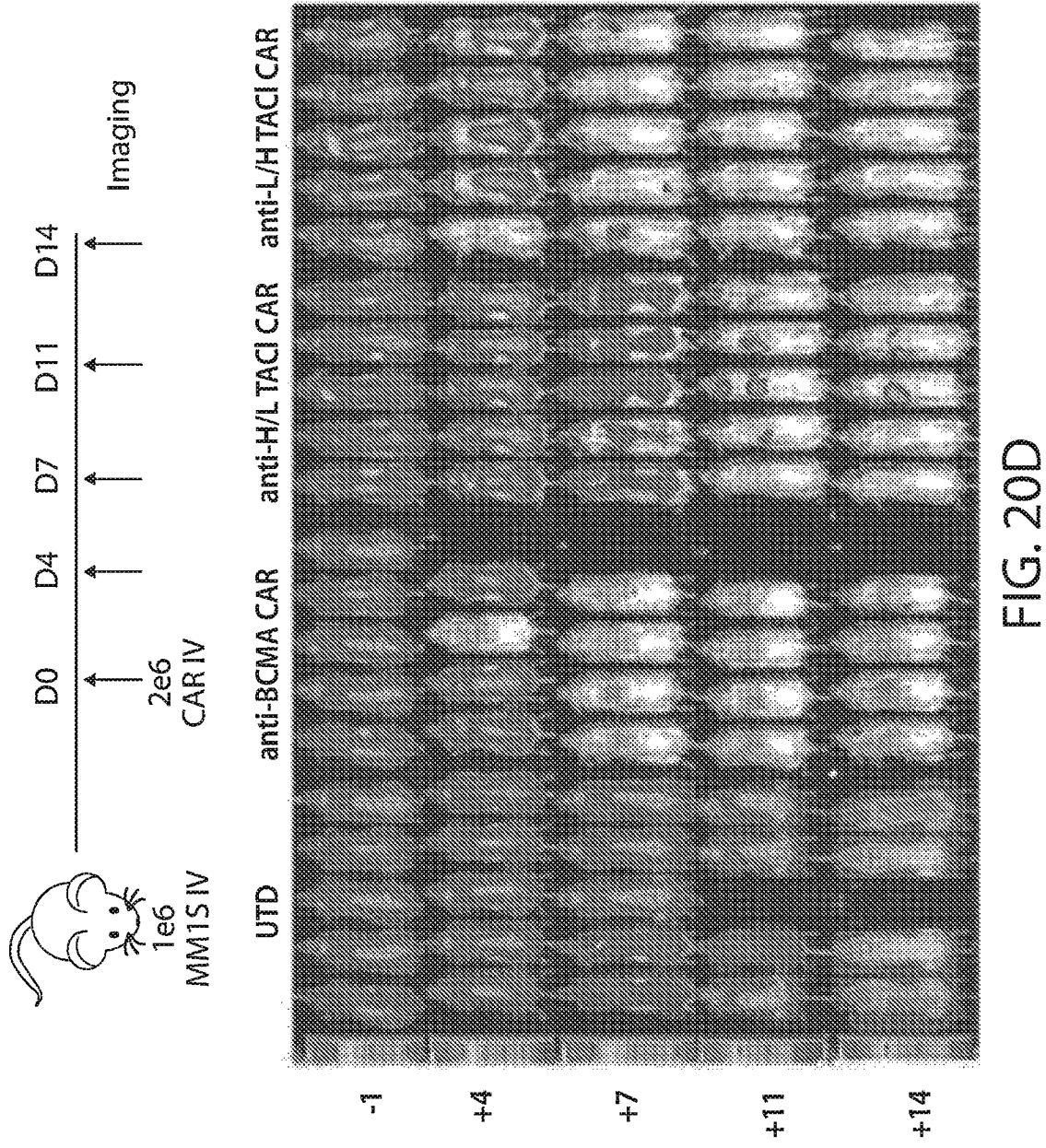
Figure 20E:
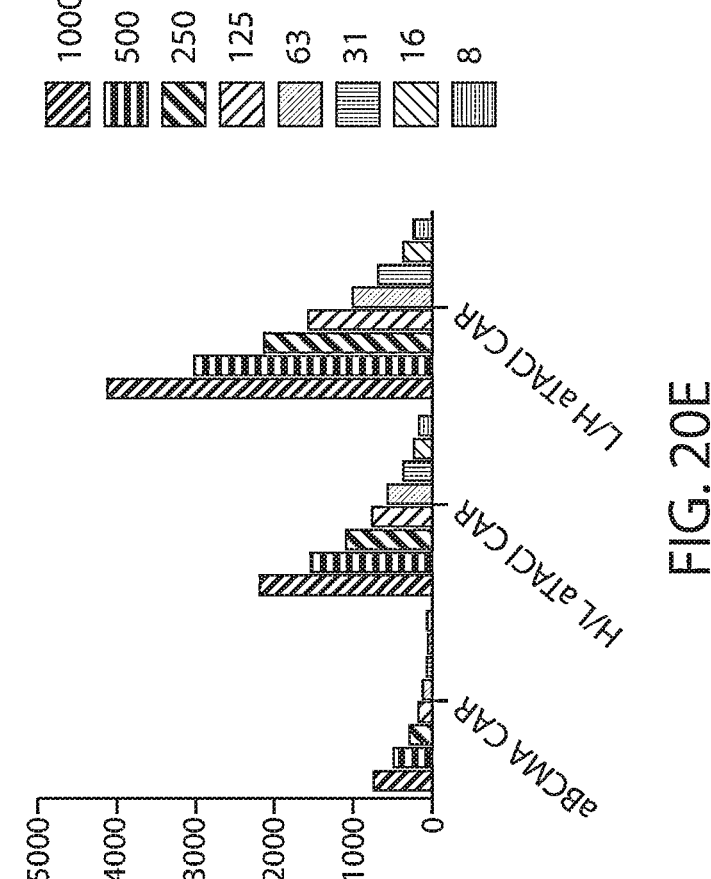

A novel CAR T cell was designed and provide in the present disclosure, targeting TACI by immunizing mice and constructing an anti-TACI CAR from a resulting hybridoma. There were two versions of the anti-TACI CAR based on the orientation of the heavy and light variable chains (FIG. 20A). Anti-TACI CARs are functional in vitro against multiple myeloma lines MM1S and RPM1-8226 which are both BCMA and TACI positive and have much lower activity against TACI low myeloma line U266 (FIGS. 20B-20C). In a transgenic model of multiple myeloma, the L-H orientation of the scFv cured more quickly and in vitro the L-H CAR was more efficient binding soluble TACI (FIGS. 20D-20E).

Figure 21A:
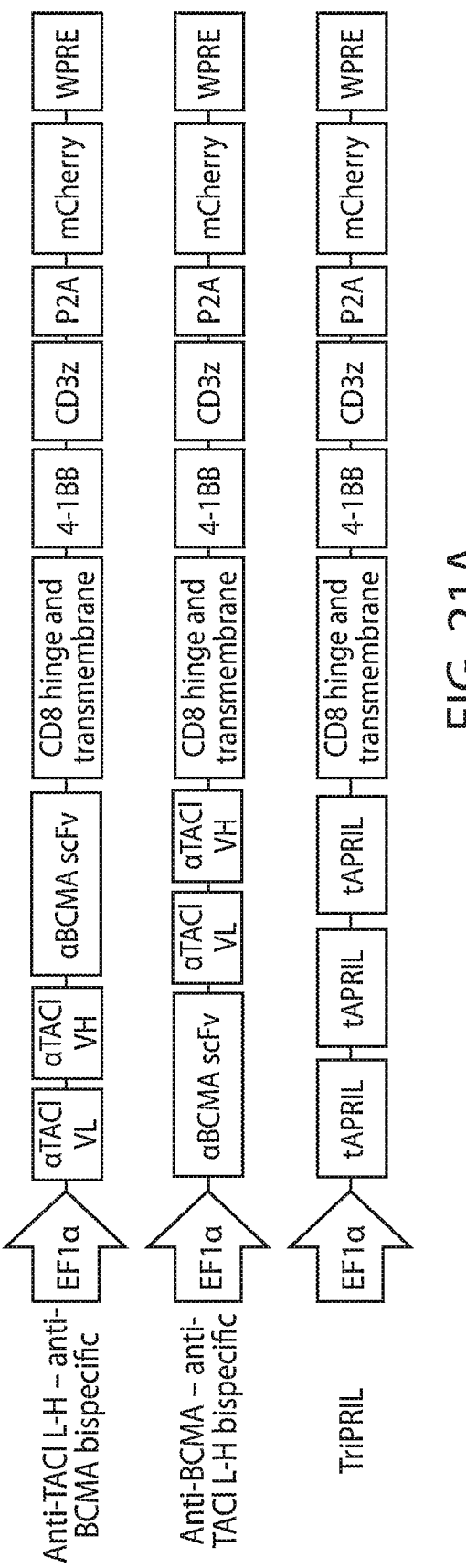
FIGS. 21A-21E show comparison of tandem bispecific BCMA-TACI CARs versus TriPRIL.
Figure 21B:
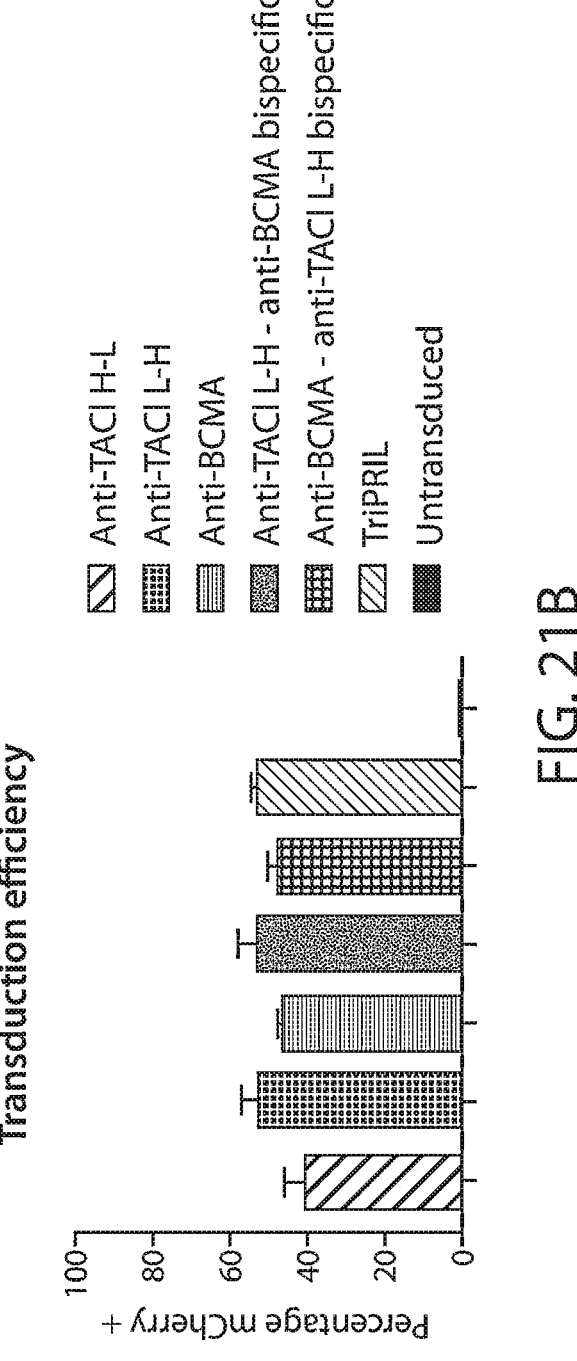
Figure 21C:
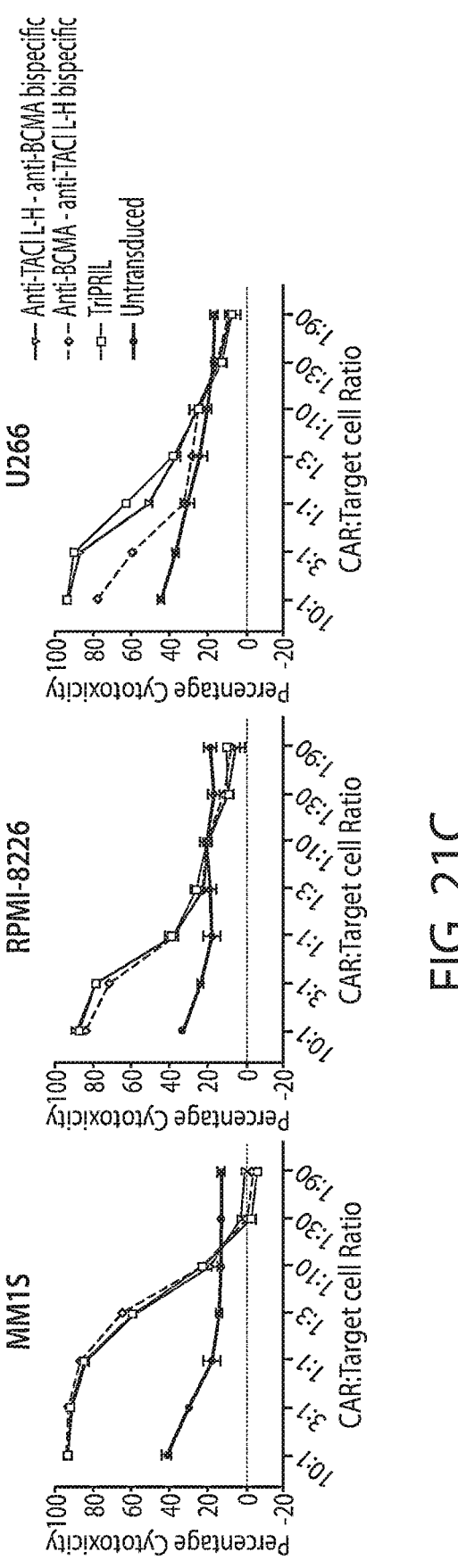
Figure 21D:
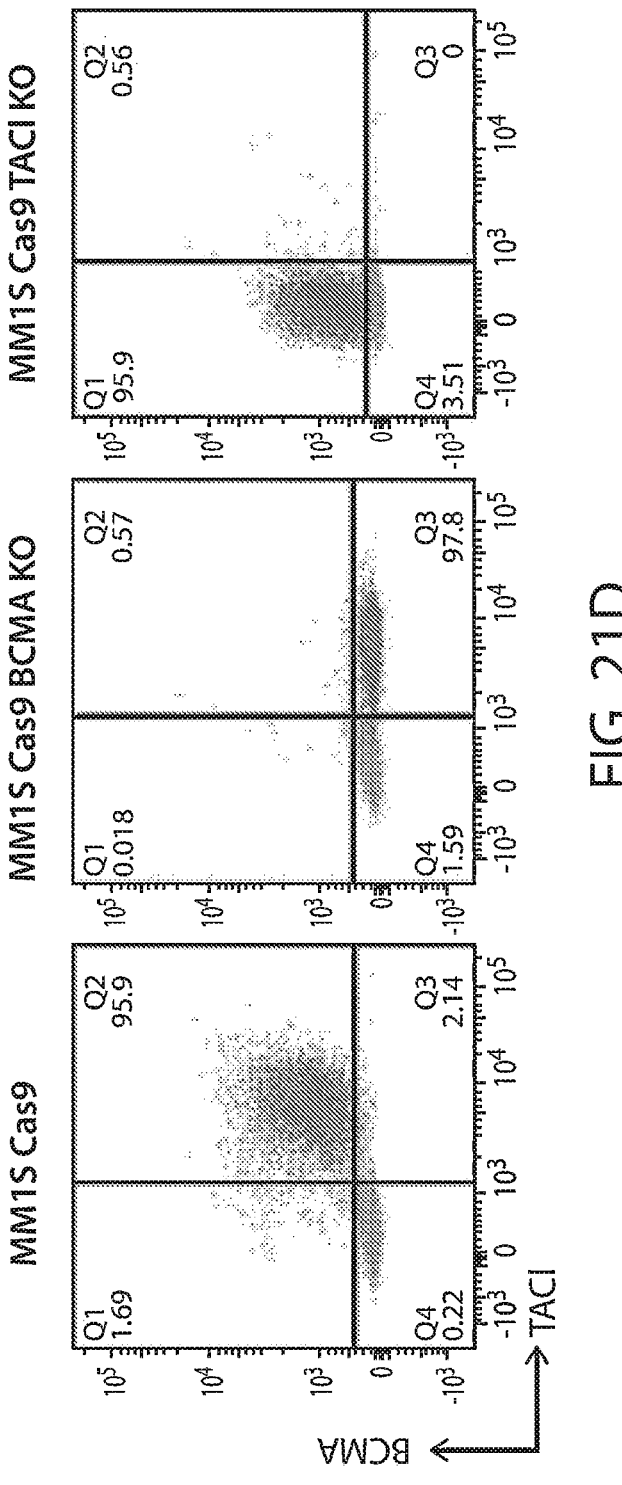
Figure 21E:
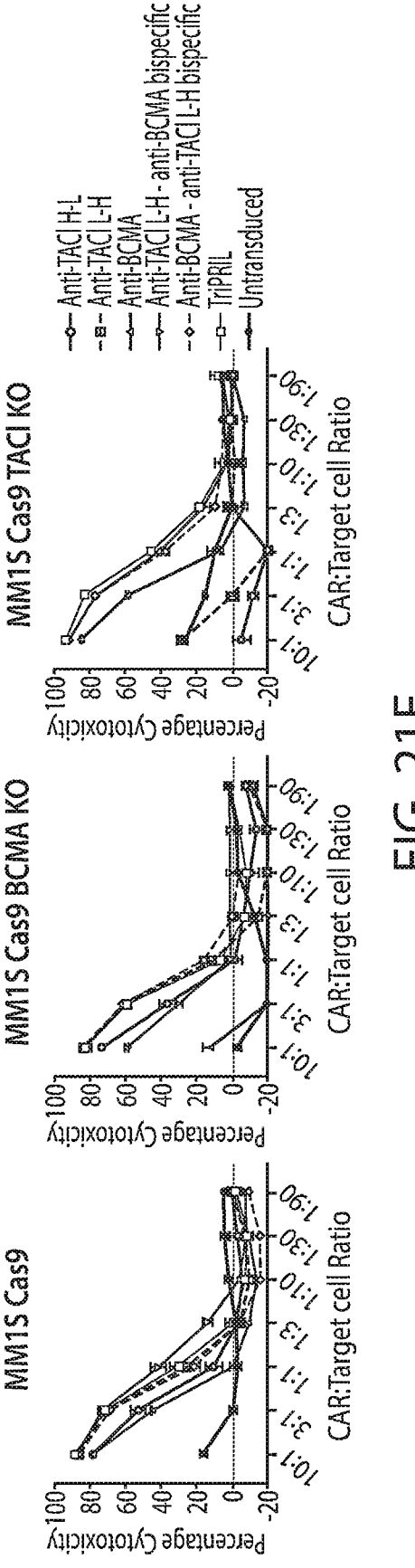
Figure 22A:
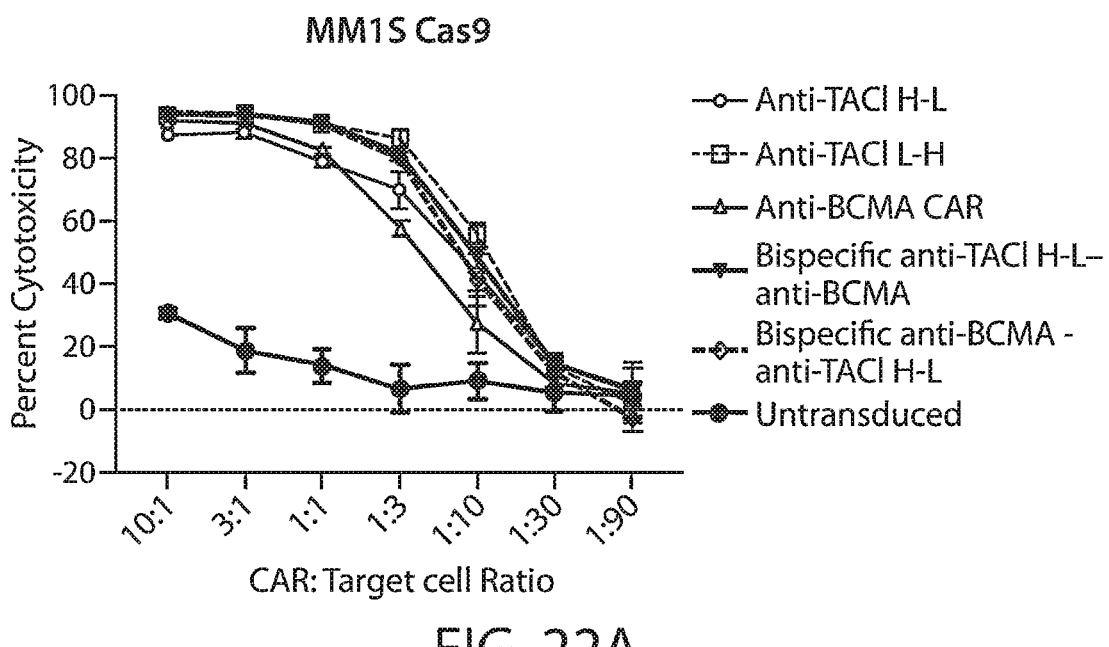
FIGS. 22A-22C show luciferase based killing assays using CAR targeting three different myeloma lines. T cells were incubated with tumor cell lines expressing CBG-GFP for 18 hours then lysed and analyzed for luciferase expression.
Figure 22B:
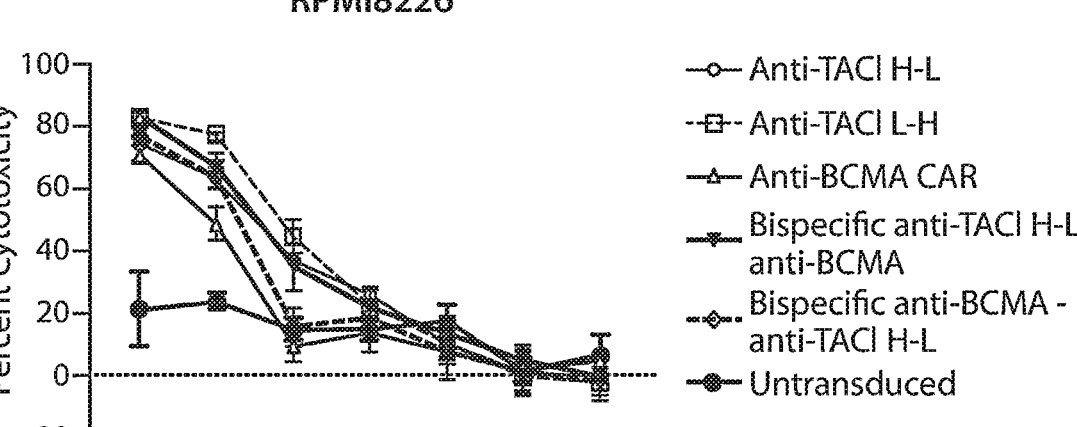
Figure 22C:
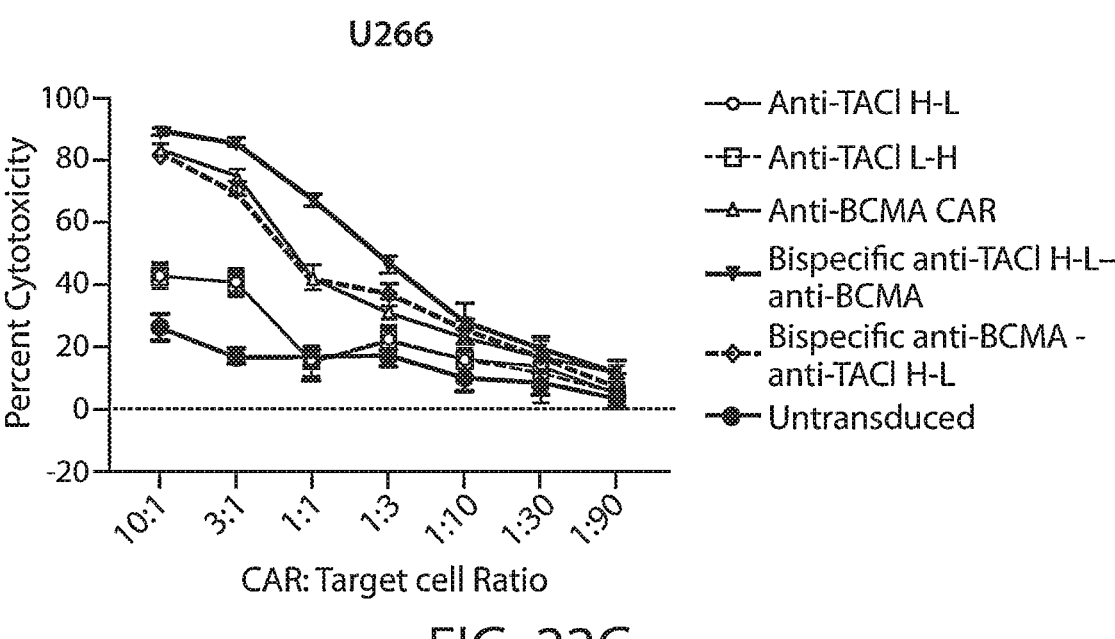

Though anti-TACI CARs are functional in the presence of the TACI antigen, they lose efficacy when antigen is lost, similar to BCMA CAR (FIGS. 21D-21E). To overcome potential loss of antigen which has been a source of failure for CAR19, tandem bispecific CAR T cells were designed, targeting both BCMA and TACI using the anti-TACI scFv (VH-VL configuration). A modified dual-targeting BCMA and TACI CAR were also designed based on their natural ligand APRIL (FIG. 21A). This construct, named TriPRIL, had three repeated truncated APRIL ligands to form a trimer which had been shown to be its secreted form. It was unknown which design of dual-targeting CARs, the tandem bispecific CARs, or the natural ligand, would be a more efficacious therapy. Despite the larger vector size, the transduction efficiency of the dual-targeting CAR constructs was comparable to that of single chain scFvs in normal donor T cells (FIG. 21B). In vitro the cytotoxicity of the dual-targeting tandem bispecific CARs were comparable to TriPRIL against MM1S and RPM1-8226 myeloma lines (FIG. 21C). The anti-TACI-anti-BCMA bispecific and TriPRIL appear to have equal functionality against multiple myeloma line U266 that has low TACI expression (FIG. 20B). The anti-BCMA-anti-TACI bispecific is less efficacious. For loss of antigen scenarios, loss of BCMA shows the greatest difference with the anti-TACI—anti-BCMA bispecific losing some efficacy (FIGS. 21D-21E). Supernatant from these assays was harvested to assess for cytokine production as well.

Example 10. Bispecific CAR T Cells for Multiple Myeloma: Natural Ligand Compared to Tandem scFv Design It was shown in Example 9 that the dual BCMA and TACI targeting CARs, based on tandem scFv or natural ligand design, have similar efficacy against wild type multiple myeloma models. However, this changes in the context of single antigen loss. The proliferative (population doublings) and activation capability (CD69) of these CARs were characterized, as well as their memory (CCR7, CD45RA) and exhaustion phenotype (PD-1, Tim3, LAG-3), with long term exposure to single antigen. It was shown that sensitivity to antigen density differs between the tandem bispecific CARs and the natural ligand CAR. Results indicate that structural differences between dual-targeting CAR T cells affects their function.

Figure 28:
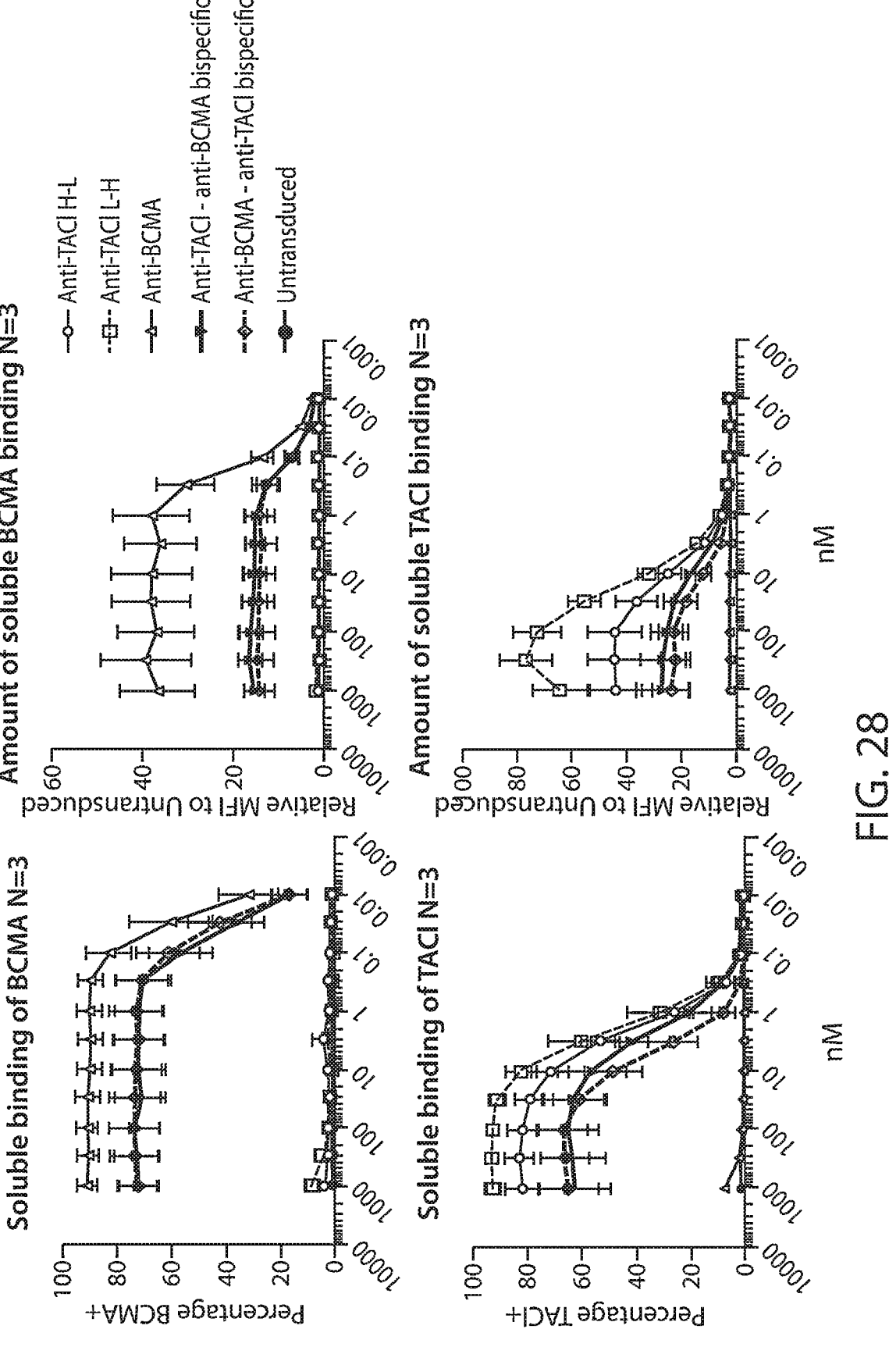
FIG. 28 shows binding affinity of bispecific and singly specific CAR T cells to their respective soluble antigens, measured by flow cytometry. The top two plots show binding of fluorescent BCMA and the bottom two plots show binding of fluorescent TACI to anti-TACI H-L CAR, anti-TACI L-H CAR, anti-BCMA, anti-TACI/anti-BCMA bispecific CAR, anti-BCMA/anti-TACI bispecific CAR, or untransduced T cells. The two left plots show the percentage of cells positive for BCMA or TACI. The two right plots show median fluorescence intensity for each cell population relative to untransduced cells.

To test the efficacy of bispecific CAR T cells to bind their respective antigens, T cells were either left untransduced, or transduced with anti-TACI H-L CAR, anti-TACI L-H CAR, anti-BCMA CAR, anti-TACI/anti-BCMA bispecific CAR, or anti-BCMA/anti-TACI bispecific CAR, and were tested for their binding of soluble antigens. Results demonstrate that bispecific CARs have lower binding affinity for their soluble antigens compared with their singly specific counterparts, and that orientation of the two components of the bispecific CARs tested do not affect their binding (FIG. 28).

Figure 29:
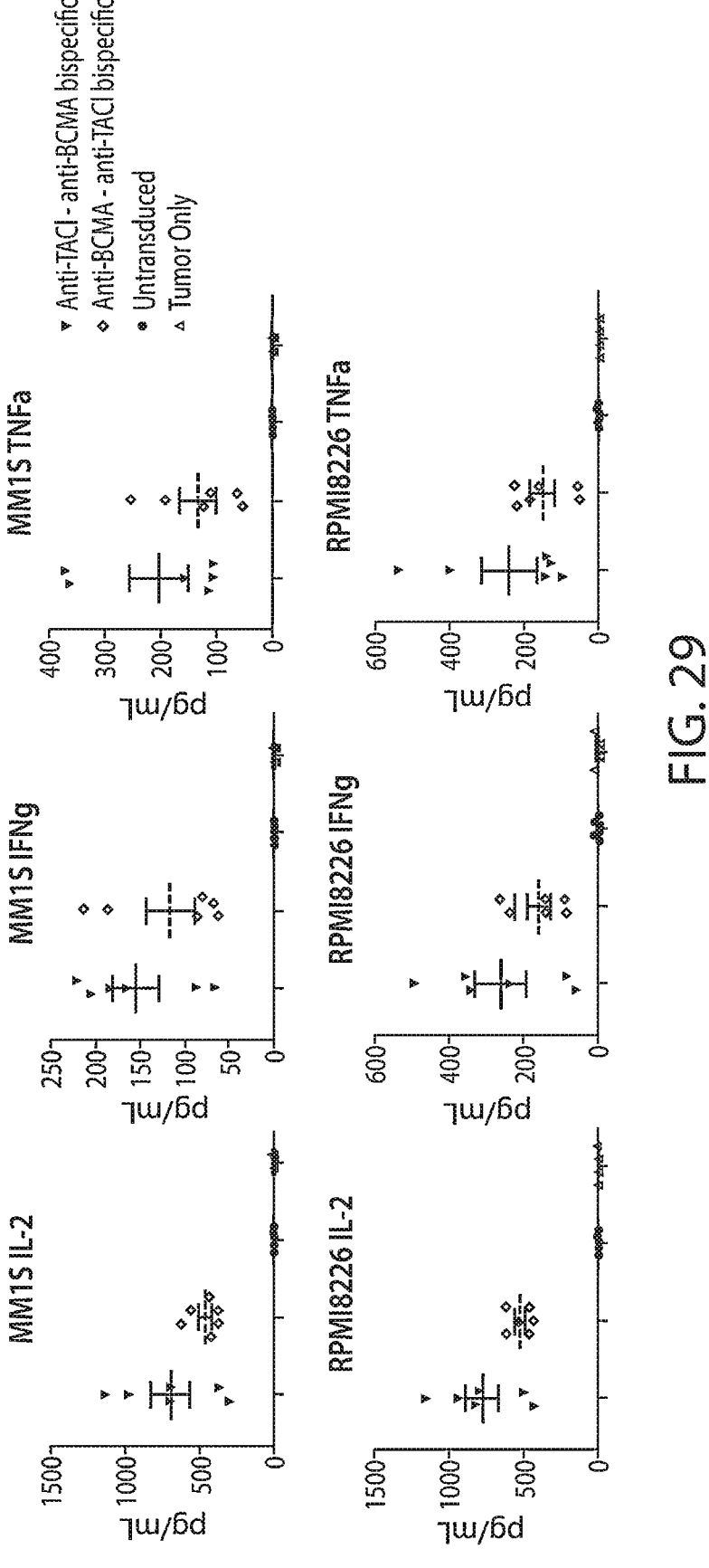
FIG. 29 shows measurements of cytokine concentrations in supernatant from cultures of MM1S (top plots) or RPMI8226 (bottom plots) cancer cells either alone or in co-culture with anti-TACI/anti-BCMA bispecific CAR, anti-BCMA/anti-TACI bispecific CAR, or untransduced T cells. The left plots show interleukin-2 (IL-2) concentrations, the middle plots show interferon-gamma (IFNg) concentrations, and the right plots show tumor necrosis factor alpha (TNFa) concentrations.

To test the effect of bispecific CARs on cytokine production in cancer cell/T cell co-cultures, MM1S or RPMI8226 multiple myeloma cells were cultured alone or in co-culture with untransduced T cells, T cells transduced with anti-TACI/anti-BCMA bispecific CAR, or T cells transduced with anti-BCMA/anti-TACI bispecific CAR, and cytokines were measured in culture supernatants. Results demonstrate that bispecific CAR T cells produce interleukin-2 (IL-2), interferon-gamma (IFN-γ), and tumor necrosis factor alpha (TNF-α) in response to multiple myeloma cell lines in vitro (FIG. 29).

Figure 30A:
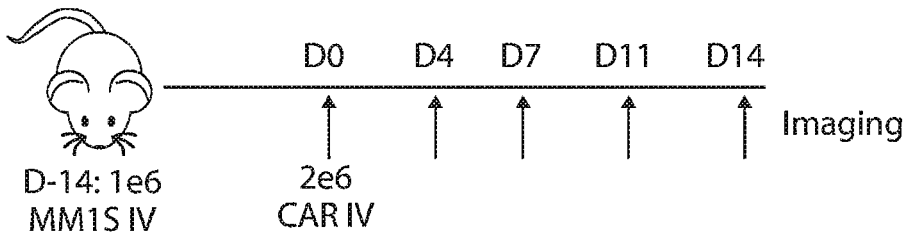
FIGS. 30A-30E show results from an MM1S stress model with bispecific CAR T cells.
Figure 30B:
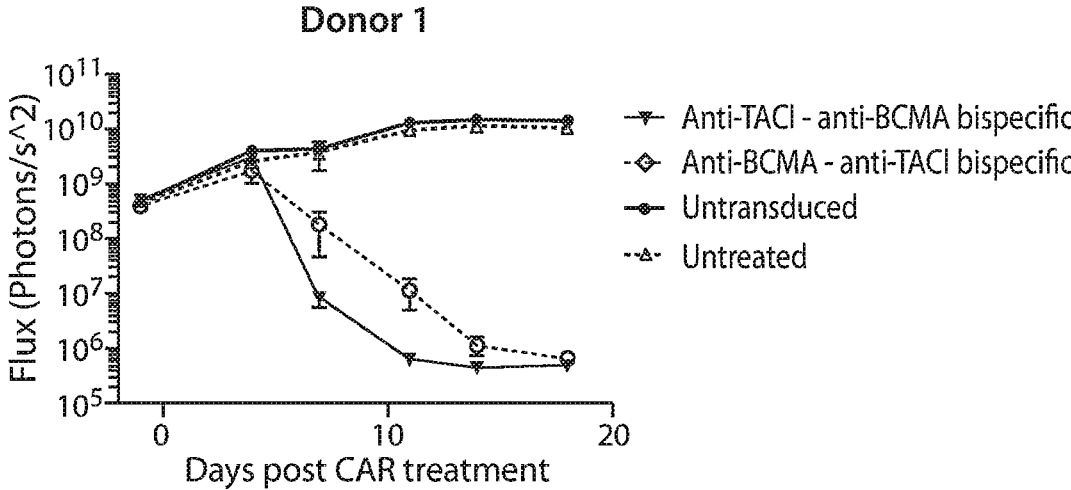
Figure 30C:
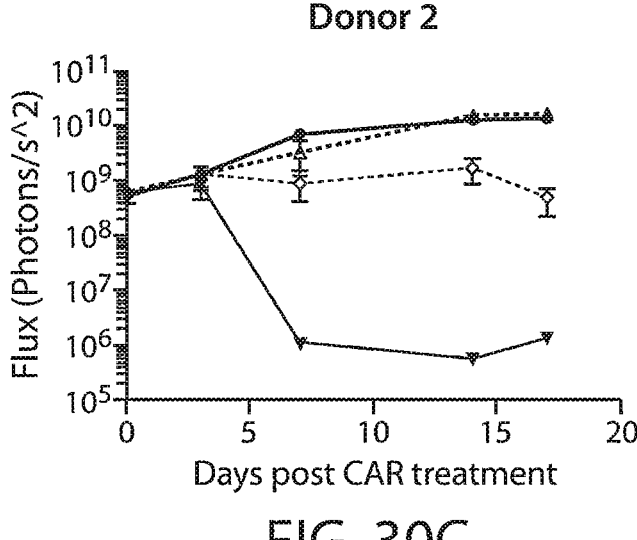
Figures 30D, 30E:
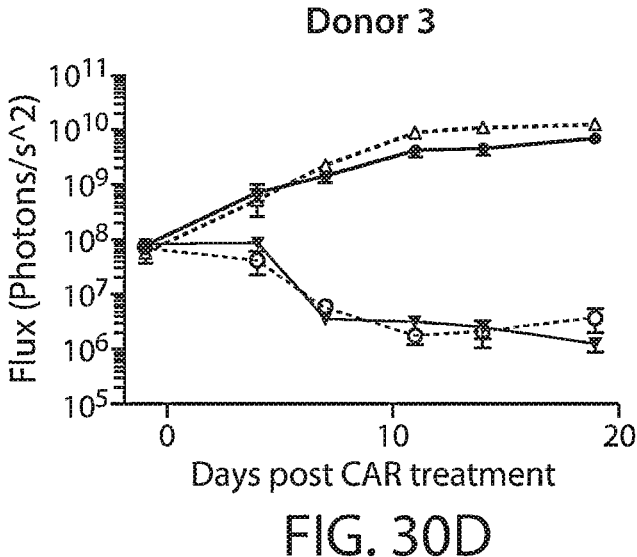

The design of an additional experiment using bispecific CAR T cells in vivo is shown in FIG. 30A. First, $1 \times 10^6$ MM1S multiple myeloma cells were injected intravenously (i.v.) into mice. Then, 2 weeks later, $2 \times 10^6$ CAR T cells were injected and bioluminescence imaging was conducted to detect MM1S cell viability over time. Bioluminescence flux measurements over time in mice that were untreated or treated with untransduced T cells, or T cells transduced with anti-TACI/anti-BCMA bispecific CAR or anti-BCMA/anti-TACI bispecific CAR are shown in FIGS. 30B, 30C, and 30D for T cells from three different donors. Representative bioluminescence images from donor 1 are shown in FIG. 30E. Results demonstrate that bispecific CAR T cells are functional against MM1S in vivo, and that anti-BCMA/anti-TACI CAR T cells from 2 of 3 donors were efficacious and anti-TACI/anti-BCMA CAR T cells from 3 of 3 donors were efficacious.

Figure 31A:
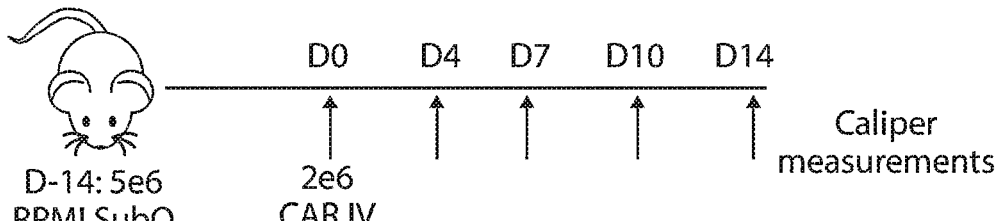
FIGS. 31A-31F show results from a RPMI8226 sub-cutaneous tumor model.
Figure 31B:
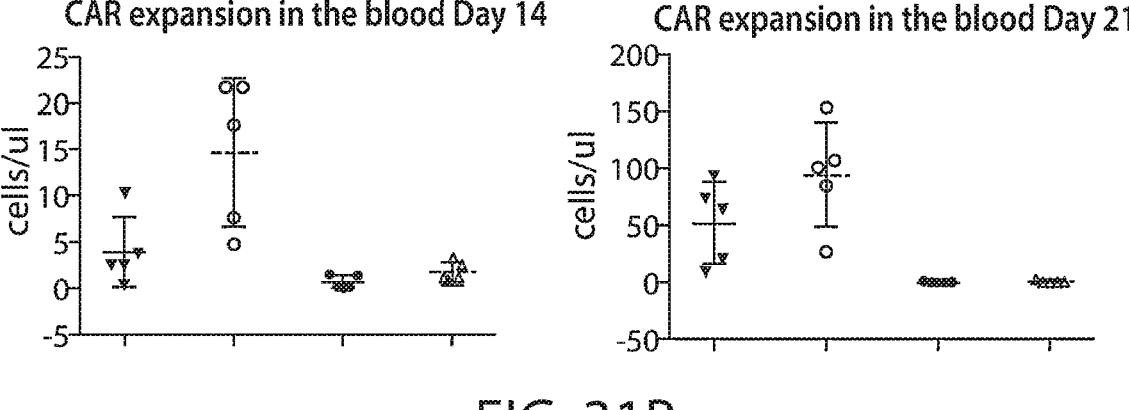
Figure 31C:
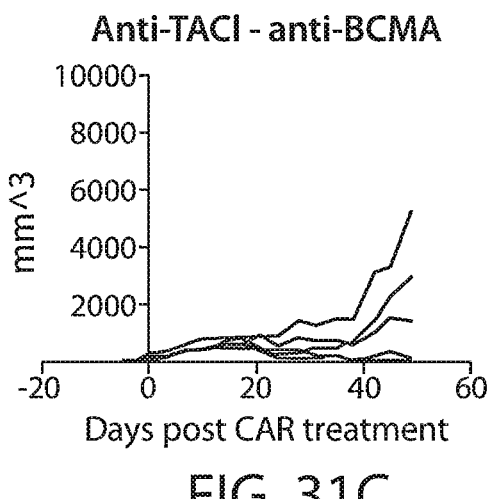
Figure 31D:
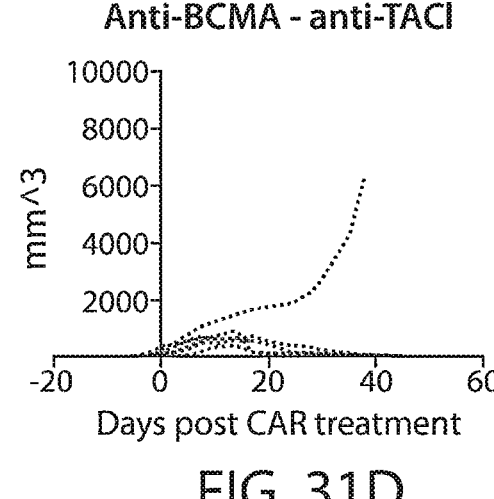
Figure 31E:
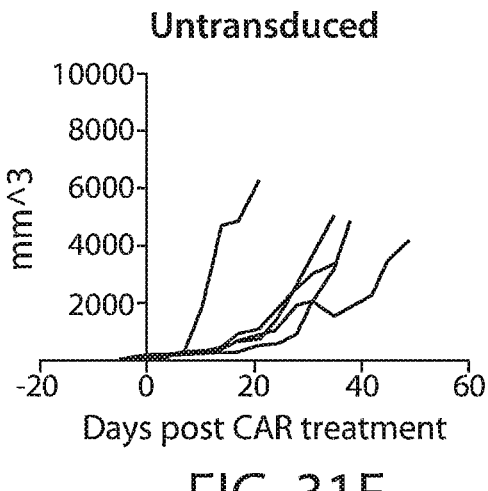
Figure 31F:
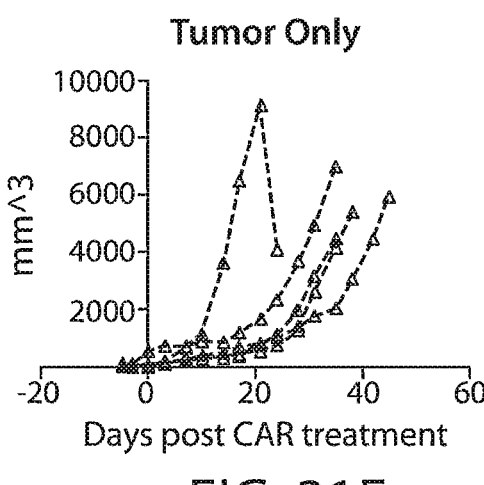
Figure 32A:
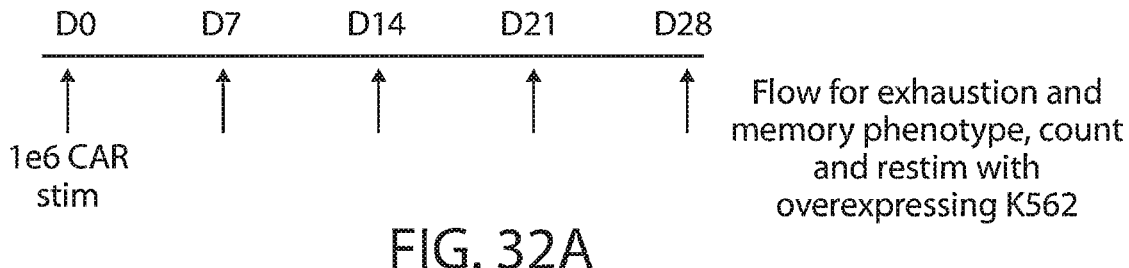
FIGS. 32A-32B show results of an experiment to monitor T cell exhaustion after repeated antigen stimulation.
Figure 32B:
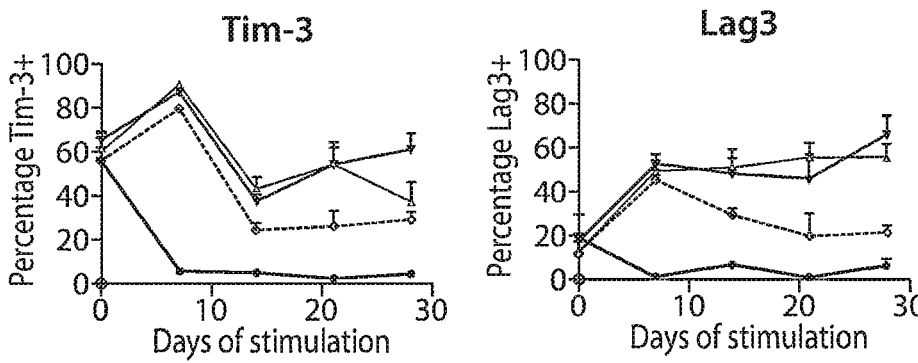

Bispecific CAR T cells showed further efficacy in a sub-cutaneous tumor model of multiple myeloma. FIG. 31A shows the experimental design, in which $5 \times 10^6$ RPMI8226 cells were implanted subcutaneously in mice, which were then injected intravenously with CAR T cells 2 weeks later. Tumor volumes were measured over time, and CAR T cells were counted in blood on days 14 and 21 post injection. Results demonstrate that anti-BCMA/anti-TACI CAR T cells expand more in vivo than anti-TACI/anti-BCMA CAR T cells or untransduced T cells (FIG. 31B), and both CAR T cell types suppress sub-cutaneous tumor growth relative to untransduced T cells or tumors in untreated mice (FIGS. 31C, 31D, 31E, and 31F).T cell exhaustion can contribute to ineffectiveness of CAR T cells. To evaluate exhaustion of bispecific CAR T cells, an experiment was conducted according to the timeline shown in FIG. 32A. First, $1 \times 10^6$ T cells, either untransduced or transduced with anti-BCMA CAR, anti-TACI/anti-BCMA bispecific CAR, or anti- BCMA/anti-TACI bispecific CAR construct were plated. At days 0, 7, 14, 21, and 28 after initial plating flow cytometric analysis of Tim-3 and Lag3 exhaustion markers was conducted. At each time point, the T cells were counted, plated at $1\times10^6$ cells per condition, and (re)stimulated with irradiated K562 cells overexpressing BCMA. Results demonstrate that anti-BCMA/anti-TACI bispecific CAR T cells show lower expression of exhaustion markers Tim-3 and Lag3 with repeated stimulation compared to anti-BCMA and anti-TACI/anti-BCMA bispecific CAR T cells, which may account for their greater efficacy against single antigens.

Figure 33A:
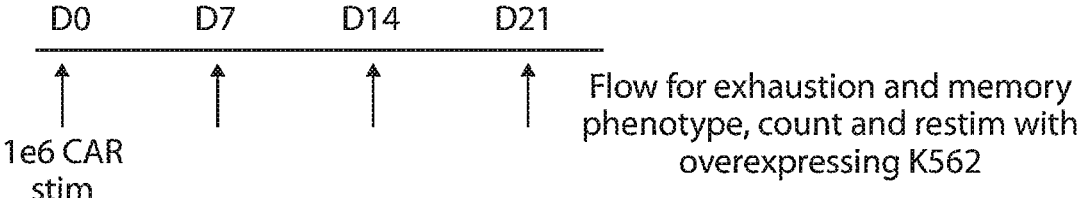
FIGS. 33A-33C show results of analysis of T cell phenotypes in repeatedly stimulated CAR T cells.
Figure 33B:
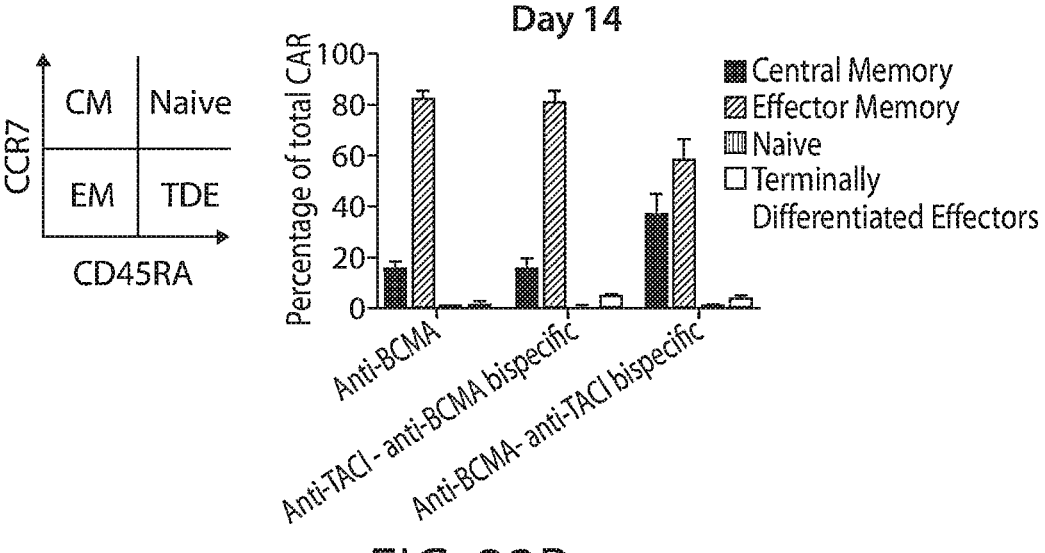
Figure 33C:
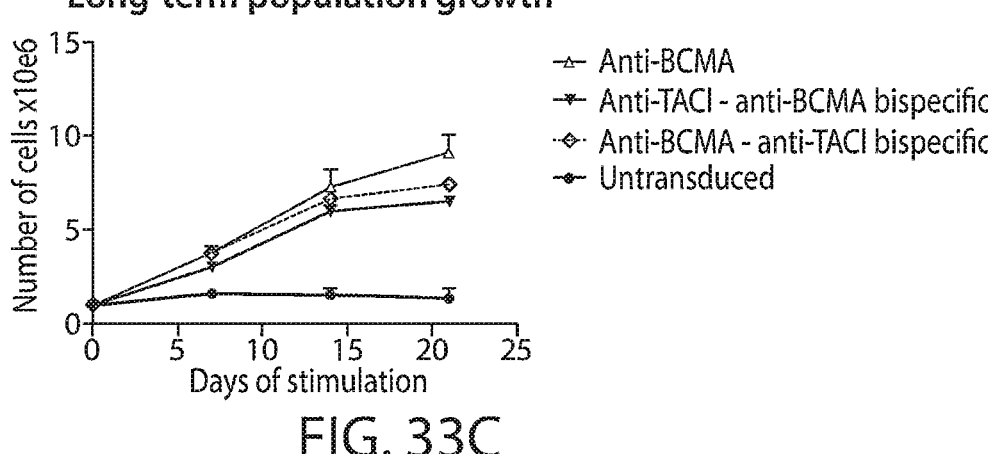

T cell phenotypes within CAR T cell populations were evaluated according to the experimental design summarized in FIG. 33A. CAR T cells expressing anti-BCMA CAR, anti-TACI/anti-BCMA bispecific CAR, or anti-BCMA/anti-TACI bispecific CAR were counted and $1\times10^6$ cells were plated, and memory phenotype was quantified by flow cytometry every week. CAR T cells were characterized according to the four phenotypes shown in the left side of FIG. 33B. Cells were categorized as central memory (CM) if they were positive for CCR7 and negative for CD45RA; as effector memory (EM) if they were negative for both CCR7 and CD45RA; as terminally differentiated effector (TDE) if they were negative for CCR7 and positive for CD45RA; or as naïve if they were positive for both CCR7 and CD45RA. See X. Wang, et al., *Blood* (2016) 127(24): 2980-2990; L. Gattinoni, et al., *Nat. Med.* (2011) 17(10): 1290-1297; and L. Biasco, et al., *Sci. Transl. Med.* (2015) 7(273):273ra213. Results demonstrated that larger proportions of anti-BCMA/anti-TACI bispecific CAR T cells retain central memory phenotype than anti-TACI/anti-BCMA bispecific CAR T cells or anti-BCMA CAR T cells, which instead convert to an effector phenotype in the same timeframe (FIG. 33B). Little difference in expansion between the groups was observed (FIG. 33C).

TABLE 2

Amino Acid Sequences

| SEQ ID NO: | Description | Sequence |
|---|---|---|
| 1 | VH | EVQLQQSGPELVKPGASVKISCKTSGYTFTESTIHWVKQ SHGKSLEWIGGISPNNGGSPFNQKFKGKATLTVDKSSST VYMELRSLSSEDSAVYYCAKWVRGAMDFWGQGTSVT VSS |
| 2 | VL | DIVLTQSPASLAVSLGQRATISCRASESVDYYGMSLMN WFQQKPGQPPKLVIYAASNQGSGVPARFSGSGSGTDFR LNIHPLEEDDTGMYFCQQSKEAPPTFGGGTKLEIK |
| 3 | (G$_4$S)$_4$ linker | GGGGSGGGGSGGGGSGGGGS |
| 4 | Anti-TACI scFv (H-L) | EVQLQQSGPELVKPGASVKISCKTSGYTFTESTIHWVKQ SHGKSLEWIGGISPNNGGSPFNQKFKGKATLTVDKSSST VYMELRSLSSEDSAVYYCAKWVRGAMDFWGQGTSVT VSSGGGGSGGGGSGGGGSGGGGSDIVLTQSPASLAVSL GQRATISCRASESVDYYGMSLMNWFQQKPGQPPKLVI YAASNQGSGVPARFSGSGSGTDFRLNIHPLEEDDTGMY FCQQSKEAPPTFGGGTKLEIK |
| 5 | Anti-TACI scFv (L-H) | DIVLTQSPASLAVSLGQRATISCRASESVDYYGMSLMN WFQQKPGQPPKLVIYAASNQGSGVPARFSGSGSGTDFR LNIHPLEEDDTGMYFCQQSKEAPPTFGGGTKLEIKGGG GSGGGGSGGGGSGGGGSEVQLQQSGPELVKPGASVKIS CKTSGYTFTESTIHWVKQSHGKSLEWIGGISPNNGGSPF NQKFKGKATLTVDKSSSTVYMELRSLSSEDSAVYYCA KWVRGAMDFWGQGTSVTVSS |
| 6 | CD8 signal sequence | MALPVTALLLPLALLLHAARP |
| 7 | CD8 hinge/ transmembrane domain | TTTPAPRPPTPAPTIASQPLSLRPEACRPAAGGAVHTRGL DFACDIYIWAPLAGTCGVLLLSLVITLYC |
| 8 | 4-1BB co-stimulatory domain | KRGRKKLLYIFKQPFMRPVQTTQEEDGCSCRFPEEEEG GCEL |
| 9 | CD3ζ intracellular signaling domain | RVKFSRSADAPAYQQGQNQLYNELNLGRREEYDVLDK RRGRDPEMGGKPRRKNPQEGLYNELQKDKMAEAYSEI GMKGERRRGKGHDGLYQGLSTATKDTYDALHMQALP PR |
| 10 | Anti-TACI CAR (H-L) | EVQLQQSGPELVKPGASVKISCKTSGYTFTESTIHWVKQ SHGKSLEWIGGISPNNGGSPFNQKFKGKATLTVDKSSST VYMELRSLSSEDSAVYYCAKWVRGAMDFWGQGTSVT VSSGGGGSGGGGSGGGGSGGGGSDIVLTQSPASLAVSL GQRATISCRASESVDYYGMSLMNWFQQKPGQPPKLVI YAASNQGSGVPARFSGSGSGTDFRLNIHPLEEDDTGMY FCQQSKEAPPTFGGGTKLEIKTTTPAPRPPTPAPTIASQP LSLRPEACRPAAGGAVHTRGLDFACDIYIWAPLAGTCG VLLLSLVITLYCKRGRKKLLYIFKQPFMRPVQTTQEEDG CSCRFPEEEEGGCELRVKFSRSADAPAYQQGQNQLYNE |

TABLE 2-continued

| Amino Acid Sequences | | |
|---|---|---|

| SEQ ID NO: | Description | Sequence |
|---|---|---|
| | | LNLGRREEYDVLDKRRGRDPEMGGKPRRKNPQEGLYN ELQKDKMAEAYSEIGMKGERRRGKGHDGLYQGLSTAT KDTYDALHMQALPPR |
| 11 | Anti-TACI CAR (L-H) | DIVLTQSPASLAVSLGQRATISCRASESVDYYGMSLMN WFQQKPGQPPKLVIYAASNQGSGVPARFSGSGSGTDFR LNIHPLEEDDTGMYFCQQSKEAPPTFGGGTKLEIKGGG GSGGGGSGGGGSGGGGSEVQLQQSGPELVKPGASVKIS CKTSGYTFTESTIHWVKQSHGKSLEWIGGISPNNGGSPF NQKFKGKATLTVDKSSSTVYMELRSLSSEDSAVYYCA KWVRGAMDFWGQGTSVTVSSTTTPAPRPPTPAPTIASQ PLSLRPEACRPAAGGAVHTRGLDFACDIYIWAPLAGTC GVLLLSLVITLYCKRGRKKLLYIFKQPFMRPVQTTQEED GCSCRFPEEEEGGCELRVKFSRSADAPAYQQGQNQLYN ELNLGRREEYDVLDKRRGRDPEMGGKPRRKNPQEGLY NELQKDKMAEAYSEIGMKGERRRGKGHDGLYQGLST ATKDTYDALHMQALPPR |
| 12 | Anti-TACI CAR (H-L) + CD8 signal sequence | MALPVTALLLPLALLLHAARPEVQLQQSGPELVKPGAS VKISCKTSGYTFTESTIHWVKQSHGKSLEWIGGISPNNG GSPFNQKFKGKATLTVDKSSSTVYMELRSLSSEDSAVY YCAKWVRGAMDFWGQGTSVTVSSGGGGSGGGGSGG GGSGGGGSDIVLTQSPASLAVSLGQRATISCRASESVDY YGMSLMNWFQQKPGQPPKLVIYAASNQGSGVPARFSG SGSGTDFRLNIHPLEEDDTGMYFCQQSKEAPPTFGGGT KLEIKTTTPAPRPPTPAPTIASQPLSLRPEACRPAAGGAV HTRGLDFACDIYIWAPLAGTCGVLLLSLVITLYCKRGR KKLLYIFKQPFMRPVQTTQEEDGCSCRFPEEEEGGCELR VKFSRSADAPAYQQGQNQLYNELNLGRREEYDVLDKR RGRDPEMGGKPRRKNPQEGLYNELQKDKMAEAYSEIG MKGERRRGKGHDGLYQGLSTATKDTYDALHMQALPP R |
| 13 | Anti-TACI CAR (L-H) + CD8 signal sequence | MALPVTALLLPLALLLHAARPDIVLTQSPASLAVSLGQR ATISCRASESVDYYGMSLMNWFQQKPGQPPKLVIYAAS NQGSGVPARFSGSGSGTDFRLNIHPLEEDDTGMYFCQQ SKEAPPTFGGGTKLEIKGGGGSGGGGSGGGGSGGGGSE VQLQQSGPELVKPGASVKISCKTSGYTFTESTIHWVKQS HGKSLEWIGGISPNNGGSPFNQKFKGKATLTVDKSSST VYMELRSLSSEDSAVYYCAKWVRGAMDFWGQGTSVT VSSTTTPAPRPPTPAPTIASQPLSLRPEACRPAAGGAVHT RGLDFACDIYIWAPLAGTCGVLLLSLVITLYCKRGRKK LLYIFKQPFMRPVQTTQEEDGCSCRFPEEEEGGCELRVK FSRSADAPAYQQGQNQLYNELNLGRREEYDVLDKRRG RDPEMGGKPRRKNPQEGLYNELQKDKMAEAYSEIGM KGERRRGKGHDGLYQGLSTATKDTYDALHMQALPPR |
| 14 | (G₃S)₃ linker | GGGSGGGSGGGS |
| 15 | (G₄S)₃ linker | GGGGSGGGGSGGGGS |
| 16 | Whitlow linker | GSTSGSGKPGSGEGSTKG |
| 17 | Andris-Widhopf linker | GGSSRSSSSGGGGSGGGG |
| 18 | CD8 Leader - anti-TACI H-L - linker - anti-BCMA - CD 8 hinge + TM - 4-1BB - CD3z Version 1 | MALPVTALLLPLALLLHAARPEVQLQQSGPELVKPGAS VKISCKTSGYTFTESTIHWVKQSHGKSLEWIGGISPNNG GSPFNQKFKGKATLTVDKSSSTVYMELRSLSSEDSAVY YCAKWVRGAMDFWGQGTSVTVSSGGGGSGGGGSGG GGSGGGGSDIVLTQSPASLAVSLGQRATISCRASESVDY YGMSLMNWFQQKPGQPPKLVIYAASNQGSGVPARFSG SGSGTDFRLNIHPLEEDDTGMYFCQQSKEAPPTFGGGT KLEIKGGGGSGGGGSGGGGSGGGGSDIVLTQSPPSLAM SLGKRATISCRASESVTILGSHLIHWYQQKPGQPPTLLIQ LASNVQTGVPARFSGSGSRTDFTLTIDPVEEDDVAVYY CLQSRTIPRTFGGGTKLEIKGSTSGSGKPGSGEGSTKGQI QLVQSGPELKKPGETVKISCKASGYTFTDYSINWVKRA PGKGLKWMGWINTETREPAYAYDFRGRFAFSLETSAST AYLQINNLKYEDTATYFCALDYSYAMDYWGQGTSVT VSSAAATTTPAPRPPTPAPTTTTPAPRPPTPAPTIASQPLS LRPEACRPAAGGAVHTRGLDFACDIYIWAPLAGTCGVL LLSLVITLYCKRGRKKLLYIFKQPFMRPVQTTQEEDGCS |

TABLE 2-continued

| | | Amino Acid Sequences |
|---|---|---|
| SEQ ID NO: | Description | Sequence |

|  |  |  |
|---|---|---|
|  |  | CRFPEEEEGGCELRVKFSRSADAPAYQQGQNQLYNELN LGRREEYDVLDKRRGRDPEMGGKPRRKNPQEGLYNEL QKDKMAEAYSEIGMKGERRRGKGHDGLYQGLSTATK DTYDALHMQALPPR |
| 19 | CD8 Leader - anti-BCMA - linker - anti-TACI H-L - CD8 hinge + TM - 4-1BB - CD3z Version 1 | MALPVTALLLPLALLLHAARPDIVLTQSPPSLAMSLGKR ATISCRASESVTILGSHLIHWYQQKPGQPPTLLIQLASNV QTGVPARFSGSGSRTDFTLTIDPVEEDDVAVYYCLQSR TIPRTFGGGTKLEIKGSTSGSGKPGSGEGSTKGQIQLVQS GPELKKPGETVKISCKASGYTFTDYSINWVKRAPGKGL KWMGWINTETREPAYAYDFRGRFAFSLETSASTAYLQI NNLKYEDTATYFCALDYSYAMDYWGQGTSVTVSSAA ATTTPAPRPPTPAPTGGGGSGGGGSGGGGSGGGGSEVQ LQQSGPELVKPGASVKISCKTSGYTFTESTIHWVKQSHG KSLEWIGGISPNNGGSPFNQKFKGKATLTVDKSSSTVY MELRSLSSEDSAVYYCAKWVRGAMDFWGQGTSVTVS SGGGGSGGGGSGGGGSGGGGSDIVLTQSPASLAVSLGQ RATISCRASESVDYYGMSLMNWFQQKPGQPPKLVIYA ASNQGSGVPARFSGSGSGTDFRLNIHPLEEDDTGMYFC QQSKEAPPTFGGGTKLEIKTTTPAPRPPTPAPTIASQPLS LRPEACRPAAGGAVHTRGLDFACDIYIWAPLAGTCGVL LLSLVITLYCKRGRKKLLYIFKQPFMRPVQTTQEEDGCS CRFPEEEEGGCELRVKFSRSADAPAYQQGQNQLYNELN LGRREEYDVLDKRRGRDPEMGGKPRRKNPQEGLYNEL QKDKMAEAYSEIGMKGERRRGKGHDGLYQGLSTATK DTYDALHMQALPPR |
| 20 | CD8 Leader - anti-TACI L-H - linker - anti-BCMA - CD8 hinge + TM - 4-1BB - CD3z Version 1 | MALPVTALLLPLALLLHAARPDIVLTQSPASLAVSLGQR ATISCRASESVDYYGMSLMNWFQQKPGQPPKLVIYAAS NQGSGVPARFSGSGSGTDFRLNIHPLEEDDTGMYFCQQ SKEAPPTFGGGTKLEIKGGGGSGGGGSGGGGSGGGGSE VQLQQSGPELVKPGASVKISCKTSGYTFTESTIHWVKQS HGKSLEWIGGISPNNGGSPFNQKFKGKATLTVDKSSST VYMELRSLSSEDSAVYYCAKWVRGAMDFWGQGTSVT VSSGGGGSGGGGSGGGGSGGGGSDIVLTQSPPSLAMSL GKRATISCRASESVTILGSHLIHWYQQKPGQPPTLLIQL ASNVQTGVPARFSGSGSRTDFTLTIDPVEEDDVAVYYC LQSRTIPRTFGGGTKLEIKGSTSGSGKPGSGEGSTKGQIQ LVQSGPELKKPGETVKISCKASGYTFTDYSINWVKRAP GKGLKWMGWINTETREPAYAYDFRGRFAFSLETSAST AYLQINNLKYEDTATYFCALDYSYAMDYWGQGTSVT VSSAAATTTPAPRPPTPAPTTTTPAPRPPTPAPTIASQPLS LRPEACRPAAGGAVHTRGLDFACDIYIWAPLAGTCGVL LLSLVITLYCKRGRKKLLYIFKQPFMRPVQTTQEEDGCS CRFPEEEEGGCELRVKFSRSADAPAYQQGQNQLYNELN LGRREEYDVLDKRRGRDPEMGGKPRRKNPQEGLYNEL QKDKMAEAYSEIGMKGERRRGKGHDGLYQGLSTATK DTYDALHMQALPPR |
| 21 | CD8 Leader - anti-BCMA - linker - anti-TACI L-H - CD 8 hinge + TM - 4-1BB - CD3z Version 1 | MALPVTALLLPLALLLHAARPDIVLTQSPPSLAMSLGKR ATISCRASESVTILGSHLIHWYQQKPGQPPTLLIQLASNV QTGVPARFSGSGSRTDFTLTIDPVEEDDVAVYYCLQSR TIPRTFGGGTKLEIKGSTSGSGKPGSGEGSTKGQIQLVQS GPELKKPGETVKISCKASGYTFTDYSINWVKRAPGKGL KWMGWINTETREPAYAYDFRGRFAFSLETSASTAYLQI NNLKYEDTATYFCALDYSYAMDYWGQGTSVTVSSAA ATTTPAPRPPTPAPTGGGGSGGGGSGGGGSGGGGSDIV LTQSPASLAVSLGQRATISCRASESVDYYGMSLMNWFQ QKPGQPPKLVIYAASNQGSGVPARFSGSGSGTDFRLNIH PLEEDDTGMYFCQQSKEAPPTFGGGTKLEIKGGGGSGG GGSGGGGSGGGGSEVQLQQSGPELVKPGASVKISCKTS GYTFTESTIHWVKQSHGKSLEWIGGISPNNGGSPFNQKF KGKATLTVDKSSSTVYMELRSLSSEDSAVYYCAKWVR GAMDFWGQGTSVTVSSTTTPAPRPPTPAPTIASQPLSLR PEACRPAAGGAVHTRGLDFACDIYIWAPLAGTCGVLLL SLVITLYCKRGRKKLLYIFKQPFMRPVQTTQEEDGCSCR FPEEEEGGCELRVKFSRSADAPAYQQGQNQLYNELNLG RREEYDVLDKRRGRDPEMGGKPRRKNPQEGLYNELQK DKMAEAYSEIGMKGERRRGKGHDGLYQGLSTATKDT YDALHMQALPPR |

TABLE 2-continued

| Amino Acid Sequences | | |
| --- | --- | --- |
| SEQ ID NO: | Description | Sequence |
| 22 | CD8 Leader - anti-TACI H-L - linker - anti-BCMA - CD8 hinge + TM - 4-1BB - CD3z Version 2 | MALPVTALLLPLALLLHAARPEVQLQQSGPELVKPGAS VKISCKTSGYTFTESTIHWVKQSHGKSLEWIGGISPNNG GSPFNQKFKGKATLTVDKSSSTVYMELRSLSSEDSAVY YCAKWVRGAMDFWGQGTSVTVSSGGGGSGGGGSGG GGSGGGGSDIVLTQSPASLAVSLGQRATISCRASESVDY YGMSLMNWFQQKPGQPPKLVIYAASNQGSGVPARFSG SGSGTDFRLNIHPLEEDDTGMYFCQQSKEAPPTFGGGT KLEIKGGGGSGGGGSGGGGSGGGGSDIVLTQSPPSLAM SLGKRATISCRASESVTILGSHLIHWYQQKPGQPPTLLIQ LASNVQTGVPARFSGSGSRTDFTLTIDPVEEDDVAVYY CLQSRTIPRTFGGGTKLEIKGSTSGSGKPGSGEGSTKGQI QLVQSGPELKKPGETVKISCKASGYTFTDYSINWVKRA PGKGLKWMGWINTETREPAYAYDFRGRFAFSLETSAST AYLQINNLKYEDTATYFCALDYSYAMDYWGQGTSVT VSSAAATTTPAPRPPTPAPTIASQPLSLRPEACRPAAGG AVHTRGLDFACDIYIWAPLAGTCGVLLLSLVITLYCKR GRKKLLYIFKQPFMRPVQTTQEEDGCSCRFPEEEEGGC ELRVKFSRSADAPAYQQGQNQLYNELNLGRREEYDVL DKRRGRDPEMGGKPRRKNPQEGLYNELQKDKMAEAY SEIGMKGERRRGKGHDGLYQGLSTATKDTYDALHMQ ALPPR |
| 23 | CD8 Leader - anti-BCMA - linker - anti-TACI H-L - CD8 hinge + TM - 4-1BB - CD3z Version 2 | MALPVTALLLPLALLLHAARPDIVLTQSPPSLAMSLGKR ATISCRASESVTILGSHLIHWYQQKPGQPPTLLIQLASNV QTGVPARFSGSGSRTDFTLTIDPVEEDDVAVYYCLQSR TIPRTFGGGTKLEIKGSTSGSGKPGSGEGSTKGQIQLVQS GPELKKPGETVKISCKASGYTFTDYSINWVKRAPGKGL KWMGWINTETREPAYAYDFRGRFAFSLETSASTAYLQI NNLKYEDTATYFCALDYSYAMDYWGQGTSVTVSSAA AGGGGSGGGGSGGGGSGGGGSEVQLQQSGPELVKPGA SVKISCKTSGYTFTESTIHWVKQSHGKSLEWIGGISPNN GGSPFNQKFKGKATLTVDKSSSTVYMELRSLSSEDSAV YYCAKWVRGAMDFWGQGTSVTVSSGGGGSGGGGSG GGGSGGGGSDIVLTQSPASLAVSLGQRATISCRASESVD YYGMSLMNWFQQKPGQPPKLVIYAASNQGSGVPARFS GSGSGTDFRLNIHPLEEDDTGMYFCQQSKEAPPTFGGG TKLEIKTTTPAPRPPTPAPTIASQPLSLRPEACRPAAGGA VHTRGLDFACDIYIWAPLAGTCGVLLLSLVITLYCKRG RKKLLYIFKQPFMRPVQTTQEEDGCSCRFPEEEEGGCEL RVKFSRSADAPAYQQGQNQLYNELNLGRREEYDVLDK RRGRDPEMGGKPRRKNPQEGLYNELQKDKMAEAYSEI GMKGERRRGKGHDGLYQGLSTATKDTYDALHMQALP PR |
| 24 | CD8 Leader - anti-TACI L-H - linker - anti-BCMA - CD8 hinge + TM - 4-1BB - CD3z Version 2 | MALPVTALLLPLALLLHAARPDIVLTQSPASLAVSLGQR ATISCRASESVDYYGMSLMNWFQQKPGQPPKLVIYAAS NQGSGVPARFSGSGSGTDFRLNIHPLEEDDTGMYFCQQ SKEAPPTFGGGTKLEIKGGGGSGGGGSGGGGSGGGGSE VQLQQSGPELVKPGASVKISCKTSGYTFTESTIHWVKQS HGKSLEWIGGISPNNGGSPFNQKFKGKATLTVDKSSST VYMELRSLSSEDSAVYYCAKWVRGAMDFWGQGTSVT VSSGGGGSGGGGSGGGGSGGGGSDIVLTQSPPSLAMSL GKRATISCRASESVTILGSHLIHWYQQKPGQPPTLLIQL ASNVQTGVPARFSGSGSRTDFTLTIDPVEEDDVAVYYC LQSRTIPRTFGGGTKLEIKGSTSGSGKPGSGEGSTKGQIQ LVQSGPELKKPGETVKISCKASGYTFTDYSINWVKRAP GKGLKWMGWINTETREPAYAYDFRGRFAFSLETSAST AYLQINNLKYEDTATYFCALDYSYAMDYWGQGTSVT VSSAAATTTPAPRPPTPAPTIASQPLSLRPEACRPAAGG AVHTRGLDFACDIYIWAPLAGTCGVLLLSLVITLYCKR GRKKLLYIFKQPFMRPVQTTQEEDGCSCRFPEEEEGGC ELRVKFSRSADAPAYQQGQNQLYNELNLGRREEYDVL DKRRGRDPEMGGKPRRKNPQEGLYNELQKDKMAEAY SEIGMKGERRRGKGHDGLYQGLSTATKDTYDALHMQ ALPPR |
| 25 | CD8 Leader - anti-BCMA - linker - anti-TACI L-H - CD8 hinge + TM - 4-1BB - CD3z Version 2 | MALPVTALLLPLALLLHAARPDIVLTQSPPSLAMSLGKR ATISCRASESVTILGSHLIHWYQQKPGQPPTLLIQLASNV QTGVPARFSGSGSRTDFTLTIDPVEEDDVAVYYCLQSR TIPRTFGGGTKLEIKGSTSGSGKPGSGEGSTKGQIQLVQS GPELKKPGETVKISCKASGYTFTDYSINWVKRAPGKGL KWMGWINTETREPAYAYDFRGRFAFSLETSASTAYLQI NNLKYEDTATYFCALDYSYAMDYWGQGTSVTVSSAA AGGGGSGGGGSGGGGSGGGGSDIVLTQSPASLAVSLG QRATISCRASESVDYYGMSLMNWFQQKPGQPPKLVIY |

TABLE 2-continued

| Amino Acid Sequences | | |
|---|---|---|
| SEQ ID NO: | Description | Sequence |
| | | AASNQGSGVPARFSGSGSGTDFRLNIHPLEEDDTGMYF CQQSKEAPPTFGGGTKLEIKGGGGSGGGGSGGGGSGG GGSEVQLQQSGPELVKPGASVKISCKTSGYTFTESTIHW VKQSHGKSLEWIGGISPNNGGSPFNQKFKGKATLTVDK SSSTVYMELRSLSSEDSAVYYCAKWVRGAMDFWGQG TSVTVSSTTTPAPRPPTPAPTIASQPLSLRPEACRPAAGG AVHTRGLDFACDIYIWAPLAGTCGVLLLSLVITLYCKR GRKKLLYIFKQPFMRPVQTTQEEDGCSCRFPEEEEGGC ELRVKFSRSADAPAYQQGQNQLYNELNLGRREEYDVL DKRRGRDPEMGGKPRRKNPQEGLYNELQKDKMAEAY SEIGMKGERRRGKGHDGLYQGLSTATKDTYDALHMQ ALPPR |

TABLE 3

| Complementarity-Determining Region (CDR) Definitions | | | |
|---|---|---|---|
| | IMGT[1] | Kabat[2] | Chothia[3] |
| CDR-H1 | 27-38 | 31-35 | 26-32 |
| CDR-H2 | 56-65 | 50-65 | 53-55 |
| CDR-H3 | 105-116/117 | 95-102 | 96-101 |
| CDR-L1 | 27-38 | 24-34 | 26-32 |
| CDR-L2 | 56-65 | 50-56 | 50-52 |
| CDR-L3 | 105-116/117 | 89-97 | 91-96 |

[1]IMGT ®, the international ImMunoGeneTics information system ®, imgt.org, Lefranc, M.-P. et al., Nucleic Acids Res., 27: 209-212 (1999)
[2]Kabat et al. (1991) Sequences of Proteins of Immunological Interest, Fifth Edition, U.S. Department of Health and Human Services, NIH Publication No. 91-3242
[3]Chothia et al., J. Mol. Biol. 196: 901-917 (1987)).

TABLE 4

| Anti-TACI Complementarity-Determining Region (CDR) Amino Acid Sequences | | | |
|---|---|---|---|
| No. system | IMGT | Kabat | Chothia |
| CDR-H1 | GYTFTEST (SEQ ID NO: 26) | ESTIH (SEQ ID NO: 32) | GYTFTES (SEQ ID NO: 37) |
| CDR-H2 | ISPNNGGS (SEQ ID NO: 27) | GISPNNGGSPFNQKFKG (SEQ ID NO: 33) | NNG (SEQ ID NO: 38) |
| CDR-H3 | AKWVRGAMDF (SEQ ID NO: 28) | WVRGAMDF (SEQ ID NO: 34) | VRGAMD (SEQ ID NO: 39) |
| CDR-L1 | ESVDYYGMSL (SEQ ID NO: 29) | RASESVDYYGMSLMN (SEQ ID NO: 35) | SESVDYYGMSL (SEQ ID NO: 40) |
| CDR-L2 | AAS (SEQ ID NO: 30) | AASNQGS (SEQ ID NO: 36) | AAS (SEQ ID NO: 30) |
| CDR-L3 | QQSKEAPPT (SEQ ID NO: 31) | QQSKEAPPT (SEQ ID NO: 31) | SKEAPP (SEQ ID NO: 41) |

Some embodiments of the technology described herein can be defined according to any of the following numbered paragraphs:

1. An isolated antibody that specifically binds transmembrane activator and calcium modulator and cyclophilin ligand interactor (TACI), wherein the antibody binds to TACI with a $K_D$ of about 2 nM or lower.

2. The antibody of claim 1, wherein the antibody binds to TACI with a $K_D$ between about 500 pM and about 1 nM.

3. The antibody of paragraphs 1 or 2, wherein the antibody binds to TACI with a $K_D$ between about 700 pM and about 900 pM.

4. The antibody of any one of paragraphs 1-3, wherein the antibody binds to TACI with a $K_D$ of about 861 pM.

5. An isolated antibody that specifically binds TACI, wherein the antibody includes a heavy chain variable domain (VH) including an amino acid sequence having at least 80% sequence identity to the amino acid sequence of SEQ ID NO: 1 and/or a light chain variable domain (VL) including an amino acid sequence having at least 80% sequence identity to the amino acid sequence of SEQ ID NO: 2.

6. The antibody of paragraph 5, wherein the VH includes an amino acid sequence having at least 85% sequence identity to the amino acid sequence of SEQ ID NO: 1 and the VL includes an amino acid sequence having at least 85% sequence identity the amino acid sequence of SEQ ID NO: 2.

7. The antibody of paragraph 5, wherein the VH includes an amino acid sequence having at least 90% sequence identity to the amino acid sequence of SEQ ID NO: 1 and the VL includes an amino acid sequence having at least 90% sequence identity the amino acid sequence of SEQ ID NO: 2.

8. The antibody of paragraph 5, wherein the VH includes an amino acid sequence having at least 98% sequence identity to the amino acid sequence of SEQ ID NO: 1 and the VL includes an amino acid sequence having at least 98% sequence identity the amino acid sequence of SEQ ID NO: 2.

9. The antibody of paragraph 5, wherein the VH includes an amino acid sequence having at least 99% sequence identity to the amino acid sequence of SEQ ID NO: 1 and the VL includes an amino acid sequence having at least 99% sequence identity the amino acid sequence of SEQ ID NO: 2.

10. An isolated antibody that specifically binds to TACI, wherein the antibody includes a VH including the amino acid sequence of SEQ ID NO: 1 and a VL including the amino acid sequence of SEQ ID NO: 2.

11. The antibody of any one of paragraphs 1-10, wherein the antibody is a monoclonal, human, humanized, or chimeric antibody.

12. The antibody of paragraph 11, wherein the antibody is a monoclonal antibody.

13. The antibody of any one of paragraphs 1-12, wherein the antibody is a full-length antibody.

14. The antibody of any one of paragraphs 1-12, wherein the antibody is an antibody fragment that specifically binds TACI.

15. The antibody of paragraph 14, wherein the antibody fragment is selected from the group consisting of Fab, Fab', Fab'-SH, Fv, scFv, and (Fab')$_2$ fragments.

16. The antibody of any one of paragraphs 1-15, wherein the antibody is an IgG antibody.

17. The antibody of paragraph 16, wherein the antibody is an IgG1 antibody.

18. A composition including the antibody of any one of paragraphs 1-17.

19. A polynucleotide encoding the antibody of any one of paragraphs 1-17.

20. A vector including the polynucleotide of paragraph 19.

21. A host cell including the vector of paragraph 16.

22. The host cell of paragraph 21, wherein the host cell is a mammalian cell.

23. The host cell of paragraph 22, wherein the mammalian cell is a Chinese hamster ovary (CHO) cell.

24. The host cell of paragraph 21, wherein the host cell is a prokaryotic cell.

25. The host cell of paragraph 24, wherein the prokaryotic cell is *E. coli*.

26. A method of producing an antibody that specifically binds TACI, the method including culturing the host cell of any one of paragraphs 21-25 in a culture medium.

27. The method of paragraph 22, wherein the method further includes recovering the antibody from the host cell or the culture medium.

28. An antibody-drug conjugate including the antibody of any one of paragraphs 1-27.

29. A chimeric antigen receptor (CAR) polypeptide including an extracellular target binding domain, wherein the extracellular target binding domain includes a TACI-binding domain.

30. The CAR polypeptide of paragraph 29, wherein the CAR polypeptide includes a transmembrane domain and an intracellular signaling domain.

31. The CAR polypeptide of paragraph 29 or 30, further including one or more co-stimulatory domains.

32. The CAR polypeptide of any one of paragraphs 29-31, wherein the TACI-binding domain does not include APRIL, BAFF, CAMLG, or a portion thereof.

33. The CAR polypeptide of any one of paragraphs 29-32, wherein the TACI-binding domain binds to TACI with a $K_D$ of about 2 nM or lower.

34. The CAR polypeptide of any one of paragraphs 29-33, wherein the TACI-binding domain binds to TACI with a $K_D$ between about 500 pM and about 1 nM.

35. The CAR polypeptide of any one of paragraphs 29-34, wherein the TACI-binding domain binds to TACI with a $K_D$ between about 700 pM and about 900 pM.

36. The CAR polypeptide of any one of paragraphs 29-35, wherein the TACI-binding domain binds to TACI with a $K_D$ of about 861 pM.

37. The CAR polypeptide of any one of paragraphs 29-36, wherein the TACI-binding domain includes an antibody or an antigen binding fragment thereof.

38. A CAR polypeptide including an extracellular target binding domain including the antibody of any one of paragraphs 1-17 or an antigen binding fragment thereof.

39. The CAR polypeptide of any one of paragraphs 29-38, wherein the TACI-binding domain includes an anti-TACI single chain variable fragment (scFv).

40. The CAR polypeptide of paragraph 39, wherein the anti-TACI scFv includes a heavy chain variable domain (VH) including an amino acid sequence having at least 90% sequence identity to the amino acid sequence of SEQ ID NO: 1.

41. The CAR polypeptide of paragraph 40, wherein the VH includes the amino acid sequence of SEQ ID NO: 1.

42. The CAR polypeptide of any one of paragraphs 39-41, wherein the anti-TACI scFv includes a light chain variable domain (VL) including an amino acid sequence having at least 90% sequence identity to the amino acid sequence of SEQ ID NO: 2.

43. The CAR polypeptide of paragraph 42, wherein the VL includes the amino acid sequence of SEQ ID NO: 2.

44. The CAR polypeptide of any one of paragraphs 39-43, wherein the anti-TACI scFv includes a VH including the amino acid sequence of SEQ ID NO: 1 and a VL including the amino acid sequence of SEQ ID NO: 2.

45. The CAR polypeptide of any one of paragraphs 40-44, wherein the VH is positioned N-terminal to the VL.

46. The CAR polypeptide of any one of paragraphs 40-44, wherein the VL is positioned N-terminal to the VH.

47. The CAR polypeptide of any one of paragraphs 40-46, wherein the VH and the VL are connected via a linker sequence.

48. The CAR polypeptide of paragraph 47, wherein the linker sequence includes the amino acid sequence of SEQ ID NO: 3, 14, 15, 16, or 17.

49. The CAR polypeptide of paragraph 48, wherein the linker sequence includes the amino acid sequence of SEQ ID NO: 3.

50. The CAR polypeptide of any one of paragraphs 29-49, wherein the TACI-binding domain includes an amino acid sequence having at least 90% sequence identity to the amino acid sequence of SEQ ID NO: 4 or 5.

51. The CAR polypeptide of paragraph 49 or 50, wherein the TACI-binding domain includes the amino acid sequence of SEQ ID NO: 4 or 5.

52. The CAR polypeptide of any one of paragraphs 29-51, wherein the transmembrane domain includes a hinge/transmembrane domain.

53. The CAR polypeptide of paragraph 52, the hinge/transmembrane domain includes the hinge/transmembrane domain of an immunoglobulin-like protein, CD28, CD8, or 4-1BB.

54. The CAR polypeptide of paragraph 53, wherein the hinge/transmembrane domain is the hinge/transmembrane domain of CD8, optionally wherein the hinge/transmembrane domain of CD8 includes the amino acid sequence of SEQ ID NO: 7.

55. The CAR polypeptide of any one of paragraphs 29-54, wherein the intracellular signaling domain includes the intracellular signaling domain of CD3ζ, CD3ε, or CD3θ.

56. The CAR polypeptide of paragraph 55, wherein the intracellular signaling domain includes the intracellular signaling domain of CD3, optionally wherein the intracellular signaling domain of CD3ζ includes the amino acid sequence of SEQ ID NO: 9.

57. The CAR polypeptide of any one of paragraphs 31-56, wherein the co-stimulatory domain includes the co-stimulatory domain of 4-1BB, CD28, CD27, ICOS, or OX40.

58. The CAR polypeptide of paragraph 57, wherein the co-stimulatory domain includes the co-stimulatory domain of 4-1BB, optionally wherein the co-stimulatory domain of 4-1BB includes the amino acid sequence of SEQ ID NO: 8.

59. The CAR polypeptide of any one of paragraphs 29-58, wherein the CAR polypeptide includes an amino acid sequence having at least 90% sequence identity to the amino acid sequence of SEQ ID NO: 10, 11, 12, or 13.

60. The CAR polypeptide of any one of paragraphs 29-58, wherein the extracellular target binding domain further includes a target-binding domain that binds to a second target that is not TACI.

61. The CAR polypeptide paragraph 60, wherein the second target is B cell maturation antigen (BCMA).

62. The CAR polypeptide of paragraph 60 or 61, wherein the target-binding domain includes a ligand of the second target.

63. The CAR polypeptide of paragraph 60 or 61, wherein the target-binding domain includes an antibody or antigen-binding fragment thereof.

64. The CAR polypeptide of paragraph 63, wherein the antibody or antigen-binding fragment thereof includes an scFv.

65. The CAR polypeptide of paragraph 64, wherein the scFv is an anti-BCMA scFv.

66. The CAR polypeptide of paragraph 65, wherein the anti-BCMA scFv is positioned N-terminal to the anti-TACI scFv.

67. The CAR polypeptide of paragraph 65, wherein the anti-TACI scFv is positioned N-terminal to the anti-BCMA scFv.

68. A CAR polypeptide including the amino acid sequence of SEQ ID NO: 10.

69. A CAR polypeptide including the amino acid sequence of SEQ ID NO: 11.

70. A CAR polypeptide including the amino acid sequence of SEQ ID NO: 12.

71. A CAR polypeptide including the amino acid sequence of SEQ ID NO: 13.

72. A polynucleotide encoding the CAR polypeptide of any one of paragraphs 29-71.

73. The polynucleotide of paragraph 72, further including a suicide gene.

74. The polynucleotide of paragraph 72 or 73, further including a sequence encoding a signal sequence.

75. A mammalian cell including the CAR polypeptide of any one of paragraphs 29-71 and/or the polynucleotide of any one of paragraphs 72-74.

76. The mammalian cell of paragraph 75, wherein the mammalian cell is an induced pluripotent stem cell (iPSC).

77. The mammalian cell of paragraph 75, wherein the mammalian cell is an immune cell.

78. The mammalian cell of paragraph 77, wherein the immune cell is a T cell or a natural killer (NK) cell.

79. The mammalian cell of any one of paragraphs 75-78, wherein the mammalian cell is a human cell.

80. A bispecific antibody that binds TACI and CD3, wherein the bispecific antibody includes a TACI-binding domain and a CD3-binding domain.

81. The bispecific antibody of paragraph 80, wherein the TACI-binding domain binds to TACI with a $K_D$ of about 2 nM or lower.

82. The bispecific antibody of paragraph 80 or 81, wherein the TACI-binding domain binds to TACI with a $K_D$ between about 500 pM and about 1 nM.

83. The bispecific antibody of any one of paragraphs 80-82, wherein the TACI-binding domain binds to TACI with a $K_D$ between about 700 pM and about 900 pM.

84. The bispecific antibody of any one of paragraphs 80-83, wherein the TACI-binding domain binds to TACI with a $K_D$ of about 861 pM.

85. The bispecific antibody of any one of paragraphs 80-84, wherein the TACI-binding domain includes a VH including an amino acid sequence having at least 95% sequence identity to the amino acid sequence of SEQ ID NO: 1 and/or a VL including an amino acid sequence having at least 95% sequence identity to the amino acid sequence of SEQ ID NO: 2.

86. A bispecific antibody that specifically binds to TACI and CD3, wherein the bispecific antibody includes a TACI-binding domain and a CD3-binding domain, wherein the TACI-binding domain includes a VH including the amino acid sequence of SEQ ID NO: 1 and a VL including the amino acid sequence of SEQ ID NO: 2.

87. The bispecific antibody of any one of paragraphs 80-86, wherein the TACI-binding domain is positioned N-terminal to the CD3-binding domain.

88. The bispecific antibody of any one of paragraphs 80-86, wherein the CD3-binding domain is positioned N-terminal to the TACI-binding domain.

89. The bispecific antibody of any one of paragraphs 80-88, wherein the TACI-binding domain and the CD3-binding domain are connected by a linker sequence.

90. The bispecific antibody of paragraph 89, wherein the linker sequence includes the amino acid sequence of SEQ ID NO: 3, 14, 15, 16, or 17.

91. The bispecific antibody of any one of paragraphs 80-90, wherein the bispecific antibody is a monoclonal, human, humanized, or chimeric antibody.

92. The bispecific antibody of paragraph 91, wherein the bispecific antibody is a monoclonal antibody.

93. The bispecific antibody of any one of paragraphs 80-92, wherein the bispecific antibody is a full-length antibody.

94. The bispecific antibody of any one of paragraphs 80-92, wherein the bispecific antibody is an antibody fragment that specifically binds TACI and CD3.

95. The antibody of paragraph 94, wherein the antibody fragment is selected from the group consisting of Fab, Fab', Fab'-SH, Fv, scFv, and (Fab')$_2$ fragments.

96. The bispecific antibody of any one of paragraphs 80-95, wherein the bispecific antibody is an IgG antibody.

97. The bispecific antibody of paragraph 96, wherein the bispecific antibody is an IgG1 antibody.

98. A composition including the bispecific antibody of any one of paragraphs 80-97.

99. A polynucleotide encoding the bispecific antibody of any one of paragraphs 80-97.

100. A vector including the polynucleotide of paragraph 99.

101. A host cell including the vector of paragraph 100.

102. The host cell of paragraph 101, wherein the host cell is a mammalian cell.

103. The host cell of paragraph 102, wherein the mammalian cell is a Chinese hamster ovary (CHO) cell.

104. The host cell of paragraph 101, wherein the host cell is a prokaryotic cell.

105. The host cell of paragraph 104, wherein the prokaryotic cell is *E. coli*.

106. A method of producing a bispecific antibody that specifically binds TACI and CD3, the method including culturing the host cell of any one of paragraphs 101-105 in a culture medium.

107. The method of paragraph 106, wherein the method further includes recovering the bispecific antibody from the host cell or the culture medium.

108. A method of treating a disease or disorder in a subject in need thereof, wherein the method includes administering to the subject one or more of the following: (i) the CAR polypeptide of any one of paragraphs 29-71, the polynucleotide of any one of paragraphs 19, 72-74, and 99, and/or the mammalian cell of any one of paragraphs 22, 23, 75-79, 102, and 103; (ii) the antibody of any one of paragraphs 1-17, (iii) the antibody-drug conjugate of paragraph 28; and (iv) the bispecific antibody of any one of paragraphs 80-97.

109. The method of paragraph 108, wherein the disease or disorder is a cancer, an autoimmune disorder, or a plasma cell disease or disorder.

110. The method of paragraph 109, wherein disease or disorder is cancer.

111. The method of paragraph 110, wherein the cancer includes cells expressing TACI.

112. The method of paragraph 111, wherein the cancer is multiple myeloma.

113. The method of any one of paragraphs 110-112, wherein the subject is resistant to anti-BCMA therapy.

114. The method of paragraph 109, wherein the disease or disorder is an autoimmune disease or disorder.

115. The method of paragraph 114, wherein the autoimmune disease or disorder is characterized by a high titer of antibodies contributing to the autoimmune disorder.

116. The method of paragraph 114 or 115, wherein the autoimmune disease or disorder is transplant rejection, graft versus host disease, or hemophilia with Factor inhibitors.

117. The method of paragraph 109, wherein the disease or disorder is a plasma cell disease or disorder.

118. The method of paragraph 117, wherein the plasma cell disease or disorder is plasma cell dyscrasias, plasmacytoma, plasma cell leukemia, multiple myeloma, Waldenstrom's macroglobulinemia, solitary plasmacytoma, extramedullary plasmacytoma, osteosclerotic myeloma, heavy chain diseases, monoclonal gammopathy of undetermined significance, and smoldering multiple myeloma.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. An antibody that specifically binds to transmembrane activator and calcium modulator and cyclophilin ligand interactor (TACI), wherein the antibody comprises:

(i) a heavy chain complementarity-determining region 1 (CDR-H1), a heavy chain complementarity-determining region 2 (CDR-H2), and a heavy chain complementarity-determining region 3 (CDR-H3) of a heavy chain variable region (VH) comprising the amino acid sequence of SEQ ID NO: 1; and (ii) a light chain complementarity-determining region 1 (CDR-L1), a light chain complementarity-determining region 2 (CDR-L2), and a light chain complementarity-determining region 3 (CDR-L3) of a light chain variable region (VL) comprising the amino acid sequence of SEQ ID NO: 2.

2. The antibody of claim 1, wherein the antibody comprises:

(i) a CDR-H1 as set forth in SEQ ID NO: 26, a CDR-H2 as set forth in SEQ ID NO: 27, and a CDR-H3 as set forth in SEQ ID NO: 28; a CDR-L1 as set forth in SEQ ID NO: 29, a CDR-L2 as set forth in SEQ ID NO: 30, and a CDR-L3 as set forth in SEQ ID NO: 31;

(ii) a CDR-H1 as set forth in SEQ ID NO: 32, a CDR-H2 as set forth in SEQ ID NO: 33, and a CDR-H3 as set forth in SEQ ID NO: 34; a CDR-L1 as set forth in SEQ ID NO: 35, a CDR-L2 as set forth in SEQ ID NO: 36, and a CDR-L3 as set forth in SEQ ID NO: 31; or (iii) a CDR-H1 as set forth in SEQ ID NO: 37, a CDR-H2 as set forth in SEQ ID NO: 38, and a CDR-H3 as set forth in SEQ ID NO: 39; a CDR-L1 as set forth in SEQ ID NO: 40, a CDR-L2 as set forth in SEQ ID NO: 30, and a CDR-L3 as set forth in SEQ ID NO: 41.

3. A composition comprising the antibody of claim 1.

4. A polynucleotide encoding the antibody of claim 1.

5. A vector comprising the polynucleotide of claim 4.

6. A host cell comprising the vector of claim 5.

7. A method of producing an antibody that specifically binds TACI, the method comprising culturing the host cell claim 6 in a culture medium.

8. An antibody-drug conjugate comprising the antibody of claim 1.

9. A chimeric antigen receptor (CAR) polypeptide comprising an extracellular target binding domain comprising the antibody of claim 1 or an antigen binding fragment thereof.

10. The CAR polypeptide of claim 9 comprising an amino acid sequence of any one of SEQ ID NOs: 12, 13, or 18-25.

* * * * *

```
                         SEQUENCE LISTING

<160> NUMBER OF SEQ ID NOS: 41

<210> SEQ ID NO 1
<211> LENGTH: 117
<212> TYPE: PRT
<213> ORGANISM: Artificial Sequence
<220> FEATURE:
<223> OTHER INFORMATION: Synthetic

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Ser
            20                  25                  30

Thr Ile His Trp Val Lys Gln Ser His Gly Lys Ser Leu Glu Trp Ile
        35                  40                  45

Gly Gly Ile Ser Pro Asn Asn Gly Gly Ser Pro Phe Asn Gln Lys Phe
    50                  55                  60

Lys Gly Lys Ala Thr Leu Thr Val Asp Lys Ser Ser Ser Thr Val Tyr
65                  70                  75                  80

Met Glu Leu Arg Ser Leu Ser Ser Glu Asp Ser Ala Val Tyr Tyr Cys
                85                  90                  95

Ala Lys Trp Val Arg Gly Ala Met Asp Phe Trp Gly Gln Gly Thr Ser
                100                 105                 110

Val Thr Val Ser Ser
            115

<210> SEQ ID NO 2
<211> LENGTH: 111
<212> TYPE: PRT
<213> ORGANISM: Artificial Sequence
<220> FEATURE:
<223> OTHER INFORMATION: Synthetic

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Tyr
                20                  25                  30

Gly Met Ser Leu Met Asn Trp Phe Gln Gln Lys Pro Gly Gln Pro Pro
        35                  40                  45

Lys Leu Val Ile Tyr Ala Ala Ser Asn Gln Gly Ser Gly Val Pro Ala
```

```
                50                  55                  60

Arg Phe Ser Gly Ser Gly Ser Gly Thr Asp Phe Arg Leu Asn Ile His
65                  70                  75                  80

Pro Leu Glu Glu Asp Asp Thr Gly Met Tyr Phe Cys Gln Gln Ser Lys
                85                  90                  95

Glu Ala Pro Pro Thr Phe Gly Gly Gly Thr Lys Leu Glu Ile Lys
            100                 105                 110

<210> SEQ ID NO 3
<211> LENGTH: 20
<212> TYPE: PRT
<213> ORGANISM: Artificial Sequence
<220> FEATURE:
<223> OTHER INFORMATION: Synthetic

<400> SEQUENCE: 3

Gly Gly Gly Gly Ser Gly Gly Gly Gly Ser Gly Gly Gly Gly Ser Gly
1               5                   10                  15

Gly Gly Gly Ser
            20

<210> SEQ ID NO 4
<211> LENGTH: 248
<212> TYPE: PRT
<213> ORGANISM: Artificial Sequence
<220> FEATURE:
<223> OTHER INFORMATION: Synthetic

<400> SEQUENCE: 4

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Ser
            20                  25                  30

Thr Ile His Trp Val Lys Gln Ser His Gly Lys Ser Leu Glu Trp Ile
        35                  40                  45

Gly Gly Ile Ser Pro Asn Asn Gly Gly Ser Pro Phe Asn Gln Lys Phe
    50                  55                  60

Lys Gly Lys Ala Thr Leu Thr Val Asp Lys Ser Ser Ser Thr Val Tyr
65                  70                  75                  80

Met Glu Leu Arg Ser Leu Ser Ser Glu Asp Ser Ala Val Tyr Tyr Cys
                85                  90                  95

Ala Lys Trp Val Arg Gly Ala Met Asp Phe Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Ile Val Leu Thr Gln Ser
    130                 135                 140

Pro Ala Ser Leu Ala Val Ser Leu Gly Gln Arg Ala Thr Ile Ser Cys
145                 150                 155                 160

Arg Ala Ser Glu Ser Val Asp Tyr Tyr Gly Met Ser Leu Met Asn Trp
                165                 170                 175

Phe Gln Gln Lys Pro Gly Gln Pro Pro Lys Leu Val Ile Tyr Ala Ala
            180                 185                 190

Ser Asn Gln Gly Ser Gly Val Pro Ala Arg Phe Ser Gly Ser Gly Ser
        195                 200                 205

Gly Thr Asp Phe Arg Leu Asn Ile His Pro Leu Glu Glu Asp Asp Thr
    210                 215                 220
```

```
Gly Met Tyr Phe Cys Gln Gln Ser Lys Glu Ala Pro Pro Thr Phe Gly
225                 230                 235                 240

Gly Gly Thr Lys Leu Glu Ile Lys
            245

<210> SEQ ID NO 5
<211> LENGTH: 248
<212> TYPE: PRT
<213> ORGANISM: Artificial Sequence
<220> FEATURE:
<223> OTHER INFORMATION: Synthetic

<400> SEQUENCE: 5

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Met Ser Leu Met Asn Trp Phe Gln Gln Lys Pro Gly Gln Pro Pro
            35                  40                  45

Lys Leu Val Ile Tyr Ala Ala Ser Asn Gln Gly Ser Gly Val Pro Ala
        50                  55                  60

Arg Phe Ser Gly Ser Gly Ser Gly Thr Asp Phe Arg Leu Asn Ile His
65                  70                  75                  80

Pro Leu Glu Glu Asp Asp Thr Gly Met Tyr Phe Cys Gln Gln Ser Lys
                85                  90                  95

Glu Ala Pro Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gly Gly
            115                 120                 125

Gly Gly Ser Glu Val Gln Leu Gln Gln Ser Gly Pro Glu Leu Val Lys
        130                 135                 140

Pro Gly Ala Ser Val Lys Ile Ser Cys Lys Thr Ser Gly Tyr Thr Phe
145                 150                 155                 160

Thr Glu Ser Thr Ile His Trp Val Lys Gln Ser His Gly Lys Ser Leu
                165                 170                 175

Glu Trp Ile Gly Gly Ile Ser Pro Asn Asn Gly Gly Ser Pro Phe Asn
            180                 185                 190

Gln Lys Phe Lys Gly Lys Ala Thr Leu Thr Val Asp Lys Ser Ser Ser
            195                 200                 205

Thr Val Tyr Met Glu Leu Arg Ser Leu Ser Ser Glu Asp Ser Ala Val
        210                 215                 220

Tyr Tyr Cys Ala Lys Trp Val Arg Gly Ala Met Asp Phe Trp Gly Gln
225                 230                 235                 240

Gly Thr Ser Val Thr Val Ser Ser
            245

<210> SEQ ID NO 6
<211> LENGTH: 21
<212> TYPE: PRT
<213> ORGANISM: Artificial Sequence
<220> FEATURE:
<223> OTHER INFORMATION: Synthetic

<400> SEQUENCE: 6

Met Ala Leu Pro Val Thr Ala Leu Leu Leu Pro Leu Ala Leu Leu Leu
1               5                   10                  15

His Ala Ala Arg Pro
            20
```

```
<210> SEQ ID NO 7
<211> LENGTH: 69
<212> TYPE: PRT
<213> ORGANISM: Artificial Sequence
<220> FEATURE:
<223> OTHER INFORMATION: Synthetic

<400> SEQUENCE: 7

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 8
<211> LENGTH: 42
<212> TYPE: PRT
<213> ORGANISM: Artificial Sequence
<220> FEATURE:
<223> OTHER INFORMATION: Synthetic

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 9
<211> LENGTH: 112
<212> TYPE: PRT
<213> ORGANISM: Artificial Sequence
<220> FEATURE:
<223> OTHER INFORMATION: Synthetic

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 10
<211> LENGTH: 471
```

```
<212> TYPE: PRT
<213> ORGANISM: Artificial Sequence
<220> FEATURE:
<223> OTHER INFORMATION: Synthetic

<400> SEQUENCE: 10

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Ser
                20                  25                  30

Thr Ile His Trp Val Lys Gln Ser His Gly Lys Ser Leu Glu Trp Ile
            35                  40                  45

Gly Gly Ile Ser Pro Asn Asn Gly Gly Ser Pro Phe Asn Gln Lys Phe
        50                  55                  60

Lys Gly Lys Ala Thr Leu Thr Val Asp Lys Ser Ser Ser Thr Val Tyr
65                  70                  75                  80

Met Glu Leu Arg Ser Leu Ser Ser Glu Asp Ser Ala Val Tyr Tyr Cys
                85                  90                  95

Ala Lys Trp Val Arg Gly Ala Met Asp Phe Trp Gly Gln Gly Thr Ser
            100                 105                 110

Val Thr Val Ser Ser Gly Gly Gly Ser Gly Gly Gly Gly Ser Gly
            115                 120                 125

Gly Gly Gly Ser Gly Gly Gly Ser Asp Ile Val Leu Thr Gln Ser
        130                 135                 140

Pro Ala Ser Leu Ala Val Ser Leu Gly Gln Arg Ala Thr Ile Ser Cys
145                 150                 155                 160

Arg Ala Ser Glu Ser Val Asp Tyr Tyr Gly Met Ser Leu Met Asn Trp
                165                 170                 175

Phe Gln Gln Lys Pro Gly Gln Pro Pro Lys Leu Val Ile Tyr Ala Ala
            180                 185                 190

Ser Asn Gln Gly Ser Gly Val Pro Ala Arg Phe Ser Gly Ser Gly Ser
            195                 200                 205

Gly Thr Asp Phe Arg Leu Asn Ile His Pro Leu Glu Glu Asp Asp Thr
        210                 215                 220

Gly Met Tyr Phe Cys Gln Gln Ser Lys Glu Ala Pro Pro Thr Phe Gly
225                 230                 235                 240

Gly Gly Thr Lys Leu Glu Ile Lys Thr Thr Thr Pro Ala Pro Arg Pro
            245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
        290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
            325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
            355                 360                 365

Ala Pro Ala Tyr Gln Gln Gly Gln Asn Gln Leu Tyr Asn Glu Leu Asn
        370                 375                 380
```

-continued

```
Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 11
<211> LENGTH: 471
<212> TYPE: PRT
<213> ORGANISM: Artificial Sequence
<220> FEATURE:
<223> OTHER INFORMATION: Synthetic

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Tyr
                20                  25                  30

Gly Met Ser Leu Met Asn Trp Phe Gln Gln Lys Pro Gly Gln Pro Pro
            35                  40                  45

Lys Leu Val Ile Tyr Ala Ala Ser Asn Gln Gly Ser Gly Val Pro Ala
    50                  55                  60

Arg Phe Ser Gly Ser Gly Ser Gly Thr Asp Phe Arg Leu Asn Ile His
65                  70                  75                  80

Pro Leu Glu Glu Asp Asp Thr Gly Met Tyr Phe Cys Gln Gln Ser Lys
                85                  90                  95

Glu Ala Pro Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gly Gly
            115                 120                 125

Gly Gly Ser Glu Val Gln Leu Gln Gln Ser Gly Pro Glu Leu Val Lys
    130                 135                 140

Pro Gly Ala Ser Val Lys Ile Ser Cys Lys Thr Ser Gly Tyr Thr Phe
145                 150                 155                 160

Thr Glu Ser Thr Ile His Trp Val Lys Gln Ser His Gly Lys Ser Leu
                165                 170                 175

Glu Trp Ile Gly Gly Ile Ser Pro Asn Asn Gly Gly Ser Pro Phe Asn
            180                 185                 190

Gln Lys Phe Lys Gly Lys Ala Thr Leu Thr Val Asp Lys Ser Ser Ser
            195                 200                 205

Thr Val Tyr Met Glu Leu Arg Ser Leu Ser Ser Glu Asp Ser Ala Val
    210                 215                 220

Tyr Tyr Cys Ala Lys Trp Val Arg Gly Ala Met Asp Phe Trp Gly Gln
225                 230                 235                 240

Gly Thr Ser Val Thr Val Ser Ser Thr Thr Thr Pro Ala Pro Arg Pro
            245                 250                 255

Pro Thr Pro Ala Pro Thr Ile Ala Ser Gln Pro Leu Ser Leu Arg Pro
            260                 265                 270
```

-continued

```
Glu Ala Cys Arg Pro Ala Ala Gly Gly Ala Val His Thr Arg Gly Leu
        275             280             285

Asp Phe Ala Cys Asp Ile Tyr Ile Trp Ala Pro Leu Ala Gly Thr Cys
    290             295             300

Gly Val Leu Leu Leu Ser Leu Val Ile Thr Leu Tyr Cys Lys Arg Gly
305             310             315             320

Arg Lys Lys Leu Leu Tyr Ile Phe Lys Gln Pro Phe Met Arg Pro Val
            325             330             335

Gln Thr Thr Gln Glu Glu Asp Gly Cys Ser Cys Arg Phe Pro Glu Glu
            340             345             350

Glu Glu Gly Gly Cys Glu Leu Arg Val Lys Phe Ser Arg Ser Ala Asp
            355             360             365

Ala Pro Ala Tyr Gln Gln Gly Gln Asn Gln Leu Tyr Asn Glu Leu Asn
    370             375             380

Leu Gly Arg Arg Glu Glu Tyr Asp Val Leu Asp Lys Arg Arg Gly Arg
385             390             395             400

Asp Pro Glu Met Gly Gly Lys Pro Arg Arg Lys Asn Pro Gln Glu Gly
            405             410             415

Leu Tyr Asn Glu Leu Gln Lys Asp Lys Met Ala Glu Ala Tyr Ser Glu
            420             425             430

Ile Gly Met Lys Gly Glu Arg Arg Arg Gly Lys Gly His Asp Gly Leu
            435             440             445

Tyr Gln Gly Leu Ser Thr Ala Thr Lys Asp Thr Tyr Asp Ala Leu His
    450             455             460

Met Gln Ala Leu Pro Pro Arg
465             470

<210> SEQ ID NO 12
<211> LENGTH: 492
<212> TYPE: PRT
<213> ORGANISM: Artificial Sequence
<220> FEATURE:
<223> OTHER INFORMATION: Synthetic

<400> SEQUENCE: 12

Met Ala Leu Pro Val Thr Ala Leu Leu Leu Pro Leu Ala Leu Leu Leu
1               5               10              15

His Ala Ala Arg Pro Glu Val Gln Leu Gln Gln Ser Gly Pro Glu Leu
            20              25              30

Val Lys Pro Gly Ala Ser Val Lys Ile Ser Cys Lys Thr Ser Gly Tyr
            35              40              45

Thr Phe Thr Glu Ser Thr Ile His Trp Val Lys Gln Ser His Gly Lys
    50              55              60

Ser Leu Glu Trp Ile Gly Gly Ile Ser Pro Asn Asn Gly Gly Ser Pro
65              70              75              80

Phe Asn Gln Lys Phe Lys Gly Lys Ala Thr Leu Thr Val Asp Lys Ser
            85              90              95

Ser Ser Thr Val Tyr Met Glu Leu Arg Ser Leu Ser Ser Glu Asp Ser
            100             105             110

Ala Val Tyr Tyr Cys Ala Lys Trp Val Arg Gly Ala Met Asp Phe Trp
            115             120             125

Gly Gln Gly Thr Ser Val Thr Val Ser Ser Gly Gly Gly Gly Ser Gly
        130             135             140

Gly Gly Gly Ser Gly Gly Gly Gly Ser Gly Gly Gly Gly Ser Asp Ile
145             150             155             160
```

-continued

```
Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Tyr Tyr Gly Met
                180                 185                 190

Ser Leu Met Asn Trp Phe Gln Gln Lys Pro Gly Gln Pro Pro Lys Leu
                195                 200                 205

Val Ile Tyr Ala Ala Ser Asn Gln Gly Ser Gly Val Pro Ala Arg Phe
            210                 215                 220

Ser Gly Ser Gly Ser Gly Thr Asp Phe Arg Leu Asn Ile His Pro Leu
225                 230                 235                 240

Glu Glu Asp Asp Thr Gly Met Tyr Phe Cys Gln Gln Ser Lys Glu Ala
                245                 250                 255

Pro Pro Thr Phe Gly Gly Gly Thr Lys Leu Glu Ile Lys Thr Thr Thr
                260                 265                 270

Pro Ala Pro Arg Pro Pro Thr Pro Ala Pro Thr Ile Ala Ser Gln Pro
                275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 13
<211> LENGTH: 492
<212> TYPE: PRT
<213> ORGANISM: Artificial Sequence
<220> FEATURE:
<223> OTHER INFORMATION: Synthetic

<400> SEQUENCE: 13

```
Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
                20                  25                  30
```

-continued

```
Ala Val Ser Leu Gly Gln Arg Ala Thr Ile Ser Cys Arg Ala Ser Glu
        35              40              45

Ser Val Asp Tyr Tyr Gly Met Ser Leu Met Asn Trp Phe Gln Gln Lys
        50              55              60

Pro Gly Gln Pro Pro Lys Leu Val Ile Tyr Ala Ala Ser Asn Gln Gly
65              70              75              80

Ser Gly Val Pro Ala Arg Phe Ser Gly Ser Gly Ser Gly Thr Asp Phe
                85              90              95

Arg Leu Asn Ile His Pro Leu Glu Glu Asp Asp Thr Gly Met Tyr Phe
                100             105             110

Cys Gln Gln Ser Lys Glu Ala Pro Pro Thr Phe Gly Gly Gly Thr Lys
            115             120             125

Leu Glu Ile Lys Gly Gly Gly Gly Ser Gly Gly Gly Ser Gly Gly
        130             135             140

Gly Gly Ser Gly Gly Gly Gly Ser Glu Val Gln Leu Gln Gln Ser Gly
145             150             155             160

Pro Glu Leu Val Lys Pro Gly Ala Ser Val Lys Ile Ser Cys Lys Thr
                165             170             175

Ser Gly Tyr Thr Phe Thr Glu Ser Thr Ile His Trp Val Lys Gln Ser
                180             185             190

His Gly Lys Ser Leu Glu Trp Ile Gly Gly Ile Ser Pro Asn Asn Gly
            195             200             205

Gly Ser Pro Phe Asn Gln Lys Phe Lys Gly Lys Ala Thr Leu Thr Val
        210             215             220

Asp Lys Ser Ser Ser Thr Val Tyr Met Glu Leu Arg Ser Leu Ser Ser
225             230             235             240

Glu Asp Ser Ala Val Tyr Tyr Cys Ala Lys Trp Val Arg Gly Ala Met
                245             250             255

Asp Phe Trp Gly Gln Gly Thr Ser Val Thr Val Ser Ser Thr Thr Thr
            260             265             270

Pro Ala Pro Arg Pro Pro Thr Pro Ala Pro Thr Ile Ala Ser Gln Pro
            275             280             285

Leu Ser Leu Arg Pro Glu Ala Cys Arg Pro Ala Ala Gly Gly Ala Val
        290             295             300

His Thr Arg Gly Leu Asp Phe Ala Cys Asp Ile Tyr Ile Trp Ala Pro
305             310             315             320

Leu Ala Gly Thr Cys Gly Val Leu Leu Leu Ser Leu Val Ile Thr Leu
                325             330             335

Tyr Cys Lys Arg Gly Arg Lys Lys Leu Leu Tyr Ile Phe Lys Gln Pro
            340             345             350

Phe Met Arg Pro Val Gln Thr Thr Gln Glu Glu Asp Gly Cys Ser Cys
            355             360             365

Arg Phe Pro Glu Glu Glu Glu Gly Gly Cys Glu Leu Arg Val Lys Phe
        370             375             380

Ser Arg Ser Ala Asp Ala Pro Ala Tyr Gln Gln Gly Gln Asn Gln Leu
385             390             395             400

Tyr Asn Glu Leu Asn Leu Gly Arg Arg Glu Glu Tyr Asp Val Leu Asp
                405             410             415

Lys Arg Arg Gly Arg Asp Pro Glu Met Gly Gly Lys Pro Arg Arg Lys
            420             425             430

Asn Pro Gln Glu Gly Leu Tyr Asn Glu Leu Gln Lys Asp Lys Met Ala
        435             440             445

Glu Ala Tyr Ser Glu Ile Gly Met Lys Gly Glu Arg Arg Arg Gly Lys
```

-continued

```
        450                 455                 460
Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Gly Gly Gly Ser Gly Gly Gly Ser Gly Gly Gly Ser
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 18
<212> TYPE: PRT
<213> ORGANISM: Artificial Sequence
<220> FEATURE:
<223> OTHER INFORMATION: Synthetic

<400> SEQUENCE: 16

Gly Ser Thr Ser Gly Ser Gly Lys Pro Gly Ser Gly Glu Gly Ser Thr
1               5                   10                  15

Lys Gly

<210> SEQ ID NO 17
<211> LENGTH: 18
<212> TYPE: PRT
<213> ORGANISM: Artificial Sequence
<220> FEATURE:
<223> OTHER INFORMATION: Synthetic

<400> SEQUENCE: 17

Gly Gly Ser Ser Arg Ser Ser Ser Ser Gly Gly Gly Gly Ser Gly Gly
1               5                   10                  15

Gly Gly

<210> SEQ ID NO 18
<211> LENGTH: 775
<212> TYPE: PRT
<213> ORGANISM: Artificial Sequence
<220> FEATURE:
<223> OTHER INFORMATION: Synthetic

<400> SEQUENCE: 18

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30
```

-continued

```
Val Lys Pro Gly Ala Ser Val Lys Ile Ser Cys Lys Thr Ser Gly Tyr
        35                  40                  45

Thr Phe Thr Glu Ser Thr Ile His Trp Val Lys Gln Ser His Gly Lys
        50                  55                  60

Ser Leu Glu Trp Ile Gly Gly Ile Ser Pro Asn Asn Gly Gly Ser Pro
65                  70                  75                  80

Phe Asn Gln Lys Phe Lys Gly Lys Ala Thr Leu Thr Val Asp Lys Ser
                85                  90                  95

Ser Ser Thr Val Tyr Met Glu Leu Arg Ser Leu Ser Ser Glu Asp Ser
                100                 105                 110

Ala Val Tyr Tyr Cys Ala Lys Trp Val Arg Gly Ala Met Asp Phe Trp
                115                 120                 125

Gly Gln Gly Thr Ser Val Thr Val Ser Ser Gly Gly Gly Ser Gly
        130                 135                 140

Gly Gly Gly Ser Gly Gly Gly Ser Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Tyr Tyr Gly Met
                180                 185                 190

Ser Leu Met Asn Trp Phe Gln Gln Lys Pro Gly Gln Pro Pro Lys Leu
                195                 200                 205

Val Ile Tyr Ala Ala Ser Asn Gln Gly Ser Gly Val Pro Ala Arg Phe
        210                 215                 220

Ser Gly Ser Gly Ser Gly Thr Asp Phe Arg Leu Asn Ile His Pro Leu
225                 230                 235                 240

Glu Glu Asp Asp Thr Gly Met Tyr Phe Cys Gln Gln Ser Lys Glu Ala
                245                 250                 255

Pro Pro Thr Phe Gly Gly Gly Thr Lys Leu Glu Ile Lys Gly Gly Gly
                260                 265                 270

Gly Ser Gly Gly Gly Gly Ser Gly Gly Gly Ser Gly Gly Gly Gly
        275                 280                 285

Ser Asp Ile Val Leu Thr Gln Ser Pro Pro Ser Leu Ala Met Ser Leu
        290                 295                 300

Gly Lys Arg Ala Thr Ile Ser Cys Arg Ala Ser Glu Ser Val Thr Ile
305                 310                 315                 320

Leu Gly Ser His Leu Ile His Trp Tyr Gln Gln Lys Pro Gly Gln Pro
                325                 330                 335

Pro Thr Leu Leu Ile Gln Leu Ala Ser Asn Val Gln Thr Gly Val Pro
                340                 345                 350

Ala Arg Phe Ser Gly Ser Gly Ser Arg Thr Asp Phe Thr Leu Thr Ile
                355                 360                 365

Asp Pro Val Glu Glu Asp Asp Val Ala Val Tyr Tyr Cys Leu Gln Ser
        370                 375                 380

Arg Thr Ile Pro Arg Thr Phe Gly Gly Gly Thr Lys Leu Glu Ile Lys
385                 390                 395                 400

Gly Ser Thr Ser Gly Ser Gly Lys Pro Gly Ser Gly Glu Gly Ser Thr
                405                 410                 415

Lys Gly Gln Ile Gln Leu Val Gln Ser Gly Pro Glu Leu Lys Lys Pro
                420                 425                 430

Gly Glu Thr Val Lys Ile Ser Cys Lys Ala Ser Gly Tyr Thr Phe Thr
        435                 440                 445
```

-continued

```
Asp Tyr Ser Ile Asn Trp Val Lys Arg Ala Pro Gly Lys Gly Leu Lys
    450                 455                 460

Trp Met Gly Trp Ile Asn Thr Glu Thr Arg Glu Pro Ala Tyr Ala Tyr
465                 470                 475                 480

Asp Phe Arg Gly Arg Phe Ala Phe Ser Leu Glu Thr Ser Ala Ser Thr
                485                 490                 495

Ala Tyr Leu Gln Ile Asn Asn Leu Lys Tyr Glu Asp Thr Ala Thr Tyr
                500                 505                 510

Phe Cys Ala Leu Asp Tyr Ser Tyr Ala Met Asp Tyr Trp Gly Gln Gly
                515                 520                 525

Thr Ser Val Thr Val Ser Ser Ala Ala Ala Thr Thr Thr Pro Ala Pro
    530                 535                 540

Arg Pro Pro Thr Pro Ala Pro Thr Thr Thr Pro Ala Pro Arg Pro
545                 550                 555                 560

Pro Thr Pro Ala Pro Thr Ile Ala Ser Gln Pro Leu Ser Leu Arg Pro
                565                 570                 575

Glu Ala Cys Arg Pro Ala Ala Gly Gly Ala Val His Thr Arg Gly Leu
                580                 585                 590

Asp Phe Ala Cys Asp Ile Tyr Ile Trp Ala Pro Leu Ala Gly Thr Cys
                595                 600                 605

Gly Val Leu Leu Leu Ser Leu Val Ile Thr Leu Tyr Cys Lys Arg Gly
    610                 615                 620

Arg Lys Lys Leu Leu Tyr Ile Phe Lys Gln Pro Phe Met Arg Pro Val
625                 630                 635                 640

Gln Thr Thr Gln Glu Glu Asp Gly Cys Ser Cys Arg Phe Pro Glu Glu
                645                 650                 655

Glu Glu Gly Gly Cys Glu Leu Arg Val Lys Phe Ser Arg Ser Ala Asp
                660                 665                 670

Ala Pro Ala Tyr Gln Gln Gly Gln Asn Gln Leu Tyr Asn Glu Leu Asn
                675                 680                 685

Leu Gly Arg Arg Glu Glu Tyr Asp Val Leu Asp Lys Arg Arg Gly Arg
    690                 695                 700

Asp Pro Glu Met Gly Gly Lys Pro Arg Arg Lys Asn Pro Gln Glu Gly
705                 710                 715                 720

Leu Tyr Asn Glu Leu Gln Lys Asp Lys Met Ala Glu Ala Tyr Ser Glu
                725                 730                 735

Ile Gly Met Lys Gly Glu Arg Arg Arg Gly Lys Gly His Asp Gly Leu
                740                 745                 750

Tyr Gln Gly Leu Ser Thr Ala Thr Lys Asp Thr Tyr Asp Ala Leu His
                755                 760                 765

Met Gln Ala Leu Pro Pro Arg
    770                 775
```

<210> SEQ ID NO 19
<211> LENGTH: 775
<212> TYPE: PRT
<213> ORGANISM: Artificial Sequence
<220> FEATURE:
<223> OTHER INFORMATION: Synthetic

<400> SEQUENCE: 19

```
Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
            20                  25                  30
```

-continued

```
Ala Met Ser Leu Gly Lys Arg Ala Thr Ile Ser Cys Arg Ala Ser Glu
        35              40              45

Ser Val Thr Ile Leu Gly Ser His Leu Ile His Trp Tyr Gln Gln Lys
    50              55              60

Pro Gly Gln Pro Pro Thr Leu Leu Ile Gln Leu Ala Ser Asn Val Gln
65              70              75              80

Thr Gly Val Pro Ala Arg Phe Ser Gly Ser Gly Ser Arg Thr Asp Phe
                85              90              95

Thr Leu Thr Ile Asp Pro Val Glu Glu Asp Asp Val Ala Val Tyr Tyr
            100             105             110

Cys Leu Gln Ser Arg Thr Ile Pro Arg Thr Phe Gly Gly Gly Thr Lys
            115             120             125

Leu Glu Ile Lys Gly Ser Thr Ser Gly Ser Gly Lys Pro Gly Ser Gly
    130             135             140

Glu Gly Ser Thr Lys Gly Gln Ile Gln Leu Val Gln Ser Gly Pro Glu
145             150             155             160

Leu Lys Lys Pro Gly Glu Thr Val Lys Ile Ser Cys Lys Ala Ser Gly
                165             170             175

Tyr Thr Phe Thr Asp Tyr Ser Ile Asn Trp Val Lys Arg Ala Pro Gly
            180             185             190

Lys Gly Leu Lys Trp Met Gly Trp Ile Asn Thr Glu Thr Arg Glu Pro
            195             200             205

Ala Tyr Ala Tyr Asp Phe Arg Gly Arg Phe Ala Phe Ser Leu Glu Thr
    210             215             220

Ser Ala Ser Thr Ala Tyr Leu Gln Ile Asn Asn Leu Lys Tyr Glu Asp
225             230             235             240

Thr Ala Thr Tyr Phe Cys Ala Leu Asp Tyr Ser Tyr Ala Met Asp Tyr
            245             250             255

Trp Gly Gln Gly Thr Ser Val Thr Val Ser Ser Ala Ala Ala Thr Thr
            260             265             270

Thr Pro Ala Pro Arg Pro Pro Thr Pro Ala Pro Thr Gly Gly Gly Gly
    275             280             285

Ser Gly Gly Gly Gly Ser Gly Gly Gly Gly Ser Gly Gly Gly Gly Ser
    290             295             300

Glu Val Gln Leu Gln Gln Ser Gly Pro Glu Leu Val Lys Pro Gly Ala
305             310             315             320

Ser Val Lys Ile Ser Cys Lys Thr Ser Gly Tyr Thr Phe Thr Glu Ser
                325             330             335

Thr Ile His Trp Val Lys Gln Ser His Gly Lys Ser Leu Glu Trp Ile
            340             345             350

Gly Gly Ile Ser Pro Asn Asn Gly Gly Ser Pro Phe Asn Gln Lys Phe
            355             360             365

Lys Gly Lys Ala Thr Leu Thr Val Asp Lys Ser Ser Ser Thr Val Tyr
    370             375             380

Met Glu Leu Arg Ser Leu Ser Ser Glu Asp Ser Ala Val Tyr Tyr Cys
385             390             395             400

Ala Lys Trp Val Arg Gly Ala Met Asp Phe Trp Gly Gln Gly Thr Ser
                405             410             415

Val Thr Val Ser Ser Gly Gly Gly Ser Gly Gly Gly Gly Ser Gly
            420             425             430

Gly Gly Gly Ser Gly Gly Gly Gly Ser Asp Ile Val Leu Thr Gln Ser
            435             440             445

Pro Ala Ser Leu Ala Val Ser Leu Gly Gln Arg Ala Thr Ile Ser Cys
```

-continued

```
            450                 455                 460

Arg Ala Ser Glu Ser Val Asp Tyr Tyr Gly Met Ser Leu Met Asn Trp
465                 470                 475                 480

Phe Gln Gln Lys Pro Gly Gln Pro Pro Lys Leu Val Ile Tyr Ala Ala
                485                 490                 495

Ser Asn Gln Gly Ser Gly Val Pro Ala Arg Phe Ser Gly Ser Gly Ser
            500                 505                 510

Gly Thr Asp Phe Arg Leu Asn Ile His Pro Leu Glu Glu Asp Asp Thr
            515                 520                 525

Gly Met Tyr Phe Cys Gln Gln Ser Lys Glu Ala Pro Pro Thr Phe Gly
            530                 535                 540

Gly Gly Thr Lys Leu Glu Ile Lys Thr Thr Thr Pro Ala Pro Arg Pro
545                 550                 555                 560

Pro Thr Pro Ala Pro Thr Ile Ala Ser Gln Pro Leu Ser Leu Arg Pro
                565                 570                 575

Glu Ala Cys Arg Pro Ala Ala Gly Gly Ala Val His Thr Arg Gly Leu
                580                 585                 590

Asp Phe Ala Cys Asp Ile Tyr Ile Trp Ala Pro Leu Ala Gly Thr Cys
                595                 600                 605

Gly Val Leu Leu Leu Ser Leu Val Ile Thr Leu Tyr Cys Lys Arg Gly
            610                 615                 620

Arg Lys Lys Leu Leu Tyr Ile Phe Lys Gln Pro Phe Met Arg Pro Val
625                 630                 635                 640

Gln Thr Thr Gln Glu Glu Asp Gly Cys Ser Cys Arg Phe Pro Glu Glu
                645                 650                 655

Glu Glu Gly Gly Cys Glu Leu Arg Val Lys Phe Ser Arg Ser Ala Asp
                660                 665                 670

Ala Pro Ala Tyr Gln Gln Gly Gln Asn Gln Leu Tyr Asn Glu Leu Asn
                675                 680                 685

Leu Gly Arg Arg Glu Glu Tyr Asp Val Leu Asp Lys Arg Arg Gly Arg
            690                 695                 700

Asp Pro Glu Met Gly Gly Lys Pro Arg Arg Lys Asn Pro Gln Glu Gly
705                 710                 715                 720

Leu Tyr Asn Glu Leu Gln Lys Asp Lys Met Ala Glu Ala Tyr Ser Glu
                725                 730                 735

Ile Gly Met Lys Gly Glu Arg Arg Arg Gly Lys Gly His Asp Gly Leu
                740                 745                 750

Tyr Gln Gly Leu Ser Thr Ala Thr Lys Asp Thr Tyr Asp Ala Leu His
            755                 760                 765

Met Gln Ala Leu Pro Pro Arg
770                 775

<210> SEQ ID NO 20
<211> LENGTH: 775
<212> TYPE: PRT
<213> ORGANISM: Artificial Sequence
<220> FEATURE:
<223> OTHER INFORMATION: Synthetic

<400> SEQUENCE: 20

Met Ala Leu Pro Val Thr Ala Leu Leu Leu Pro Leu Ala Leu Leu Leu
1                   5                   10                  15

His Ala Ala Arg Pro Asp Ile Val Leu Thr Gln Ser Pro Ala Ser Leu
                20                  25                  30

Ala Val Ser Leu Gly Gln Arg Ala Thr Ile Ser Cys Arg Ala Ser Glu
```

```
          35                     40                      45
Ser Val Asp Tyr Tyr Gly Met Ser Leu Met Asn Trp Phe Gln Gln Lys
    50                  55                  60

Pro Gly Gln Pro Pro Lys Leu Val Ile Tyr Ala Ala Ser Asn Gln Gly
65                  70                  75                  80

Ser Gly Val Pro Ala Arg Phe Ser Gly Ser Gly Ser Gly Thr Asp Phe
                85                  90                  95

Arg Leu Asn Ile His Pro Leu Glu Glu Asp Asp Thr Gly Met Tyr Phe
            100                 105                 110

Cys Gln Gln Ser Lys Glu Ala Pro Pro Thr Phe Gly Gly Gly Thr Lys
            115                 120                 125

Leu Glu Ile Lys Gly Gly Gly Gly Ser Gly Gly Gly Ser Gly Gly
    130                 135                 140

Gly Gly Ser Gly Gly Gly Gly Ser Glu Val Gln Leu Gln Gln Ser Gly
145                 150                 155                 160

Pro Glu Leu Val Lys Pro Gly Ala Ser Val Lys Ile Ser Cys Lys Thr
                165                 170                 175

Ser Gly Tyr Thr Phe Thr Glu Ser Thr Ile His Trp Val Lys Gln Ser
            180                 185                 190

His Gly Lys Ser Leu Glu Trp Ile Gly Gly Ile Ser Pro Asn Asn Gly
            195                 200                 205

Gly Ser Pro Phe Asn Gln Lys Phe Lys Gly Lys Ala Thr Leu Thr Val
    210                 215                 220

Asp Lys Ser Ser Ser Thr Val Tyr Met Glu Leu Arg Ser Leu Ser Ser
225                 230                 235                 240

Glu Asp Ser Ala Val Tyr Tyr Cys Ala Lys Trp Val Arg Gly Ala Met
                245                 250                 255

Asp Phe Trp Gly Gln Gly Thr Ser Val Thr Val Ser Ser Gly Gly Gly
            260                 265                 270

Gly Ser Gly Gly Gly Gly Ser Gly Gly Gly Ser Gly Gly Gly Gly
            275                 280                 285

Ser Asp Ile Val Leu Thr Gln Ser Pro Pro Ser Leu Ala Met Ser Leu
    290                 295                 300

Gly Lys Arg Ala Thr Ile Ser Cys Arg Ala Ser Glu Ser Val Thr Ile
305                 310                 315                 320

Leu Gly Ser His Leu Ile His Trp Tyr Gln Gln Lys Pro Gly Gln Pro
            325                 330                 335

Pro Thr Leu Leu Ile Gln Leu Ala Ser Asn Val Gln Thr Gly Val Pro
            340                 345                 350

Ala Arg Phe Ser Gly Ser Gly Ser Arg Thr Asp Phe Thr Leu Thr Ile
            355                 360                 365

Asp Pro Val Glu Glu Asp Asp Val Ala Val Tyr Tyr Cys Leu Gln Ser
    370                 375                 380

Arg Thr Ile Pro Arg Thr Phe Gly Gly Gly Thr Lys Leu Glu Ile Lys
385                 390                 395                 400

Gly Ser Thr Ser Gly Ser Gly Lys Pro Gly Ser Gly Glu Gly Ser Thr
                405                 410                 415

Lys Gly Gln Ile Gln Leu Val Gln Ser Gly Pro Glu Leu Lys Lys Pro
            420                 425                 430

Gly Glu Thr Val Lys Ile Ser Cys Lys Ala Ser Gly Tyr Thr Phe Thr
            435                 440                 445

Asp Tyr Ser Ile Asn Trp Val Lys Arg Ala Pro Gly Lys Gly Leu Lys
    450                 455                 460
```

-continued

```
Trp Met Gly Trp Ile Asn Thr Glu Thr Arg Glu Pro Ala Tyr Ala Tyr
465                 470                 475                 480

Asp Phe Arg Gly Arg Phe Ala Phe Ser Leu Glu Thr Ser Ala Ser Thr
                    485                 490                 495

Ala Tyr Leu Gln Ile Asn Asn Leu Lys Tyr Glu Asp Thr Ala Thr Tyr
                500                 505                 510

Phe Cys Ala Leu Asp Tyr Ser Tyr Ala Met Asp Tyr Trp Gly Gln Gly
            515                 520                 525

Thr Ser Val Thr Val Ser Ser Ala Ala Ala Thr Thr Thr Pro Ala Pro
            530                 535                 540

Arg Pro Pro Thr Pro Ala Pro Thr Thr Thr Thr Pro Ala Pro Arg Pro
545                 550                 555                 560

Pro Thr Pro Ala Pro Thr Ile Ala Ser Gln Pro Leu Ser Leu Arg Pro
                565                 570                 575

Glu Ala Cys Arg Pro Ala Ala Gly Gly Ala Val His Thr Arg Gly Leu
            580                 585                 590

Asp Phe Ala Cys Asp Ile Tyr Ile Trp Ala Pro Leu Ala Gly Thr Cys
            595                 600                 605

Gly Val Leu Leu Leu Ser Leu Val Ile Thr Leu Tyr Cys Lys Arg Gly
        610                 615                 620

Arg Lys Lys Leu Leu Tyr Ile Phe Lys Gln Pro Phe Met Arg Pro Val
625                 630                 635                 640

Gln Thr Thr Gln Glu Glu Asp Gly Cys Ser Cys Arg Phe Pro Glu Glu
                645                 650                 655

Glu Glu Gly Gly Cys Glu Leu Arg Val Lys Phe Ser Arg Ser Ala Asp
            660                 665                 670

Ala Pro Ala Tyr Gln Gln Gly Gln Asn Gln Leu Tyr Asn Glu Leu Asn
            675                 680                 685

Leu Gly Arg Arg Glu Glu Tyr Asp Val Leu Asp Lys Arg Arg Gly Arg
        690                 695                 700

Asp Pro Glu Met Gly Gly Lys Pro Arg Arg Lys Asn Pro Gln Glu Gly
705                 710                 715                 720

Leu Tyr Asn Glu Leu Gln Lys Asp Lys Met Ala Glu Ala Tyr Ser Glu
                725                 730                 735

Ile Gly Met Lys Gly Glu Arg Arg Arg Gly Lys Gly His Asp Gly Leu
            740                 745                 750

Tyr Gln Gly Leu Ser Thr Ala Thr Lys Asp Thr Tyr Asp Ala Leu His
        755                 760                 765

Met Gln Ala Leu Pro Pro Arg
    770                 775

<210> SEQ ID NO 21
<211> LENGTH: 775
<212> TYPE: PRT
<213> ORGANISM: Artificial Sequence
<220> FEATURE:
<223> OTHER INFORMATION: Synthetic

<400> SEQUENCE: 21

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
                20                  25                  30

Ala Met Ser Leu Gly Lys Arg Ala Thr Ile Ser Cys Arg Ala Ser Glu
            35                  40                  45
```

```
Ser Val Thr Ile Leu Gly Ser His Leu Ile His Trp Tyr Gln Gln Lys
    50                  55                  60

Pro Gly Gln Pro Pro Thr Leu Leu Ile Gln Leu Ala Ser Asn Val Gln
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Asp Val Ala Val Tyr Tyr
                100                 105                 110

Cys Leu Gln Ser Arg Thr Ile Pro Arg Thr Phe Gly Gly Gly Thr Lys
                115                 120                 125

Leu Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
                180                 185                 190

Lys Gly Leu Lys Trp Met Gly Trp Ile Asn Thr Glu Thr Arg Glu Pro
    195                 200                 205

Ala Tyr Ala Tyr Asp Phe Arg Gly Arg Phe Ala Phe Ser Leu Glu Thr
    210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Ala Ala Ala Thr Thr
                260                 265                 270

Thr Pro Ala Pro Arg Pro Pro Thr Pro Ala Pro Thr Gly Gly Gly Gly
                275                 280                 285

Ser Gly Gly Gly Gly Ser Gly Gly Gly Gly Ser Gly Gly Gly Gly Ser
    290                 295                 300

Asp Ile Val Leu Thr Gln Ser Pro Ala Ser Leu Ala Val Ser Leu Gly
305                 310                 315                 320

Gln Arg Ala Thr Ile Ser Cys Arg Ala Ser Glu Ser Val Asp Tyr Tyr
                325                 330                 335

Gly Met Ser Leu Met Asn Trp Phe Gln Gln Lys Pro Gly Gln Pro Pro
                340                 345                 350

Lys Leu Val Ile Tyr Ala Ala Ser Asn Gln Gly Ser Gly Val Pro Ala
                355                 360                 365

Arg Phe Ser Gly Ser Gly Ser Gly Thr Asp Phe Arg Leu Asn Ile His
    370                 375                 380

Pro Leu Glu Glu Asp Asp Thr Gly Met Tyr Phe Cys Gln Gln Ser Lys
385                 390                 395                 400

Glu Ala Pro Pro Thr Phe Gly Gly Gly Thr Lys Leu Glu Ile Lys Gly
                405                 410                 415

Gly Gly Gly Ser Gly Gly Gly Gly Ser Gly Gly Gly Gly Ser Gly Gly
                420                 425                 430

Gly Gly Ser Glu Val Gln Leu Gln Gln Ser Gly Pro Glu Leu Val Lys
    435                 440                 445

Pro Gly Ala Ser Val Lys Ile Ser Cys Lys Thr Ser Gly Tyr Thr Phe
    450                 455                 460
```

-continued

```
Thr Glu Ser Thr Ile His Trp Val Lys Gln Ser His Gly Lys Ser Leu
465                 470                 475                 480

Glu Trp Ile Gly Gly Ile Ser Pro Asn Asn Gly Gly Ser Pro Phe Asn
                485                 490                 495

Gln Lys Phe Lys Gly Lys Ala Thr Leu Thr Val Asp Lys Ser Ser Ser
                500                 505                 510

Thr Val Tyr Met Glu Leu Arg Ser Leu Ser Ser Glu Asp Ser Ala Val
            515                 520                 525

Tyr Tyr Cys Ala Lys Trp Val Arg Gly Ala Met Asp Phe Trp Gly Gln
        530                 535                 540

Gly Thr Ser Val Thr Val Ser Ser Thr Thr Thr Pro Ala Pro Arg Pro
545                 550                 555                 560

Pro Thr Pro Ala Pro Thr Ile Ala Ser Gln Pro Leu Ser Leu Arg Pro
                565                 570                 575

Glu Ala Cys Arg Pro Ala Ala Gly Gly Ala Val His Thr Arg Gly Leu
                580                 585                 590

Asp Phe Ala Cys Asp Ile Tyr Ile Trp Ala Pro Leu Ala Gly Thr Cys
            595                 600                 605

Gly Val Leu Leu Leu Ser Leu Val Ile Thr Leu Tyr Cys Lys Arg Gly
        610                 615                 620

Arg Lys Lys Leu Leu Tyr Ile Phe Lys Gln Pro Phe Met Arg Pro Val
625                 630                 635                 640

Gln Thr Thr Gln Glu Glu Asp Gly Cys Ser Cys Arg Phe Pro Glu Glu
                645                 650                 655

Glu Glu Gly Gly Cys Glu Leu Arg Val Lys Phe Ser Arg Ser Ala Asp
                660                 665                 670

Ala Pro Ala Tyr Gln Gln Gly Gln Asn Gln Leu Tyr Asn Glu Leu Asn
            675                 680                 685

Leu Gly Arg Arg Glu Glu Tyr Asp Val Leu Asp Lys Arg Arg Gly Arg
        690                 695                 700

Asp Pro Glu Met Gly Gly Lys Pro Arg Arg Lys Asn Pro Gln Glu Gly
705                 710                 715                 720

Leu Tyr Asn Glu Leu Gln Lys Asp Lys Met Ala Glu Ala Tyr Ser Glu
                725                 730                 735

Ile Gly Met Lys Gly Glu Arg Arg Gly Lys Gly His Asp Gly Leu
                740                 745                 750

Tyr Gln Gly Leu Ser Thr Ala Thr Lys Asp Thr Tyr Asp Ala Leu His
        755                 760                 765

Met Gln Ala Leu Pro Pro Arg
    770                 775
```

```
<210> SEQ ID NO 22
<211> LENGTH: 761
<212> TYPE: PRT
<213> ORGANISM: Artificial Sequence
<220> FEATURE:
<223> OTHER INFORMATION: Synthetic

<400> SEQUENCE: 22

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Ile Ser Cys Lys Thr Ser Gly Tyr
        35                  40                  45
```

```
Thr Phe Thr Glu Ser Thr Ile His Trp Val Lys Gln Ser His Gly Lys
    50              55              60

Ser Leu Glu Trp Ile Gly Gly Ile Ser Pro Asn Asn Gly Gly Ser Pro
65              70              75              80

Phe Asn Gln Lys Phe Lys Gly Lys Ala Thr Leu Thr Val Asp Lys Ser
            85              90              95

Ser Ser Thr Val Tyr Met Glu Leu Arg Ser Leu Ser Ser Glu Asp Ser
            100             105             110

Ala Val Tyr Tyr Cys Ala Lys Trp Val Arg Gly Ala Met Asp Phe Trp
            115             120             125

Gly Gln Gly Thr Ser Val Thr Val Ser Ser Gly Gly Gly Gly Ser Gly
    130             135             140

Gly Gly Gly Ser Gly Gly Gly Ser Gly Gly Gly Gly Ser Asp Ile
145             150             155             160

Val Leu Thr Gln Ser Pro Ala Ser Leu Ala Val Ser Leu Gly Gln Arg
                165             170             175

Ala Thr Ile Ser Cys Arg Ala Ser Glu Ser Val Asp Tyr Tyr Gly Met
            180             185             190

Ser Leu Met Asn Trp Phe Gln Gln Lys Pro Gly Gln Pro Pro Lys Leu
        195             200             205

Val Ile Tyr Ala Ala Ser Asn Gln Gly Ser Gly Val Pro Ala Arg Phe
    210             215             220

Ser Gly Ser Gly Ser Gly Thr Asp Phe Arg Leu Asn Ile His Pro Leu
225             230             235             240

Glu Glu Asp Asp Thr Gly Met Tyr Phe Cys Gln Gln Ser Lys Glu Ala
            245             250             255

Pro Pro Thr Phe Gly Gly Gly Thr Lys Leu Glu Ile Lys Gly Gly Gly
            260             265             270

Gly Ser Gly Gly Gly Gly Ser Gly Gly Gly Gly Ser Gly Gly Gly Gly
    275             280             285

Ser Asp Ile Val Leu Thr Gln Ser Pro Pro Ser Leu Ala Met Ser Leu
    290             295             300

Gly Lys Arg Ala Thr Ile Ser Cys Arg Ala Ser Glu Ser Val Thr Ile
305             310             315             320

Leu Gly Ser His Leu Ile His Trp Tyr Gln Gln Lys Pro Gly Gln Pro
            325             330             335

Pro Thr Leu Leu Ile Gln Leu Ala Ser Asn Val Gln Thr Gly Val Pro
            340             345             350

Ala Arg Phe Ser Gly Ser Gly Ser Arg Thr Asp Phe Thr Leu Thr Ile
            355             360             365

Asp Pro Val Glu Glu Asp Asp Val Ala Val Tyr Tyr Cys Leu Gln Ser
    370             375             380

Arg Thr Ile Pro Arg Thr Phe Gly Gly Gly Thr Lys Leu Glu Ile Lys
385             390             395             400

Gly Ser Thr Ser Gly Ser Gly Lys Pro Gly Ser Gly Glu Gly Ser Thr
            405             410             415

Lys Gly Gln Ile Gln Leu Val Gln Ser Gly Pro Glu Leu Lys Lys Pro
            420             425             430

Gly Glu Thr Val Lys Ile Ser Cys Lys Ala Ser Gly Tyr Thr Phe Thr
            435             440             445

Asp Tyr Ser Ile Asn Trp Val Lys Arg Ala Pro Gly Lys Gly Leu Lys
    450             455             460

Trp Met Gly Trp Ile Asn Thr Glu Thr Arg Glu Pro Ala Tyr Ala Tyr
```

-continued

```
465             470             475             480

Asp Phe Arg Gly Arg Phe Ala Phe Ser Leu Glu Thr Ser Ala Ser Thr
                485             490             495

Ala Tyr Leu Gln Ile Asn Asn Leu Lys Tyr Glu Asp Thr Ala Thr Tyr
            500             505             510

Phe Cys Ala Leu Asp Tyr Ser Tyr Ala Met Asp Tyr Trp Gly Gln Gly
        515             520             525

Thr Ser Val Thr Val Ser Ser Ala Ala Ala Thr Thr Thr Pro Ala Pro
    530             535             540

Arg Pro Pro Thr Pro Ala Pro Thr Ile Ala Ser Gln Pro Leu Ser Leu
545             550             555             560

Arg Pro Glu Ala Cys Arg Pro Ala Ala Gly Gly Ala Val His Thr Arg
            565             570             575

Gly Leu Asp Phe Ala Cys Asp Ile Tyr Ile Trp Ala Pro Leu Ala Gly
            580             585             590

Thr Cys Gly Val Leu Leu Leu Ser Leu Val Ile Thr Leu Tyr Cys Lys
        595             600             605

Arg Gly Arg Lys Lys Leu Leu Tyr Ile Phe Lys Gln Pro Phe Met Arg
    610             615             620

Pro Val Gln Thr Thr Gln Glu Glu Asp Gly Cys Ser Cys Arg Phe Pro
625             630             635             640

Glu Glu Glu Glu Gly Gly Cys Glu Leu Arg Val Lys Phe Ser Arg Ser
            645             650             655

Ala Asp Ala Pro Ala Tyr Gln Gln Gly Gln Asn Gln Leu Tyr Asn Glu
            660             665             670

Leu Asn Leu Gly Arg Arg Glu Glu Tyr Asp Val Leu Asp Lys Arg Arg
    675             680             685

Gly Arg Asp Pro Glu Met Gly Gly Lys Pro Arg Arg Lys Asn Pro Gln
    690             695             700

Glu Gly Leu Tyr Asn Glu Leu Gln Lys Asp Lys Met Ala Glu Ala Tyr
705             710             715             720

Ser Glu Ile Gly Met Lys Gly Glu Arg Arg Arg Gly Lys Gly His Asp
            725             730             735

Gly Leu Tyr Gln Gly Leu Ser Thr Ala Thr Lys Asp Thr Tyr Asp Ala
            740             745             750

Leu His Met Gln Ala Leu Pro Pro Arg
            755             760
```

```
<210> SEQ ID NO 23
<211> LENGTH: 761
<212> TYPE: PRT
<213> ORGANISM: Artificial Sequence
<220> FEATURE:
<223> OTHER INFORMATION: Synthetic

<400> SEQUENCE: 23

Met Ala Leu Pro Val Thr Ala Leu Leu Leu Pro Leu Ala Leu Leu Leu
1               5               10              15

His Ala Ala Arg Pro Asp Ile Val Leu Thr Gln Ser Pro Pro Ser Leu
            20              25              30

Ala Met Ser Leu Gly Lys Arg Ala Thr Ile Ser Cys Arg Ala Ser Glu
        35              40              45

Ser Val Thr Ile Leu Gly Ser His Leu Ile His Trp Tyr Gln Gln Lys
    50              55              60

Pro Gly Gln Pro Pro Thr Leu Leu Ile Gln Leu Ala Ser Asn Val Gln
```

-continued

```
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Val Ala Val Tyr Tyr
            100                 105                 110

Cys Leu Gln Ser Arg Thr Ile Pro Arg Thr Phe Gly Gly Gly Thr Lys
            115                 120                 125

Leu Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
            195                 200                 205

Ala Tyr Ala Tyr Asp Phe Arg Gly Arg Phe Ala Phe Ser Leu Glu Thr
    210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Ala Ala Ala Gly Gly
            260                 265                 270

Gly Gly Ser Gly Gly Gly Gly Ser Gly Gly Gly Ser Gly Gly Gly
            275                 280                 285

Gly Ser Glu Val Gln Leu Gln Gln Ser Gly Pro Glu Leu Val Lys Pro
    290                 295                 300

Gly Ala Ser Val Lys Ile Ser Cys Lys Thr Ser Gly Tyr Thr Phe Thr
305                 310                 315                 320

Glu Ser Thr Ile His Trp Val Lys Gln Ser His Gly Lys Ser Leu Glu
                325                 330                 335

Trp Ile Gly Gly Ile Ser Pro Asn Asn Gly Gly Ser Pro Phe Asn Gln
            340                 345                 350

Lys Phe Lys Gly Lys Ala Thr Leu Thr Val Asp Lys Ser Ser Ser Thr
            355                 360                 365

Val Tyr Met Glu Leu Arg Ser Leu Ser Ser Glu Asp Ser Ala Val Tyr
    370                 375                 380

Tyr Cys Ala Lys Trp Val Arg Gly Ala Met Asp Phe Trp Gly Gln Gly
385                 390                 395                 400

Thr Ser Val Thr Val Ser Ser Gly Gly Gly Ser Gly Gly Gly Gly
                405                 410                 415

Ser Gly Gly Gly Gly Ser Gly Gly Gly Gly Ser Asp Ile Val Leu Thr
            420                 425                 430

Gln Ser Pro Ala Ser Leu Ala Val Ser Leu Gly Gln Arg Ala Thr Ile
            435                 440                 445

Ser Cys Arg Ala Ser Glu Ser Val Asp Tyr Tyr Gly Met Ser Leu Met
    450                 455                 460

Asn Trp Phe Gln Gln Lys Pro Gly Gln Pro Pro Lys Leu Val Ile Tyr
465                 470                 475                 480

Ala Ala Ser Asn Gln Gly Ser Gly Val Pro Ala Arg Phe Ser Gly Ser
                485                 490                 495
```

```
Gly Ser Gly Thr Asp Phe Arg Leu Asn Ile His Pro Leu Glu Glu Asp
        500             505             510

Asp Thr Gly Met Tyr Phe Cys Gln Gln Ser Lys Glu Ala Pro Pro Thr
        515             520             525

Phe Gly Gly Gly Thr Lys Leu Glu Ile Lys Thr Thr Thr Pro Ala Pro
        530             535             540

Arg Pro Pro Thr Pro Ala Pro Thr Ile Ala Ser Gln Pro Leu Ser Leu
545             550             555             560

Arg Pro Glu Ala Cys Arg Pro Ala Ala Gly Gly Ala Val His Thr Arg
            565             570             575

Gly Leu Asp Phe Ala Cys Asp Ile Tyr Ile Trp Ala Pro Leu Ala Gly
            580             585             590

Thr Cys Gly Val Leu Leu Leu Ser Leu Val Ile Thr Leu Tyr Cys Lys
            595             600             605

Arg Gly Arg Lys Lys Leu Leu Tyr Ile Phe Lys Gln Pro Phe Met Arg
        610             615             620

Pro Val Gln Thr Thr Gln Glu Glu Asp Gly Cys Ser Cys Arg Phe Pro
625             630             635             640

Glu Glu Glu Glu Gly Gly Cys Glu Leu Arg Val Lys Phe Ser Arg Ser
            645             650             655

Ala Asp Ala Pro Ala Tyr Gln Gln Gly Gln Asn Gln Leu Tyr Asn Glu
            660             665             670

Leu Asn Leu Gly Arg Arg Glu Glu Tyr Asp Val Leu Asp Lys Arg Arg
        675             680             685

Gly Arg Asp Pro Glu Met Gly Gly Lys Pro Arg Arg Lys Asn Pro Gln
        690             695             700

Glu Gly Leu Tyr Asn Glu Leu Gln Lys Asp Lys Met Ala Glu Ala Tyr
705             710             715             720

Ser Glu Ile Gly Met Lys Gly Glu Arg Arg Gly Lys Gly His Asp
            725             730             735

Gly Leu Tyr Gln Gly Leu Ser Thr Ala Thr Lys Asp Thr Tyr Asp Ala
        740             745             750

Leu His Met Gln Ala Leu Pro Pro Arg
        755             760
```

```
<210> SEQ ID NO 24
<211> LENGTH: 761
<212> TYPE: PRT
<213> ORGANISM: Artificial Sequence
<220> FEATURE:
<223> OTHER INFORMATION: Synthetic

<400> SEQUENCE: 24
```

```
Met Ala Leu Pro Val Thr Ala Leu Leu Leu Pro Leu Ala Leu Leu Leu
1               5               10              15

His Ala Ala Arg Pro Asp Ile Val Leu Thr Gln Ser Pro Ala Ser Leu
            20              25              30

Ala Val Ser Leu Gly Gln Arg Ala Thr Ile Ser Cys Arg Ala Ser Glu
        35              40              45

Ser Val Asp Tyr Tyr Gly Met Ser Leu Met Asn Trp Phe Gln Gln Lys
        50              55              60

Pro Gly Gln Pro Pro Lys Leu Val Ile Tyr Ala Ala Ser Asn Gln Gly
65              70              75              80

Ser Gly Val Pro Ala Arg Phe Ser Gly Ser Gly Ser Gly Thr Asp Phe
            85              90              95
```

```
Arg Leu Asn Ile His Pro Leu Glu Glu Asp Asp Thr Gly Met Tyr Phe
            100             105             110

Cys Gln Gln Ser Lys Glu Ala Pro Pro Thr Phe Gly Gly Gly Thr Lys
            115             120         125

Leu Glu Ile Lys Gly Gly Gly Gly Ser Gly Gly Gly Ser Gly Gly
            130             135             140

Gly Gly Ser Gly Gly Gly Gly Ser Glu Val Gln Leu Gln Gln Ser Gly
145             150             155             160

Pro Glu Leu Val Lys Pro Gly Ala Ser Val Lys Ile Ser Cys Lys Thr
                165             170             175

Ser Gly Tyr Thr Phe Thr Glu Ser Thr Ile His Trp Val Lys Gln Ser
            180             185             190

His Gly Lys Ser Leu Glu Trp Ile Gly Gly Ile Ser Pro Asn Asn Gly
            195             200             205

Gly Ser Pro Phe Asn Gln Lys Phe Lys Gly Lys Ala Thr Leu Thr Val
    210             215             220

Asp Lys Ser Ser Ser Thr Val Tyr Met Glu Leu Arg Ser Leu Ser Ser
225             230             235             240

Glu Asp Ser Ala Val Tyr Tyr Cys Ala Lys Trp Val Arg Gly Ala Met
                245             250             255

Asp Phe Trp Gly Gln Gly Thr Ser Val Thr Val Ser Ser Gly Gly Gly
            260             265             270

Gly Ser Gly Gly Gly Gly Ser Gly Gly Gly Gly Ser Gly Gly Gly Gly
            275             280             285

Ser Asp Ile Val Leu Thr Gln Ser Pro Pro Ser Leu Ala Met Ser Leu
    290             295             300

Gly Lys Arg Ala Thr Ile Ser Cys Arg Ala Ser Glu Ser Val Thr Ile
305             310             315             320

Leu Gly Ser His Leu Ile His Trp Tyr Gln Gln Lys Pro Gly Gln Pro
            325             330             335

Pro Thr Leu Leu Ile Gln Leu Ala Ser Asn Val Gln Thr Gly Val Pro
            340             345             350

Ala Arg Phe Ser Gly Ser Gly Ser Arg Thr Asp Phe Thr Leu Thr Ile
            355             360             365

Asp Pro Val Glu Glu Asp Asp Val Ala Val Tyr Tyr Cys Leu Gln Ser
    370             375             380

Arg Thr Ile Pro Arg Thr Phe Gly Gly Gly Thr Lys Leu Glu Ile Lys
385             390             395             400

Gly Ser Thr Ser Gly Ser Gly Lys Pro Gly Ser Gly Glu Gly Ser Thr
            405             410             415

Lys Gly Gln Ile Gln Leu Val Gln Ser Gly Pro Glu Leu Lys Lys Pro
            420             425             430

Gly Glu Thr Val Lys Ile Ser Cys Lys Ala Ser Gly Tyr Thr Phe Thr
            435             440             445

Asp Tyr Ser Ile Asn Trp Val Lys Arg Ala Pro Gly Lys Gly Leu Lys
    450             455             460

Trp Met Gly Trp Ile Asn Thr Glu Thr Arg Glu Pro Ala Tyr Ala Tyr
465             470             475             480

Asp Phe Arg Gly Arg Phe Ala Phe Ser Leu Glu Thr Ser Ala Ser Thr
            485             490             495

Ala Tyr Leu Gln Ile Asn Asn Leu Lys Tyr Glu Asp Thr Ala Thr Tyr
    500             505             510
```

```
Phe Cys Ala Leu Asp Tyr Ser Tyr Ala Met Asp Tyr Trp Gly Gln Gly
        515                 520                 525

Thr Ser Val Thr Val Ser Ser Ala Ala Ala Thr Thr Thr Pro Ala Pro
        530                 535                 540

Arg Pro Pro Thr Pro Ala Pro Thr Ile Ala Ser Gln Pro Leu Ser Leu
545                     550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
                580                 585                 590

Thr Cys Gly Val Leu Leu Leu Ser Leu Val Ile Thr Leu Tyr Cys Lys
                595                 600                 605

Arg Gly Arg Lys Lys Leu Leu Tyr Ile Phe Lys Gln Pro Phe Met Arg
        610                 615                 620

Pro Val Gln Thr Thr Gln Glu Glu Asp Gly Cys Ser Cys Arg Phe Pro
625                     630                 635                 640

Glu Glu Glu Glu Gly Gly Cys Glu Leu Arg Val Lys Phe Ser Arg Ser
                645                 650                 655

Ala Asp Ala Pro Ala Tyr Gln Gln Gly Gln Asn Gln Leu Tyr Asn Glu
                660                 665                 670

Leu Asn Leu Gly Arg Arg Glu Glu Tyr Asp Val Leu Asp Lys Arg Arg
        675                 680                 685

Gly Arg Asp Pro Glu Met Gly Gly Lys Pro Arg Arg Lys Asn Pro Gln
        690                 695                 700

Glu Gly Leu Tyr Asn Glu Leu Gln Lys Asp Lys Met Ala Glu Ala Tyr
705                     710                 715                 720

Ser Glu Ile Gly Met Lys Gly Glu Arg Arg Gly Lys Gly His Asp
                725                 730                 735

Gly Leu Tyr Gln Gly Leu Ser Thr Ala Thr Lys Asp Thr Tyr Asp Ala
                740                 745                 750

Leu His Met Gln Ala Leu Pro Pro Arg
        755                 760
```

```
<210> SEQ ID NO 25
<211> LENGTH: 761
<212> TYPE: PRT
<213> ORGANISM: Artificial Sequence
<220> FEATURE:
<223> OTHER INFORMATION: Synthetic

<400> SEQUENCE: 25

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
        20                  25                  30

Ala Met Ser Leu Gly Lys Arg Ala Thr Ile Ser Cys Arg Ala Ser Glu
        35                  40                  45

Ser Val Thr Ile Leu Gly Ser His Leu Ile His Trp Tyr Gln Gln Lys
        50                  55                  60

Pro Gly Gln Pro Pro Thr Leu Leu Ile Gln Leu Ala Ser Asn Val Gln
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Asp Val Ala Val Tyr Tyr
        100                 105                 110
```

```
Cys Leu Gln Ser Arg Thr Ile Pro Arg Thr Phe Gly Gly Thr Lys
        115                 120                 125

Leu Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
        195                 200                 205

Ala Tyr Ala Tyr Asp Phe Arg Gly Arg Phe Ala Phe Ser Leu Glu Thr
    210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
            245                 250                 255

Trp Gly Gln Gly Thr Ser Val Thr Val Ser Ser Ala Ala Ala Gly Gly
            260                 265                 270

Gly Gly Ser Gly Gly Gly Gly Ser Gly Gly Gly Gly Ser Gly Gly Gly
        275                 280                 285

Gly Ser Asp Ile Val Leu Thr Gln Ser Pro Ala Ser Leu Ala Val Ser
        290                 295                 300

Leu Gly Gln Arg Ala Thr Ile Ser Cys Arg Ala Ser Glu Ser Val Asp
305                 310                 315                 320

Tyr Tyr Gly Met Ser Leu Met Asn Trp Phe Gln Gln Lys Pro Gly Gln
            325                 330                 335

Pro Pro Lys Leu Val Ile Tyr Ala Ala Ser Asn Gln Gly Ser Gly Val
            340                 345                 350

Pro Ala Arg Phe Ser Gly Ser Gly Ser Gly Thr Asp Phe Arg Leu Asn
        355                 360                 365

Ile His Pro Leu Glu Glu Asp Asp Thr Gly Met Tyr Phe Cys Gln Gln
    370                 375                 380

Ser Lys Glu Ala Pro Pro Thr Phe Gly Gly Gly Thr Lys Leu Glu Ile
385                 390                 395                 400

Lys Gly Gly Gly Gly Ser Gly Gly Gly Gly Ser Gly Gly Gly Gly Ser
                405                 410                 415

Gly Gly Gly Gly Ser Glu Val Gln Leu Gln Gln Ser Gly Pro Glu Leu
        420                 425                 430

Val Lys Pro Gly Ala Ser Val Lys Ile Ser Cys Lys Thr Ser Gly Tyr
        435                 440                 445

Thr Phe Thr Glu Ser Thr Ile His Trp Val Lys Gln Ser His Gly Lys
    450                 455                 460

Ser Leu Glu Trp Ile Gly Gly Ile Ser Pro Asn Asn Gly Gly Ser Pro
465                 470                 475                 480

Phe Asn Gln Lys Phe Lys Gly Lys Ala Thr Leu Thr Val Asp Lys Ser
                485                 490                 495

Ser Ser Thr Val Tyr Met Glu Leu Arg Ser Leu Ser Ser Glu Asp Ser
            500                 505                 510

Ala Val Tyr Tyr Cys Ala Lys Trp Val Arg Gly Ala Met Asp Phe Trp
            515                 520                 525

Gly Gln Gly Thr Ser Val Thr Val Ser Ser Thr Thr Thr Pro Ala Pro
```

-continued

```
      530               535               540

Arg Pro Pro Thr Pro Ala Pro Thr Ile Ala Ser Gln Pro Leu Ser Leu
545               550               555               560

Arg Pro Glu Ala Cys Arg Pro Ala Ala Gly Gly Ala Val His Thr Arg
              565               570               575

Gly Leu Asp Phe Ala Cys Asp Ile Tyr Ile Trp Ala Pro Leu Ala Gly
              580               585               590

Thr Cys Gly Val Leu Leu Leu Ser Leu Val Ile Thr Leu Tyr Cys Lys
              595               600               605

Arg Gly Arg Lys Lys Leu Leu Tyr Ile Phe Lys Gln Pro Phe Met Arg
              610               615               620

Pro Val Gln Thr Thr Gln Glu Glu Asp Gly Cys Ser Cys Arg Phe Pro
625               630               635               640

Glu Glu Glu Glu Gly Gly Cys Glu Leu Arg Val Lys Phe Ser Arg Ser
              645               650               655

Ala Asp Ala Pro Ala Tyr Gln Gln Gly Gln Asn Gln Leu Tyr Asn Glu
              660               665               670

Leu Asn Leu Gly Arg Arg Glu Glu Tyr Asp Val Leu Asp Lys Arg Arg
              675               680               685

Gly Arg Asp Pro Glu Met Gly Gly Lys Pro Arg Arg Lys Asn Pro Gln
              690               695               700

Glu Gly Leu Tyr Asn Glu Leu Gln Lys Asp Lys Met Ala Glu Ala Tyr
705               710               715               720

Ser Glu Ile Gly Met Lys Gly Glu Arg Arg Arg Gly Lys Gly His Asp
              725               730               735

Gly Leu Tyr Gln Gly Leu Ser Thr Ala Thr Lys Asp Thr Tyr Asp Ala
              740               745               750

Leu His Met Gln Ala Leu Pro Pro Arg
              755               760

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Gly Tyr Thr Phe Thr Glu Ser Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Ile Ser Pro Asn Asn Gly Gly Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28
```

-continued

```
Ala Lys Trp Val Arg Gly Ala Met Asp Phe
1               5               10

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Glu Ser Val Asp Tyr Tyr Gly Met Ser Leu
1               5               10

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Gln Gln Ser Lys Glu Ala Pro Pro Thr
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic

<400> SEQUENCE: 32

Glu Ser Thr Ile His
1               5

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

Gly Ile Ser Pro Asn Asn Gly Gly Ser Pro Phe Asn Gln Lys Phe Lys
1               5               10              15

Gly

<210> SEQ ID NO 34
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 34

Trp Val Arg Gly Ala Met Asp Phe
1               5

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Arg Ala Ser Glu Ser Val Asp Tyr Tyr Gly Met Ser Leu Met Asn
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Ala Ala Ser Asn Gln Gly Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Gly Tyr Thr Phe Thr Glu Ser
1               5

<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Asn Asn Gly
1

<210> SEQ ID NO 39
<211> LENGTH: 6
<212> TYPE: PRT
<213> ORGANISM: Artificial Sequence
<220> FEATURE:
<223> OTHER INFORMATION: Synthetic

<400> SEQUENCE: 39

Val Arg Gly Ala Met Asp
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40
```

-continued

```
Ser Glu Ser Val Asp Tyr Tyr Gly Met Ser Leu
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Synthetic

<400> SEQUENCE: 41

Ser Lys Glu Ala Pro Pro
1               5
```